(12) United States Patent
Cockerill et al.

(10) Patent No.: US 6,828,320 B2
(45) Date of Patent: Dec. 7, 2004

(54) HETEROCYCLIC COMPOUNDS

(75) Inventors: George Stuart Cockerill, Bedford (GB); Malcolm Clive Carter, Ware (GB); Stephen Barry Guntrip, Hertford (GB); Kathryn Jane Smith, Bishop's Stortford (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/062,647

(22) Filed: Jan. 31, 2002

(65) Prior Publication Data

US 2002/0147214 A1 Oct. 10, 2002

Related U.S. Application Data

(63) Continuation of application No. 09/214,267, filed as application No. PCT/EP97/03672 on Dec. 31, 1998, now Pat. No. 6,391,874.

(30) Foreign Application Priority Data

Jul. 13, 1996 (GB) .............................................. 9614755
Dec. 7, 1996 (GB) .............................................. 9625458

(51) Int. Cl.[7] .................... A61K 31/535; A61K 31/495; A61K 31/505; A61K 31/47
(52) U.S. Cl. .................... 514/233.5; 514/255; 514/258; 514/312
(58) Field of Search ............................ 514/233.5, 258, 514/312, 255

(56) References Cited

U.S. PATENT DOCUMENTS

| | | |
|---|---|---|
| 5,457,105 A | 10/1995 | Barker |
| 5,480,883 A | 1/1996 | Spada et al. |
| 5,616,582 A | 4/1997 | Barker |
| 5,646,153 A | 7/1997 | Spada et al. |

FOREIGN PATENT DOCUMENTS

| | | |
|---|---|---|
| EP | 0 566 226 | 10/1993 |
| EP | 0635507 | 7/1994 |
| WO | 95/15758 | 6/1995 |
| WO | 95/19774 | 7/1995 |
| WO | 96/07657 | 3/1996 |
| WO | 96/09294 | 3/1996 |
| WO | 96/15128 | 3/1996 |
| WO | 96/15118 | 5/1996 |
| WO | 96/16960 | 6/1996 |
| WO | 97/03069 | 1/1997 |
| WO | 97/30034 | 8/1997 |

OTHER PUBLICATIONS

A.F. Wilks, *Progress in Growth Factor Research*, 1990, vol. 2, pp. 97–111.
S.A. Courtneidge, *Dev. Suppl.*, 1993, pp. 57–64.
J.A. Cooper, *Semin. Cell Biol.*, 1994, vol. 5, No. 6, pp. 377–387.
R.F. Paulson, *Semin. Immunol.*, 1995, vol. 7, No. 4, pp. 267–277.
A.C. Chan, *Curr. Opin. Immunol.*, 1996, vol. 8, No. 3, pp. 394–401.
Dvir et al., *J. Cell. Biol.*, 1991, vol. 113, pp. 857–865.
Buchdunger et al., *Proc. Natl. Acad. Sci. USA*, 1991, vol. 92, pp. 2258–2262.
Berkois, *Blood*, 1992, vol. 79, No. 9, pp. 2446–2454.
Salari et al., *FEBS*, 1990, vol. 263, No. 1, pp. 104–108.
Ohmichi et al., *Biochemistry*, 1992, vol. 31, pp. 4034–4039.
L.K. Shawyer, *DDT*, 1997, vol. 2, No. 2, pop. 50–63.
Sainsbury et al., *Brit. J. Cancer*, 1988, vol. 58, pp. 458.
Yaish et al., *Science*, 1988, vol. 242, pp. 933.
Klausner and Samelson, Cell, 1991, vol. 64, pp. 875–878.
Bridges et al., "Tyrosine Kinase Inhibitors," *J. Med. Chem.*, vol. 39, No. 1, pp. 267–276 (Jan. 5, 1996).
Rewcastle et al., "Tyrosine Kinase Inhibitors," *J. Med. Chem.*, vol. 38, No. 18, pp. 3482–3487 (1995).

*Primary Examiner*—Rebecca Cook
(74) *Attorney, Agent, or Firm*—John L. Lemanowicz

(57) ABSTRACT

Substituted heteroaromatic compounds, and in particular substituted quinolines and quinazolines, are protein tyrosine kinase inhibitors. The compounds are described as are methods for their preparation, pharmaceutical compositions including such compounds and their use in medicine, for example in the treatment of cancer and psoriasis.

23 Claims, No Drawings

HETEROCYCLIC COMPOUNDS

This application is a continuation of U.S. patent application Ser. No. 09/214,267 filed Dec. 31, 1998, which issued May 21, 2002, as U.S. Pat. No. 6,391,874, which is a 35 U.S.C. 371 United States National Phase Application of PCT/EP97/03672 filed Dec. 31, 1998, which claims priority to GB 9614755.8 filed Jul. 13, 1996 and GB 9625458.6 filed Dec. 7, 1996.

The present invention relates to a series of substituted heteroaromatic compounds, methods for their preparation, pharmaceutical compositions containing them and their use in medicine. In particular, the invention relates to quinoline and quinazoline derivatives which exhibit protein tyrosine kinase inhibition.

Protein tyrosine kinases catalyse the phosphorylation of specific tyrosyl residues in various proteins involved in the regulation of cell growth and differentiation (A. F. Wilks, Progress in Growth Factor Research, 1990, 2, 97–111; S. A. Courtneidge, Dev. Supp.I, 1993, 57–64; J. A. Cooper, Semin. Cell Biol., 1994, 5(6), 377–387; R. F. Paulson, Semin. Immunol., 1995, 7(4), 267–277; A. C. Chan, Curr. Opin. Immunol., 1996, 8(3), 394–401). Protein tyrosine kinases can be broadly classified as receptor (e.g. EGFr, c-erbB-2, c-met, tie-2, PDGFr, FGFr) or non-receptor (e.g. c-src, lck, Zap70) kinases. Inappropriate or uncontrolled activation of many of these kinase, i.e. aberrant protein tyrosine kinase activity, for example by over-expression or mutation, has been shown to result in uncontrolled cell growth.

Aberrant activity of protein tyrosine kinases, such as c-erbB-2, c-src, c-met, EGFr and PDGFr have been implicated in human malignancies. Elevated EGFr activity has, for example, been implicated in non-small cell lung, bladder and head and neck cancers, and increased c-erbB-2 activity in breast, ovarian, gastric and pancreatic cancers. Inhibition of protein tyrosine kinases should therefore provide a treatment for tumours such as those outlined above.

Aberrant protein tyrosine kinase activity has also been implicated in a variety of other disorders: psoriasis, (Dvir et al, J.Cell.Biol; 1991, 113, 857–865), fibrosis, atherosclerosis, restenosis, (Buchdunger et al, Proc.Natl.Acad.Sci. USA; 1991, 92, 2258–2262), auto-immune disease, allergy, asthma, transplantation rejection (Klausner and Samelson, Cell; 1991, 64, 875–878), inflammation (Berkois, Blood; 1992, 79(9), 2446–2454), thrombosis (Salari et al, FEBS; 1990, 263(1), 104–108) and nervous system diseases (Ohmichi et al, Biochemistry, 1992, 31, 4034–4039). Inhibitors of the specific protein tyrosine kinases involved in these diseases eg PDGF-R in restenosis and EGF-R in psoriasis, should lead to novel therapies for such disorders. P56lck and zap 70 are indicated in disease conditions in which T cells are hyperactive e.g. rheumatoid arthritis, autoimmune disease, allergy, asthma and graft rejection. The process of angiogenesis has been associated with a number of disease states (e.g. tumourogenesis, psoriasis, rheumatoid arthritis) and this has been shown to be controlled through the action of a number of receptor tyrosine kinases (L. K. Shawver, DDT, 1997, 2(2), 50–63).

EP0635507 discloses a class of tricyclic quinazoline derivatives of the formula:

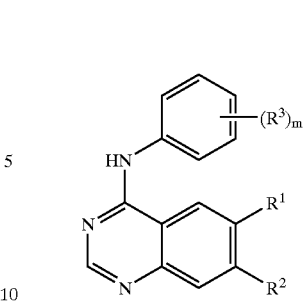

wherein $R^1$ and $R^2$ together form specified optionally substituted groups containing at least one heteroatom so as to form a 5 or 6-membered ring, in which there is a N atom at the 6 position of the quinazoline ring; $R^3$ includes independently hydrogen, hydroxy, halogeno, (1–4C)alkyl, (1–4C)alkoxy di-[(1–4C)alkyl]amino, or (2–4C)alkanoylamino. The above citation notes that receptor tyrosine kinases in general, which are important in the transmission of biochemical signals initiating cell replication, are frequently present at increased levels or with higher activities in common human cancers such as breast cancer (Sainsbury et al, Brit. J. Cancer, 1988, 58, 458). It is suggested that inhibitors of receptor tyrosine kinase should be of value as inhibitors of the growth of mammalian cancer cells (Yaish et al. Science, 1988, 242, 933). This citation therefore has the aim of providing quinazoline derivatives which inhibit receptor tyrosine kinases involved in controlling the tumourigenic phenotype.

WO 95/15758 discloses aryl and heteroaryl quinazoline derivatives of formula

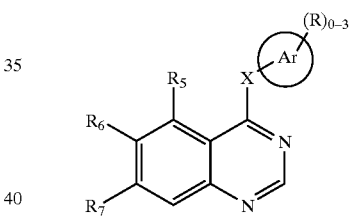

wherein X includes a bond, O, S, SO, $SO_2$, C≡C, C=C, $CH_2$ and NH; Ar includes phenyl, naphthyl, naphthalenyl, indolyl, pyridyl, piperidinyl, piperazinyl, dihydroquinolinyl, tetrahydroquinolinyl, thienyl, indanyl, pyrazolyl and 1,4-benzodioxanyl; and $R_5$, $R_6$ and $R_7$ independently include hydrogen, alkyl, alkylthio, cycloalkyl, hydroxy, alkoxy, aralkoxy, aryl, halo, haloalkyl, carboxy or carbalkoxy; as inhibitors of CSF-1R and/or p56lck receptor tyrosine kinase activity.

WO 95/19774 discloses bicyclic derivatives of formula:

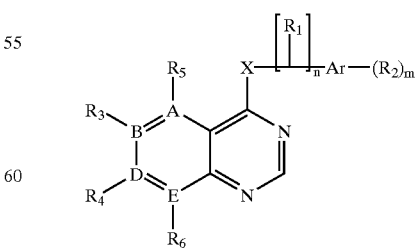

in which A to E are nitrogen or carbon and at least one of A to E is nitrogen; or two adjacent atoms together are N, O or S; $R_1$ is H or alkyl and n is 0, 1 or 2; m is 0 to 3 and $R_2$ includes optionally substituted alkyl, alkoxy, cycloalkoxy, cycloalkoxy, or two $R_2$ groups together form a carbocycle or heterocycle. The compounds are said to inhibit epidermal growth factor receptor tyrosine kinase and suggested uses include the treatment of cancer, psoriasis, kidney disease, pancreatitis and contraception.

WO 96/07657 discloses pyrimido[5,4-d]pyrimidine derivatives of formula

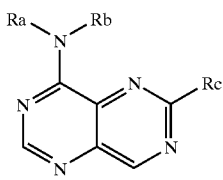

wherein Ra includes hydrogen or alkyl; Rb includes optionally substituted phenyl; and Rc includes hydrogen, halo, alkyl, cycloalkyl, cycloalkylalkylaryl, aralkyl, OH, optionally substituted alkoxy, cycloalkoxy, aryloxy, aralkoxy, mercapto, optionally substituted alkyl- or arylsulfenyl, -sulfinyl, or -sulfonyl and substituted alkyleneimino; as EGF-R inhibitors.

WO 96/09294 discloses quinoline and quinazoline derivatives of formula

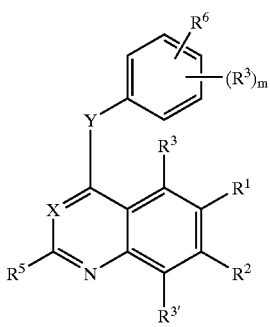

wherein X is N or CH; Y includes O, S, $CH_2O$ and NH; $R^6$ includes phenoxy, benzyloxy, benzylmercapto, benzylamino, benzyl, anilino, benzoyl, anilinocarbonyl, anilinomethyl, phenylethynyl, phenylethenyl, phenylethyl, phenylthio, phenylsulphonyl, benzylthio, benzylsulphonyl, phenylthiomethyl, phenylsulphonylmethyl, phenoxymethyl, thienylmethoxy, furanylmethoxy, cyclohexyl, and cyclohexylmethoxy; and $R^1$, $R^2$, $R^3$ and $R^{3'}$ include a range of possible substituents, predominantly not including heterocyclic ring systems; as protein receptor tyrosine kinase inhibitors, in particular as c-erbB-2 and/or p56lck inhibitors.

WO 96/15118 discloses quinazoline derivatives of formula

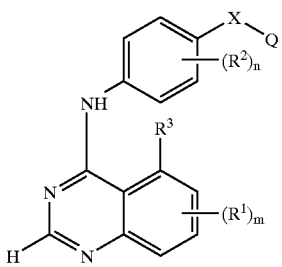

wherein X includes O, S, SO, $SO_2$, $CH_2$, $OCH_2$, $CH_2O$ and CO; Q includes a phenyl or naphthyl group and various 5- or 6-membered heteroaryl moieties; n is 0, 1, 2 or 3 and each $R^2$ is independently halogeno, trifluoromethyl, hydroxy, amino, nitro, cyano, $C_{1-4}$ alkyl, $C_{1-4}$ alkoxy, $C_{1-4}$ alkylamino, $diC_{1-4}$ alkyl amino or $C_{2-4}$ alkanoylamino; m is 1, 2 or 3 and $R^1$ includes a range of possible substituents, predominantly not including heterocyclic ring systems; as receptor tyrosine kinase inhibitors, in particular as EGF-R inhibitors.

WO 96/15128 discloses pyrido[2,3-d]pyrimidine and naphthyridine derivatives of formula

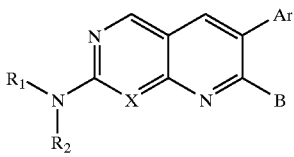

wherein X is CH or N; B is halo, hydroxy or $NR_3R_4$; Ar includes unsubstituted and substituted phenyl or pyridyl; and $R_1$, $R_2$, $R_3$ and $R_4$ independently include hydrogen, amino, $C_{1-8}$alkylamino, di-$C_{1-8}$alkylamino, unsubstituted and substituted aromatic or heteroaromatic groups, and unsubstituted and substituted $C_{1-8}$alkyl, $C_{2-8}$alkenyl or $C_{2-8}$alkynyl groups.

WO 96/16960 discloses quinazoline derivatives of formula

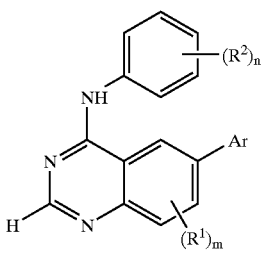

wherein m is 1 or 2; each $R^1$ independently includes hydrogen and $C_{1-4}$alkoxy; n is 1, 2 or 3; each $R^2$ independently includes hydrogen, halogeno and $C_{1-4}$alkyl, or $R^2$ is an aryl- or heteroaryl-containing group, including pyridylmethoxy and benzoyl; and Ar includes a substituted or unsubstituted 5- or 9-membered nitrogen-linked heteroaryl moiety containing up to four nitrogen atoms, in particular imidazol-1-yl, imidazolin-1-yl, benzimidazol-1-yl, pyrazol-1-yl and 1,2,4-triazol-1-yl; as receptor tyrosine kinase inhibitors, in particular as EGF-R inhibitors.

It is therefore a general object of the present invention to provide compounds suitable for the treatment of disorders mediated by protein tyrosine kinase activity, and in particular treatment of the above mentioned disorders.

In addition to the treatment of tumours, the present invention envisages that other disorders mediated by protein tyrosine kinase activity may be treated effectively by inhibition, including preferential inhibition, of the appropriate protein tyrosine kinase activity.

Broad spectrum inhibition of protein tyrosine kinase may not always provide optimal treatment of, for example tumours, and could in certain cases even be detrimental to subjects since protein tyrosine kinases provide an essential role in the normal regulation of cell growth.

It is another object of the present invention to provide compounds which preferentially inhibit protein tyrosine kinases, such as EGFr, c-erbB-2, c-erbB-4, c-met, tie-2, PDGFr, c-src, lck, Zap70, and fyn. There is also perceived to be a benefit in the preferential inhibition involving small groups of protein tyrosine kinases, for example c-erbB-2 and c-erbB-4 or c-erbB-2, c-erbB-4 and EGF-R.

A further object of the present invention is to provide compounds useful in the treatment of protein tyrosine kinase related diseases which minimise undesirable side-effects in the recipient.

The present invention relates to heterocyclic compounds which may be used to treat disorders mediated by protein tyrosine kinases and in particular have anti-cancer properties. More particularly, the compounds of the present invention are potent inhibitors of protein tyrosine kinases such as such as EGFr, c-erbB-2, c-erbB-4, c-met, tie-2, PDGFr, c-src, lck, Zap70, and fyn, thereby allowing clinical management of particular diseased tissues.

The present invention envisages, in particular, the treatment of human malignancies, for example breast, non-small cell lung, ovary, stomach, and pancreatic tumours, especially those driven by EGFr or erbB-2, using the compounds of the present invention. For example, the invention includes compounds which are highly active against the c-erbB-2 protein tyrosine kinase often in preference to the EGF receptor kinase hence allowing treatment of c-erbB-2 driven tumours. However, the invention also includes compounds which are highly active against both c-erbB-2 and EGF-R receptor kinases hence allowing treatment of a broader range of tumours.

More particularly, the present invention envisages that disorders mediated by protein tyrosine kinase activity may be treated effectively by inhibition of the appropriate protein tyrosine kinase activity in a relatively selective manner, thereby minimising potential side effects.

Accordingly, the present invention provides a compound of formula (I):

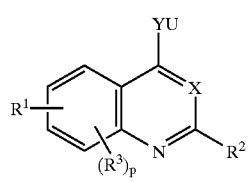

(I)

or a salt thereof;
wherein X is N or CH;
Y is a group $W(CH_2)$, $(CH_2)W$, or W, in which W is O, $S(O)_m$ wherein m is 0, 1 or 2, or $NR^a$ wherein $R^a$ is hydrogen or a $C_{1-8}$ alkyl group;

$R^1$ represents a phenyl group or a 5- or 6-membered heterocyclic ring containing 1 to 4 heteroatoms selected from N, O or $S(O)_m$, wherein m is as defined above, with the provisos that the ring does not contain two adjacent O or $S(O)_m$ atoms and that where the ring contains only N as heteroatom(s) the ring is C-linked to the quinazoline or quinoline ring, $R^1$ being optionally substituted by one or more $R^3$ groups;

each $R^3$ is independently selected from the group comprising amino, hydrogen, halogen, hydroxy, nitro, carboxy, formyl, cyano, trifluoromethyl, trifluoromethoxy, carbamoyl, ureido, guanidino, $C_{1-8}$ alkyl, $C_{1-8}$ alkoxy, $C_{3-8}$ cycloalkoxyl, $C_{4-8}$ alkylcycloalkoxy, $C_{1-8}$ alkylcarbonyl, $C_{1-8}$ alkoxycarbonyl, $\underline{N}$-$C_{1-4}$ alkylcarbamoyl, $\underline{N},\underline{N}$-di-[$C_{1-4}$ alkyl]carbamoyl, hydroxyamino, $C_{1-4}$ alkoxyamino, $C_{2-4}$ alkanoyloxyamino, $C_{1-4}$ alkylamino, di[$C_{1-4}$ alkyl]amino, di-[$C_{1-4}$ alkyl]amino-$C_{1-4}$ alkylene-($C_{1-4}$ alkyl)amino, $C_{1-4}$ alkylamino-$C_{1-4}$ alkylene-($C_{1-4}$ alkyl)amino, hydroxy-$C_{1-4}$ alkylene-($C_{1-4}$ alkyl)amino, phenyl, phenoxy, 4-pyridon-1-yl, pyrrolidin-1-yl, imidazol-1-yl, piperidino, morpholino, thiomorpholino, thiomorpholino-1-oxide, thiomorpholino-1,1-dioxide, piperazin-1-yl, 4-$C_{1-4}$ alkylpiperazin-1-yl, dioxolanyl, $C_{1-8}$ alkylthio, arylthio, $C_{1-4}$ alkylsulphinyl, $C_{1-4}$ alkylsulphonyl, arylsulphonyl, arylsulphinyl, halogeno-$C_{1-4}$ alkyl, hydroxy-$C_{1-4}$ alkyl, $C_{2-4}$ alkanoyloxy-$C_{1-4}$ alkyl, $C_{1-4}$ alkoxy-$C_{1-4}$ alkyl, carboxy-$C_{1-4}$ alkyl, formyl-$C_{1-4}$ alkyl, $C_{1-4}$ alkoxycarbonyl-$C_{1-4}$-alkyl, carbamoyl-$C_{1-4}$ alkyl, $\underline{N}$-$C_{1-4}$ alkylcarbamoyl-$C_{1-4}$alkyl, $\underline{N},\underline{N}$-di-[$C_{1-4}$ alkyl]carbamoyl-$C_{1-4}$alkyl, amino-$C_{1-4}$ alkyl, $C_{1-4}$ alkylamino-$C_{1-4}$ alkyl, di-[$C_{1-4}$ alkyl]amino-$C_{1-4}$ alkyl, phenyl-$C_{1-4}$ alkyl, 4-pyridon-1-yl-$C_{1-4}$ alkyl, pyrrolidin-1-yl-$C_{1-4}$ alkyl, imidazol-1-yl-$C_{1-4}$ alkyl, piperidino-$C_{1-4}$ alkyl, morpholino-$C_{1-4}$ alkyl, thiomorpholino-$C_{1-4}$ alkyl, thiomorpholino-1-oxide-$C_{1-4}$alkyl, thiomorpholino-1,1-dioxide-$C_{1-4}$alkyl, piperazin-1-yl-$C_{1-4}$alkyl, 4-$C_{1-4}$ alkylpiperazin-1-yl-$C_{1-4}$ alkyl, hydroxy-$C_{2-4}$ alkoxy-$C_{1-4}$ alkyl, $C_{1-4}$ alkoxy-$C_{2-4}$ alkoxy-$C_{1-4}$ alkyl, hydroxy-$C_{2-4}$ alkylamino-$C_{1-4}$ alkyl, $C_{1-4}$ alkoxy-$C_{2-4}$ alkylamino-$C_{1-4}$ alkyl, $C_{1-4}$ alkylthio-$C_{1-4}$ alkyl, $C_{1-4}$ alkylsulphinyl-$C_{1-4}$ alkyl, $C_{1-4}$ alkylsulphonyl-$C_{1-4}$ alkyl, hydroxy-$C_{2-4}$ alkylthio-$C_{1-4}$ alkyl, $C_{1-4}$ alkoxy-$C_{2-4}$ alkylthio-$C_{1-4}$ alkyl, phenoxy-$C_{1-4}$ alkyl, anilino-$C_{1-4}$ alkyl, phenylthio-$C_{1-4}$ alkyl, cyano-$C_{1-4}$ alkyl, halogeno-$C_{2-4}$ alkoxy, hydroxy-$C_{2-4}$ alkoxy, $C_{2-4}$ alkanoyloxy-$C_{2-4}$ alkoxy, $C_{1-4}$ alkoxy-$C_{2-4}$ alkoxy, carboxy-$C_{1-4}$ alkoxy, formyl-$C_{1-4}$ alkoxy, $C_{1-4}$ alkoxycarbonyl-$C_{1-4}$ alkoxy, carbamoyl-$C_{1-4}$ alkoxy, $\underline{N}$-$C_{1-4}$ alkylcarbamoyl-$C_{1-4}$ alkoxy, $\underline{N},\underline{N}$-di-[$C_{1-4}$ alkyl]carbamoyl-$C_{1-4}$ alkoxy, amino-$C_{2-4}$ alkoxy, $C_{1-4}$ alkylamino-$C_{2-4}$ alkoxy, di-[$C_{1-4}$ alkyl]amino-$C_{2-4}$ alkoxy, di-[$C_{1-4}$ alkyl-$C_{2-4}$ alkoxy]amino-$C_{2-4}$ alkoxy, $C_{2-4}$ alkanoyloxy, hydroxy-$C_{2-4}$ alkanoyloxy, $C_{1-4}$alkoxy-$C_{2-4}$ alkanoyloxy, phenyl-$C_{1-4}$ alkoxy, phenoxy-$C_{2-4}$ alkoxy, anilino-$C_{2-4}$ alkoxy, phenylthio-$C_{2-4}$ alkoxy, 4-pyridon-1-yl-$C_{2-4}$ alkoxy, piperidino-$C_{2-4}$ alkoxy, morpholino-$C_{2-4}$ alkoxy, thiomorpholino-$C_{2-4}$ alkoxy, thiomorpholino-1-oxide-$C_{2-4}$ alkoxy, thiomorpholino-1,1-dioxide-$C_{2-4}$ alkoxy, piperazin-1-yl-$C_{2-4}$ alkoxy, 4-$C_{1-4}$ alkylpiperazin-1-yl-$C_{2-4}$ alkoxy, pyrrolidin-1-yl-$C_{2-4}$ alkoxy, imidazol-1-yl-$C_{2-4}$ alkoxy, halogeno-$C_{2-4}$ alkylamino, hydroxy-$C_{2-4}$ alkylamino, $C_{2-4}$ alkanoyloxy-$C_{2-4}$ alkylamino, $C_{1-4}$ alkoxy-$C_{2-4}$ alkylamino, carboxy-$C_{1-4}$ alkylamino, $C_{1-4}$ alkoxycarbonyl-$C_{1-4}$ alkylamino, carbamoyl-$C_{1-4}$ alkylamino, $\underline{N}$-$C_{1-4}$ alkylcarbamoyl-$C_{1-4}$ alkylamino, $\underline{N},\underline{N}$-di-[$C_{1-4}$ alkyl]carbamoyl-$C_{1-4}$ alkylamino, amino-$C_{2-4}$ alkylamino, $C_{1-4}$ alkylamino-$C_{2-4}$ alkylamino, di-[$C_{1-4}$alkyl]amino-$C_{2-4}$ alkylamino, phenyl-$C_{1-4}$ alkylamino, phenoxy-$C_{2-4}$ alkylamino, anilino-$C_{2-4}$ alkylamino, 4-pyridon-1-yl-$C_{2-4}$ alkylamino, pyrrolidin-1-yl-$C_{2-4}$ alkylamino, imidazol-1-yl-$C_{2-4}$ alkylamino, piperidino-$C_{2-4}$ alkylamino, morpholino-$C_{2-4}$ alkylamino, thiomorpholino-$C_{2-4}$ alkylamino, thiomorpholino-1-oxide-$C_{2-4}$ alkylamino, thiomorpholino-1,1-dioxide-$C_{2-4}$ alkylamino, piperazin-1-yl-$C_{2-4}$alkylamino, 4-($C_{1-4}$alkyl)piperazin-1-yl-$C_{2-4}$alkylamino, phenylthio-$C_{2-4}$ alkylamino, $C_{2-4}$ alkanoylamino, $C_{1-4}$ alkoxycarbonylamino, $C_{1-4}$ alkylsulphonylamino, $C_{1-4}$ alkylsulphinylamino, benzamido, benzenesulphonamido, 3-phenylureido, 2-oxopyrrolidin-1-yl, 2,5-dioxopyrrolidin-1-yl, halogeno-$C_{2-4}$ alkanoylamino, hydroxy-$C_{2-4}$ alkanoylamino, hydroxy-$C_{2-4}$ alkanoyl-($C_{1-4}$ alkyl)-amino, $C_{1-4}$ alkoxy-$C_{2-4}$ alkanoylamino, carboxy-$C_{2-4}$ alkanoylamino, $C_{1-4}$ alkoxycarbonyl-$C_{2-4}$ alkanoylamino, carbamoyl-$C_{2-4}$ alkanoylamino, N-$C_{1-4}$ alkylcarbamoyl-$C_{2-4}$ alkanoylamino, N,N-di-[$C_{1-4}$ alkyl]carbamoyl-$C_{2-4}$ alkanoylamino, amino-$C_{2-4}$ alkanoylamino, $C_{1-4}$ alkylamino-$C_{2-4}$ alkanoylamino or di-[$C_{1-4}$ alkyl]amino-$C_{2-4}$ alkanoylamino; and wherein said benzamido or benzenesulphonamido substitutent or any anilino, phenoxy or phenyl group on a $R^3$ substituent may optionally bear one or two halogeno, $C_{1-4}$ alkyl or $C_{1-4}$ alkoxy substituents; and wherein any substituent containing a heterocyclic ring may optionally bear one or two halogeno, $C_{1-4}$ alkyl or $C_{1-4}$ alkoxy substituents on said ring; and wherein any substituent containing a heterocyclic ring may optionally bear one or two oxo or thioxo substituents on said ring;

or $R^3$ represents a group selected from $M^1$-$M^2$-$M^3$-$M^4$, $M^1$-$M^5$ or $M^1$-$M^2$-$M^{3'}$-$M^6$ wherein $M^1$ represents a $C_{1-4}$ alkyl group, wherein optionally a $CH_2$ group is replaced by a CO group;

$M^2$ represents $NR^{12}$ or $CR^{12}R^{13}$, in which $R^{12}$ and $R^{13}$ each independently represent H or $C_{1-4}$ alkyl;

$M^3$ represents a $C_{1-4}$ alkyl group;

$M^{3'}$ represents a $C_{1-4}$ alkyl group or is absent;

$M^4$ represents CN, $NR^{12}S(O)_mR^{13}$, $S(O)_mNR^{14}R^{15}$, $CONR^{14}R^{15}$, $S(O)_mR^{13}$ or $CO_2R^{13}$, in which $R^{12}$, $R^{13}$ and m are as hereinbefore defined and $R^{14}$ and $R^{15}$ each independently represent H or $C_{1-4}$ alkyl, or $R^{14}$ and $R^{15}$ together with the nitrogen atom to which they are attached represent a 5-or 6-membered ring optionally containing 1 or 2 additional heteroatoms selected from N, O or $S(O)_m$ in which ring any nitrogen atom present may optionally be substituted with a $C_{1-4}$ alkyl group, and which ring may optionally bear one or two oxo or thioxo substituents;

$M^5$ represents the group $NR^{14}R^{15}$, wherein $R^{14}$ and $R^{15}$ are as defined above, or $M^5$ represents the group

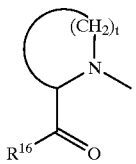

in which t represents 2 to 4 and $R^{16}$ represents OH, $OC_{1-4}$ alkyl or $NR^{14}R^{15}$; and $M^6$ represents a $C_{3-6}$ cycloalkyl group, the group $NR^{14}R^{15}$, wherein $R^{14}$ and $R^{15}$ are as defined above, or a 5- or 6-membered heterocyclic ring system containing 1 to 4 heteroatoms selected from N, O or S;

and p is 0 to 3; or when p is 2 or 3, two adjacent $R^3$ groups together form an optionally substituted methylenedioxy or ethylenedioxy group;

$R^2$ is selected from the group comprising hydrogen, halogen, trifluoromethyl, $C_{1-4}$ alkyl and $C_{1-4}$ alkoxy;

U represents phenyl or a 5 to 10-membered mono or bicyclic ring system in which one or more of the carbon atoms is optionally replaced by a heteroatom independently selected from N, O and $S(O)_m$, wherein m is 0, 1 or 2, and wherein U is substituted by at least one independently selected $R^6$ group and is optionally substituted by at least one independently selected $R^4$ group;

each $R^4$ is independently hydrogen, hydroxy, halogen, $C_{1-4}$ alkyl, $C_{1-4}$ alkoxy, $C_{1-4}$ alkylamino, di-[$C_{1-4}$ alkyl] amino, $C_{1-4}$ alkylthio, $C_{1-4}$ alkylsulphinyl, $C_{1-4}$ alkylsulphonyl, $C_{1-4}$ alkylcarbonyl, $C_{1-4}$ alkylcarbamoyl, di-[$C_{1-4}$ alkyl]carbamoyl, carbamyl, $C_{1-4}$ alkoxycarbonyl, cyano, nitro or trifluoromethyl;

each $R^6$ is independently a group $ZR^7$ wherein Z is joined to $R^7$ through a $(CH_2)p$ group in which p is 0, 1 or 2 and Z represents a group $V(CH_2)$, $V(CF_2)$, $(CH_2)V$, $(CF_2)V$, $V(CRR')$, $V(CHR)$ or V where R and R' are each $C_{1-4}$ alkyl and in which V is a hydrocarbyl group containing 0, 1 or 2 carbon atoms, carbonyl, dicarbonyl, CH(OH), CH(CN), sulphonamide, amide, O, $S(O)_m$ or $NR^b$ where $R^b$ is hydrogen or $R^b$ is $C_{1-4}$ alkyl; and $R^7$ is an optionally substituted $C_{3-6}$ cycloalkyl; or an optionally substituted 5, 6, 7, 8, 9 or 10-membered carbocyclic or heterocyclic moiety;

or $R^6$ is a group $ZR^7$ in which Z is $NR^b$, and $NR^b$ and $R^7$ together form an optionally substituted 5, 6, 7, 8, 9 or 10-membered carbocyclic or heterocyclic moiety.

Solvates of the compounds of formula (I) are also included within the scope of the present invention.

Heterocyclic groups comprise one or more rings which may be saturated, unsaturated, or aromatic and which may independently contain one or more heteroatoms in each ring.

Carbocyclic groups comprise one or more rings which may be independently saturated, unsaturated, or aromatic and which contain only carbon and hydrogen.

Suitably the 5, 6, 7, 8, 9 or 10-membered heterocyclic moiety is selected from the group comprising: furan, dioxolane, thiophene, pyrrole, imidazole, pyrrolidine, pyran, pyridine, pyrimidine, morpholine, piperidine, oxazole, isoxazole, oxazoline, oxazolidine, thiazole, isothiazole, thiadiazole, benzofuran, indole, isoindole, quinazoline, quinoline, isoquinoline and ketal.

Suitably the 5, 6, 7, 8, 9 or 10-membered carbocyclic moiety is selected from the group comprising: phenyl, benzyl, indene, naphthalene, tetralin, decalin, cyclopentyl, cyclopentenyl, cyclohexyl, cyclohexenyl and cycloheptyl.

By halo is meant fluoro, chloro, bromo or iodo.

Alkyl groups containing three or more carbon atoms may be straight, branched or cyclised.

In an embodiment $R^3$ is as defined above with the exception of wherein any substituent containing a heterocyclic ring bears one or two oxo or thioxo substituents on said ring, and with the exception of $C_{1-4}$ alkylsulphinyl-$C_{1-4}$ alkyl or $C_{1-4}$ alkylsulphonyl-$C_{1-4}$ alkyl; and $R^{14}$ and $R^{15}$ are as defined above with the exception of wherein they together with the nitrogen atom to which they are attached represent a 5- or 6-membered ring and said ring bears one or two oxo or thioxo substituents; save that $R^3$ may represent 4-pyridon-1-yl, 4-pyridon-1-yl-$C_{1-4}$ alkyl, 4-pyridon-1-yl-$C_{2-4}$ alkoxy, 4-pyridon-1-yl-$C_{2-4}$ alkylamino, 2-oxopyrrolidin-1-yl or 2,5-dioxopyrrolidin-1-yl.

In an embodiment, X is N.

In a further embodiment, Y is $NR^b$, $NR^b(CH_2)$, or $(CH_2)NR^b$, preferably Y is $NR^b$ and $R^b$ is preferably hydrogen or methyl.

In a further embodiment $R^1$ is a phenyl group or a 5- or 6-membered heterocyclic ring as defined above substituted with an $R^3$ group as defined above; and p=0.

In a preferred embodiment $R^1$ is a 5- or 6-membered heterocyclic ring as defined above substituted by one or more $R^3$ groups selected from the group comprising amino, hydrogen, halogen, hydroxy, formyl, carboxy, cyano, nitro, $C_{1-8}$ alkyl, $C_{1-8}$ alkoxy, $C_{1-8}$ alkylthio, $C_{1-8}$ alkylsulphinyl, $C_{1-8}$ alkylsulphonyl, $C_{1-4}$ alkylamino, $C_{1-4}$ dialkylamino, dioxolanyl, hydroxy-$C_{1-4}$ alkyl or hydroxy-$C_{1-4}$ alkanoyl-($C_{1-4}$ alkyl)-amino.

In a further preferred embodiment $R^1$ is a 5- or 6-membered heterocyclic ring as defined above substituted by one or more $R^3$ groups selected from the group comprising $C_{1-4}$alkyl, $C_{1-4}$alkylamino-$C_{1-4}$alkyl, di($C_{1-4}$alkyl) amino-$C_{1-4}$ alkyl, formyl, carboxy, $C_{1-4}$alkoxycarbonyl, dioxolanyl or trifluoromethyl.

In a further preferred embodiment $R^1$ is a 5- or 6-membered heterocyclic ring as defined above substituted by one or more $R^3$ groups selected from the group $C_{1-4}$alkylsulphinyl-$C_{1-4}$alkyl or $C_{1-4}$alkylsulphonyl-$C_{1-4}$ alkyl.

In a further preferred embodiment $R^1$ is a 5- or 6-membered heterocyclic ring as defined above substituted with an $R^3$ group selected from $M^1$-$M^2$-$M^3$-$M^4$, $M^1$-$M^5$ or $M^1$-$M^2$-$M^{3'}$-$M^6$ as defined above; and p=0.

In a further preferred embodiment $R^1$ is a 5- or 6-membered heterocyclic ring as defined above substituted with an $R^3$ group selected from piperidonyl-methyl, pyrrolidinonyl-methyl or dioxoimidazolidinyl-methyl.

In a further embodiment the group $M^2$-$M^3$-$M^4$ represents an α-, β- or γ-amino carboxylic, sulphinic or sulphonic acid or a $C_{1-4}$ alkyl ester, an amide or a $C_{1-4}$ alkyl- or di-($C_{1-4}$ alkyl)-amide thereof.

Preferably $M^1$ represents $CH_2$, $CO$, $CH_2CH_2$ or $CH_2CO$, more preferably $CH_2$.

Preferably $M^2$ represents $NR^{12}$ in which $R^{12}$ is as defined above; more preferably $R^{12}$ represents H or methyl.

Preferably $M^3$ represents $CH_2$, $CH_2CH_2$ or propyl.

Preferably $M^{3'}$ represents $CH_2$, ethyl, propyl, isopropyl or is absent.

Preferably $M^4$ represents $SOR^{13}$, $SO_2R^{13}$, $NR^{12}SO_2R^{13}$, $SO_2NR^{14}R^{15}$, $CO_2R^{13}$ or $CONR^{14}R^{15}$ in which $R^{12}$ and $R^{13}$ are defined above and $R^{14}$ and $R^{15}$ each independently represent H or $C_{1-4}$ alkyl; more preferably $R^{12}$, $R^{13}$, $R^{14}$ and $R^{15}$ each independently represent H or methyl.

Preferably $M^5$ represents a group $NR^{14}R^{15}$ in which $R^{14}$ and $R^{15}$ together with the nitrogen atom to which they are attached represent a 6-membered ring optionally containing an additional heteroatom selected from N or O, in which ring any nitrogen atom present may optionally be substituted with a $C_{1-4}$ alkyl group, preferably a methyl group; or $M^5$ represents a group

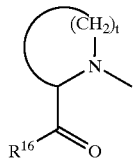

in which t represents 2 or 3 and $R^{16}$ represents OH, $NH_2$, $N(C_{1-4}$ alkyl$)_2$ or $OC_{1-4}$ alkyl; more preferably $R^{16}$ represents $NH_2$ or $N(CH_3)_2$.

Preferably $M^5$ also represents a group $NR^{14}R^{15}$ in which $R^{14}$ and $R^{15}$ together with the nitrogen atom to which they are attached represent a 5- or 6-membered ring optionally containing an additional heteroatom selected from N or O, in which ring any nitrogen atom present may optionally be substituted with a $C_{1-4}$ alkyl group, preferably a methyl group, and which ring also bears one or two oxo substituents.

Preferably $M^6$ represents a group $NR^{14}R^{15}$ in which $R^{14}$ and $R^{15}$ each independently represent $C_{1-4}$ alkyl, more preferably methyl, or $R^{14}$ and $R^{15}$ together with the nitrogen atom to which they are attached represent a 5- or 6-membered ring optionally containing an additional heteroatom selected from N or O, in which ring any nitrogen atom present may optionally be substituted with a $C_{1-4}$ alkyl group, preferably a methyl group; or $M^6$ represents a 5- or 6-membered heterocyclic ring system containing 1 or 2 heteroatoms selected from N or O.

In a further preferred embodiment $M^2$-$M^3$-$M^4$ represents an α-amino carboxylic acid or a methyl ester or amide thereof.

In a further preferred embodiment $M^2$-$M^3$-$M^4$ represents an α-, β- or γ-amino sulphinic or sulphonic acid, more preferably a β- or γ-amino sulphinic or sulphonic acid, most preferably a β-aminosulphonic acid, or a methyl ester thereof.

In an especially preferred embodiment $M^2$-$M^3$-$M^4$ represents a methylsulphonylethylamino, methylsulphinylethylamino, methylsulphonylethyl (methylamino), methylsulphinylethyl(methylamino), methylsulphonylpropylamino, methylsulphinylpropylamino, methylsulphonamidoethylamino, aminosulphonylethylamino, methylaminosulphonylethylamino, sarcosinamide, glycine, glycinamide, glycine methyl ester or acetylaminoethylamino group.

In a further especially preferred embodiment $M^5$ represents a piperazinyl, methylpiperazinyl, piperidinyl, pyridyl, prolinamido or N,N-dimethylprolinamido group.

In a further especially preferred embodiment $M^5$ represents a piperidonyl, pyrrolidinonyl or dioxoimidazolidinyl group.

In a further especially preferred embodiment $M^5$ represents an isopropylamino or N-morpholinyl group.

In a further especially preferred embodiment $M^1$-$M^5$ represents an isopropylacetamido or N-morpholinoacetamido group.

In a further especially preferred embodiment $M^1$-$M^5$ represents a piperidonyl-methyl, pyrrolidinonyl-methyl or dioxoimidazolidinyl-methyl group.

In a further especially preferred embodiment $M^2$-$M^{3'}$-$M^6$ represents a pyridylamino, cyclopropylamino, N-(piperidin-4-yl)-N-methylamino, N,N-dimethylaminoprop-2-ylamino, N-(2-dimethylaminoethyl)-N-ethylamino or tetrahydrofuranomethylamino group, preferably a pyridylamino group.

In an embodiment $R^1$ may be selected from the group comprising phenyl, furan, thiophene, pyridine, pyrimidine, pyrazine, pyrrole, oxazole, isoxazole, oxadiazole, thiazole, isothiazole, triazole, tetrazole and imidazole or a hydrogenated derivative of any of the aforementioned.

In a further preferred embodiment $R^1$ may be selected from the group comprising furan, dihydrofuran, thiophene, imidazole, tetrazole, triazole, pyridine, pyrrole, pyrimidine, isoxazole or oxadiazole.

In a further preferred embodiment $R^1$ is an oxadiazolidinone ring.

In an especially preferred embodiment $R^1$ is selected from the group comprising furan, imidazole, oxadiazole (particularly 1,3,4-oxadiazole and 1,2,4-oxadiazole) and triazole (particularly 1,2,3-triazole and 1,3,4-triazole).

In an embodiment $R^2$ is hydrogen, $C_{1-4}$ alkyl, $C_{1-4}$ alkoxy or halogen, preferably methyl or hydrogen, more preferably hydrogen.

In a further embodiment $R^4$ is hydrogen, hydroxy, halogen, $C_{1-4}$ alkyl, $C_{1-4}$ alkoxy, di-[$C_{1-4}$ alkyl]amino, nitro or trifluoromethyl, preferably hydrogen, halogen or methyl, more preferably hydrogen.

In a preferred embodiment $R^7$ is an optionally substituted phenyl, dioxolanyl, thienyl, cyclohexyl or pyridyl group.

In a further embodiment, Z is absent or represents oxygen, $CH_2$, $NR^b$, $NR^b(CH_2)$, $(CH_2)NR^b$, $CH(CH_3)$, $O(CH_2)$, $(CH)CN$, $O(CF_2)$, $(CH_2)O$, $(CF_2)O$, $S(CH_2)$, $S(O)_m$, carbonyl or dicarbonyl, wherein $R^b$ is hydrogen or $C_{1-4}$ alkyl.

In a preferred embodiment Z is oxygen, dicarbonyl, $OCH_2$, $CH_2(CN)$, $S(O)_m$ or $NR^b$, wherein $R^b$ is hydrogen or $C_{1-4}$ alkyl.

In a further preferred embodiment $R^6$ is benzyl, halo-, dihalo- and trihalobenzyl, α-methylbenzyl, phenyl, halo-, dihalo- and trihalophenyl, pyridyl, pyridylmethyl, pyridyloxy, pyridylmethoxy, thienylmethoxy, dioxolanylmethoxy, cyclohexylmethoxy, phenoxy, halo-, dihalo- and trihalophenoxy, phenylthio, benzyloxy, halo-, dihalo- and trihalobenzyloxy, $C_{1-4}$ alkoxybenzyloxy, phenyloxalyl or benzenesulphonyl, more preferably benzyl, fluorobenzyl, difluorobenzyl, benzyloxy, fluorobenzyloxy, pyridylmethyl, phenyl, benzenesulphonyl, phenoxy or fluorophenoxy.

In a further embodiment $R^6$ is in the para position with respect to Y.

When the group Z is absent, $R^6=R^7$.

One or both of the rings comprising the mono or bicyclic ring system U may be aromatic or non-aromatic. The $R^4$ and $R^6$ groups may be bound to the ring system by either a carbon atom or a heteroatom of the ring system. The ring system itself may be bound to the bridging group by a carbon atom or a heteroatom. The $R^4$ and $R^6$ groups may be bound to either ring when U represents a bicyclic ring system, but these groups are preferably bound to the ring which is not bound to the bridging group Y in such a case.

Examples of suitable mono or bicyclic groups U include: phenyl, isoindenyl, indenyl, indanyl, naphthyl, 1,2-dihydronaphthyl or 1,2,3,4-tetrahydronaphthyl, pyrrolyl, pyridinyl, pyridazinyl, pyrimidinyl, pyrazinyl, furanyl, 2H-pyranyl, thiophenyl, 1H-azepinyl, oxepinyl, thiepinyl, azocinyl, 2H-oxocinyl, thieno[2,3-b]furanyl, thianaphthenyl, indolyl, indolinyl, isoindolyl, isoindolinyl, indolizinyl, 1H-benzimidazolyl, 2,3-dihydro-1H-benzimidazolyl, 1H-indazolyl, 2,3-dihydro-1H-indazolyl, benzoxazolyl, 2,3-dihydrobenzoxazolyl, benzo[c]isoxazolyl, benzo[d]isoxazolyl, 2,3-dihydrobenzo[d]isoxazolyl, benzothiazoyl, 2,3-dihydrobenzothiazolyl, benzo[c]isothiazolyl, benzo[d]isothiazolyl, 2,3-dihydrobenzo[d]isothiazolyl, 1H-benzotriazolyl, benzo[c]furanyl, benzo[c][1,2,3]thiadiazolyl, benzo[d][1,2,3]oxadiazolyl, benzo[d][1,2,3]thia-diazolyl, quinolyl, 1,2-dihydroquinolinyl, 1,2,3,4-tetrahydroquinolinyl, isoquinolyl 1,2,3,4-tetrahydroisoquinolinyl, cinnolinyl, quinazolinyl, quinoxalinyl, phthalazinyl, 4H-1,4-benzoxazinyl, 2,3-dihydro-4H-1,4-benzoxazinyl, 4H-1,4-benzothiazinyl or 2,3-dihydro-4H-1,4-benzothiazinyl.

Suitably U represents a phenyl, indolyl, isoindolyl, indolinyl, isoindolinyl, 1H-indazolyl, 2,3-dihydro-1H-indazolyl, 1H-benzimidazolyl, 2,3-dihydro-1H-benzimidazolyl or 1H-benzotriazolyl group.

In an embodiment, the optional substituents for the carbocyclic or heterocyclic moiety, which may be present at any available position of said moiety, are selected from the group comprising:

$(CH_2)_qS(O)_m$-$C_{1-4}$alkyl, $(CH_2)_qS(O)_m$—$C_{3-6}$cycloalkyl, $(CH_2)_qSO_2NR^8R^9$, $(CH_2)_qNR^8R^9$, $(CH_2)_qCO_2R^8$, $(CH_2)_qOR^8$, $(CH_2)_qCONR^8R^9$, $(CH_2)_qNR^8COR^9$, $(CH_2)_qCOR^8$, $(CH_2)_qR^8$, $NR^8SO_2R^9$ and $S(O)_mR_8$, wherein q is an integer from 0 to 4 inclusive; m is 0, 1 or 2;

$R^8$ and $R^9$ are independently selected from the group comprising hydrogen, $C_{1-4}$ alkyl, $C_{3-6}$ cycloalkyl, aryl, a 5- or 6-membered saturated or unsaturated heterocyclic ring which may be the same or different and which contains one or more heteroatoms which are selected from N, O or $S(O)_m$, with the proviso that the heterocyclic ring does not contain two adjacent O or $S(O)_m$ atoms.

In a further embodiment the optional substituents for the carbocyclic or heterocyclic moiety are selected from the group comprising morpholine, piperazine, piperidine, pyrrolidine, tetrahydrofuran, dioxolane, oxothiolane and oxides thereof, dithiolane and oxides thereof, dioxane, pyridine, pyrimidine, pyrazine, pyridazine, furan, thiofuran, pyrrole, triazine, imidazole, triazole, tetrazole, pyrazole, oxazole, oxadiazole and thiadiazole.

Other optional substituents for the carbocyclic or heterocyclic moiety and also for other optionally substituted groups include, but are not limited to, hydroxy, halogen, trifluoromethyl, trifluoromethoxy, nitro, amino, cyano, $C_{1-4}$ alkoxy, $C_{1-4}$ alkylthio, $C_{1-4}$ alkyl carbonyl, carboxylate and $C_{1-4}$ alkoxy carboxyl.

In a further embodiment X represents N; p is 0; and the group $R^1$ is in the 6-position of the quinazoline ring system.

In a preferred embodiment of the present invention there is provided a compound of formula (I) or a salt or solvate thereof wherein X represents N; Y represents $NR^a$, wherein $R^a$ is hydrogen or $C_{1-4}$ alkyl; $R^1$ represents furan, thiophene, pyrrole, pyridine, pyrimidine, pyrazine, imidazole, oxazole, isoxazole, oxadiazole, tetrazole, triazole, dioxolane or a partially or fully hydrogenated derivative of any of these groups, optionally substituted by one or more $R^3$ groups selected from halo, trifluoromethyl, $C_{1-4}$ alkyl, carboxy, $C_{1-4}$-alkoxycarbonyl, formyl, hydroxy-$C_{1-4}$ alkyl, 1,3-dioxolan-2-yl, amino, $C_{1-4}$ alkylamino, di($C_{1-4}$ alkyl)amino, hydroxy-$C_{1-4}$alkanoyl-($C_{1-4}$alkyl)-amino, $C_{1-4}$ alkylamino-$C_{1-4}$ alkyl or di($C_{1-4}$ alkyl)amino-$C_{1-4}$ alkyl; p is 0; $R^2$ represents hydrogen; $R^4$ represents hydrogen, halo or methyl; U represents phenyl, indolyl, benzimidazolyl or indazolyl, more preferably phenyl or indazolyl; and $R^6$ represents phenyl, benzyl, α-methylbenzyl, fluorobenzyl, difluorobenzyl, pyridylmethyl, benzenesulphonyl, phenoxy, fluorophenoxy, benzyloxy or fluorobenzyloxy.

In a further preferred embodiment of the present invention there is provided a compound of formula (I) or a salt or solvate thereof wherein X represents N; Y represents $NR^a$, wherein $R^a$ is hydrogen or $C_{1-4}$ alkyl; $R^1$ represents furan, thiophene, pyrrole, pyridine, pyrimidine, pyrazine, imidazole, oxazole, isoxazole, oxadiazole, tetrazole, triazole, dioxolane or a partially or fully hydrogenated derivative of any of these groups substituted by a $C_{1-4}$alkylsulphinyl-$C_{1-4}$alkyl or $C_{1-4}$alkylsulphonyl-$C_{1-4}$ alkyl group; p is 0; $R^2$ represents hydrogen; $R^4$ represents hydrogen, halo or methyl; U represents phenyl, indolyl, benzimidazolyl or indazolyl, more preferably phenyl or indazolyl; and $R^6$ represents phenyl, benzyl, α-methylbenzyl, fluorobenzyl, difluorobenzyl, pyridylmethyl, benzenesulphonyl, phenoxy, fluorophenoxy, benzyloxy or fluorobenzyloxy.

In further preferred embodiment of the present invention there is provided a compound of formula (I) or a salt or solvate thereof wherein X represents N; Y represents $NR^a$, wherein $R^a$ is hydrogen or $C_{1-4}$ alkyl; $R^1$ represents furan, thiophene, pyrrole, pyridine, pyrimidine, pyrazine, imidazole, oxazole, isoxazole, oxadiazole, tetrazole, triazole, dioxolane or a partially or fully hydrogenated derivative of any of these groups, optionally substituted with an $R^3$ group selected from methylsulphonylethylaminomethyl, methylsulphonylethylamino-carbonyl, methylsulphinylethylamino-methyl, methylsulphinylethylamino-carbonyl, methylsulphonylpropylamino-methyl, methylsulphinylpropylamino-methyl, methylsulphonylpropyamino-carbonyl, methylsulphinylpropylamino-carbonyl, methylsulphonylethyl-(methylamino)-methyl, methylsulphonylethyl-(methylamino)-carbonyl, methylsulphinylethyl-(methylamino)-methyl, methylsulphinylethyl-(methylamino)-carbonyl, methylsulphonylpropyl-(methylamino)-methyl, methylsulphinylpropyl-(methylamino)-methyl, methylsulphonylpropyl-(methylamino)-carbonyl, methylsulphinylpropyl-(methylamino)-carbonyl, methylsulphonamidoethylamino-methyl, methylsulphonamidopropylamino-methyl, aminosulphonylethylaminomethyl, methylaminosulphonylethylaminomethyl, sarcosinamidomethyl, glycinylmethyl, glycinamidomethyl, glycinylmethyl methyl ester, acetylaminoethylaminomethyl, piperazinylmethyl, methylpiperazinylmethyl, piperidinylmethyl, pyridylmethyl, N-(prolinamido)methyl, (N,N-dimethyl-prolinamido)methyl, pyridylaminomethyl, cyclopropylaminomethyl, N-(piperidin-4-yl)-N-methylaminomethyl, N,N-dimethylaminoprop-2-ylaminomethyl, N-(2-dimethylaminoethyl)-N-ethylaminomethyl, isopropylacetamido, N-morpholinylacetamido or tetrahydrofuranomethylaminomethyl and optionally further substituted by one or more $C_{1-4}$ alkyl groups; p is 0; $R^2$ represents hydrogen; $R^4$ represents hydrogen, halo or methyl; U represents phenyl, indolyl, benzimidazolyl or indazolyl, more preferably phenyl or indazolyl; and $R^6$ represents phenyl, benzyl, α-methylbenzyl, fluorobenzyl, difluorobenzyl, pyridylmethyl, benzenesulphonyl, phenoxy, fluorophenoxy, benzyloxy or fluorobenzyloxy.

In further preferred embodiment of the present invention there is provided a compound of formula (I) or a salt or solvate thereof wherein X represents N; Y represents $NR^a$, wherein $R^a$ is hydrogen or $C_{1-4}$ alkyl; $R^1$ represents furan, thiophene, pyrrole, pyridine, pyrimidine, pyrazine, imidazole, oxazole, isoxazole, oxadiazole, tetrazole, triazole, dioxolane or a partially or fully hydrogenated derivative of any of these groups, substituted with an $R^3$ group selected from piperidonyl-methyl, pyrrolidinonyl-methyl or dioxoimidazolidinyl-methyl; p is 0; $R^2$ represents hydrogen; $R^4$ represents hydrogen, halo or methyl; U represents phenyl, indolyl, benzimidazolyl or indazolyl, more preferably phenyl or indazolyl; and $R^6$ represents phenyl, benzyl, α-methylbenzyl, fluorobenzyl, difluorobenzyl, pyridylmethyl, benzenesulphonyl, phenoxy, fluorophenoxy, benzyloxy or fluorobenzyloxy.

In an especially preferred embodiment of the present invention there is provided a compound of formula (I) or a salt or solvate thereof wherein X represents N; Y represents $NR^a$, wherein $R^a$ is hydrogen or $C_{1-4}$ alkyl; $R^1$ represents a furan, dihydrofuran, thiophene, pyridine, pyrrole, pyrimidine, isoxazole, triazole, tetrazole, imidazole or oxadiazole ring, preferably furan, imidazole, oxadiazole and triazole, substituted with an $R^3$ group selected from $C_{1-4}$alkyl, $C_{1-4}$alkylamino-$C_{1-4}$alkyl, di($C_{1-4}$alkyl)amino-$C_{1-4}$ alkyl, formyl, carboxy, $C_{1-4}$alkoxycarbonyl, dioxolanyl, trifluoromethyl, methylsulphonylethylaminomethyl, methylsulphonylethylamino-carbonyl, methylsulphonylethyl(methylamino)-methyl, methylsulphonamidoethylamino-methyl, aminosulphonylethylamino-methyl, methylaminosulphonylethylamino-methyl, N,N-dimethylaminoprop-2-ylaminomethyl, N-(2-dimethylaminoethyl)-N-ethylaminomethyl, pyridylaminomethyl, tetrahydrofuranomethylaminomethyl, piperazinylmethyl, methylpiperazinylmethyl, piperidinylmethyl, pyridylmethyl, N-(prolinamido)methyl or (N,N-dimethyl-prolinamido)methyl; p is 0; $R^2$ represents hydrogen; $R^4$ represents hydrogen or halo; U represents phenyl or indazolyl; and $R^6$ represents benzyl, fluorobenzyl, difluorobenzyl, pyridylmethyl, benzenesulphonyl, phenoxy, benzyloxy or fluorobenzyloxy.

In a further especially preferred embodiment of the present invention there is provided a compound of formula (I) or a salt or solvate thereof wherein X represents N; Y represents $NR^a$, wherein $R^a$ is hydrogen or $C_{1-4}$ alkyl; $R^1$ represents a furan, dihydrofuran, thiophene, pyridine, pyrrole, pyrimidine, isoxazole, triazole, tetrazole, imidazole or oxadiazole ring, preferably furan, imidazole, oxadiazole and triazole, substituted with an $R^3$ group selected from a $C_{1-4}$alkylsulphinyl-$C_{1-4}$alkyl, $C_{1-4}$alkylsulphonyl-$C_{1-4}$alkyl, piperidonyl-methyl, pyrrolidinonyl-methyl or dioxoimidazolidinyl-methyl group; p is 0; $R^2$ represents hydrogen; $R^4$ represents hydrogen or halo; U represents phenyl or indazolyl; and $R^6$ represents benzyl, fluorobenzyl, difluorobenzyl, pyridylmethyl, benzenesulphonyl, phenoxy, benzyloxy or fluorobenzyloxy.

In a most especially preferred embodiment of the present invention there is provided a compound of formula (I) or a salt or solvate thereof wherein X represents N; Y represents NH; $R^1$ represents a furan, imidazole, oxadiazole or triazole ring optionally substituted with a methyl group; p is 0; $R^2$ represents hydrogen; $R^4$ represents hydrogen; U represents phenyl or indazolyl; and $R^6$ represents benzyl, fluorobenzyl, benzyloxy or fluorobenzyloxy.

In a further most especially preferred embodiment of the present invention there is provided a compound of formula (I) or a salt or solvate thereof wherein X represents N; Y represents NH; $R^1$ represents a furan ring substituted with an $R^3$ group selected from methylsulphonylethylaminomethyl, methylsulphonylethyl(methylamino)-methyl, methylsulphonamidoethylamino-methyl, aminosulphonylethylamino-methyl, methylaminosulphonylethylamino-methyl, methylpiperazinylmethyl or (prolinamido)methyl; p is 0; $R^2$ represents hydrogen; $R^4$ represents hydrogen; U represents phenyl or indazolyl; and $R^6$ represents benzyl, fluorobenzyl, benzyloxy or fluorobenzyloxy.

In a further most especially preferred embodiment of the present invention there is provided a compound of formula (I) or a salt or solvate thereof wherein X represents N; Y represents NH; $R^1$ represents an oxadiazole ring substituted with an $R^3$ group selected from piperidonyl-methyl or pyrrolidinonyl-methyl; p is 0; $R^2$ represents hydrogen; $R^4$ represents hydrogen; U represents phenyl or indazolyl; and $R^6$ represents benzyl, fluorobenzyl, benzyloxy or fluorobenzyloxy.

Preferred compounds of the present invention include:
(4-Benzyloxy-phenyl)-(6-furan-2-yl-quinazolin-4-yl)-amine;
(4-Benzyloxy-phenyl)-(6-(thiophen-2-yl)-quinazolin-4-yl)-amine;
(4-Benzyloxy-phenyl)-(6-(pyridin-2-yl)-quinazolin-4-yl)-amine;
(4-Benzyloxy-phenyl)-(6-(pyrimidin-2-yl)-quinazolin-4-yl)-amine;
(4-Benzyloxy-phenyl)-(6-(5-(1,3-dioxolan-2-yl)-furan-2-yl-quinazolin-4-yl)-amine;
(4-Benzyloxy-phenyl)-(6-(3-methyl-3H-imidazol-4-yl)-quinazolin-4-yl)-amine;
(4-Benzyloxy-phenyl)-(6-(2,3-dihydrofuran-5-yl)-quinazolin-4-yl)-amine;
(4-Benzyloxy-phenyl)-(6-(3-methyl-1,2,3-triazol-4-yl)-quinazolin-4-yl)-amine;
5-(4-(4-Benzyloxy-phenylamino)-quinazolin-6-yl)-furan-2-carbaldehyde;
(4-Benzyloxy-phenyl)-(6-(5-(4-methylpiperazin-1-ylmethyl)-furan-2-yl)-quinazolin-4-yl)-amine;
(S)-1-(5-(4-(4-Benzyloxy-phenylamino)-quinazolin-6-yl)-furan-2-ylmethyl)-pyrrolidine-2-carboxylic acid amide;
N2-(5-(4-(4-Benzyloxy-phenylamino)-quinazolin-6-yl)-furan-2-ylmethyl)-N1,N1-dimethyl-propane-1,2-diamine;
N-(5-(4-(4-Benzyloxy-phenylamino)-quinazolin-6-yl)-furan-2-ylmethyl)-N-ethyl-N',N'-dimethyl-ethane-1,2-diamine;
(4-Benzyloxy-phenyl)-(6-(5-(pyridin-3-ylaminomethyl)-furan-2-yl)quinazolin-4-yl)-amine;

(4-Benzyloxy-phenyl)-(6-(5-(((tetrahydro-furan-2-ylmethyl)-amino)-methyl)-furan-2-yl)-quinazolin-4-yl)-amine;
(1-Benzyl-1H-indazol-5-yl)-(6-(5-(1,3)-dioxolan-2-yl-furan-2-yl)-quinazolin-4-yl)-amine;
5-(4-(1-Benzyl-1H-indazol-5-ylamino)-quinazolin-6-yl)-furan-2-carbaldehyde;
(S)-1-(5-(4-(1-Benzyl-1H-indazol-5-ylamino)-quinazolin-6-yl)-furan-2-ylmethyl)-pyrrolidine-2-carboxylic acid amide;
(1-Benzyl-1H-indazol-5-yl)-(6-(5-((2-methanesulphonyl-ethylamino)-methyl)-furan-2-yl)-quinazolin-4-yl)-amine;
(4-Phenoxy-phenyl)-(6-(5-methyl-1,3,4-oxadiazol-2-yl)quinazolin-4-yl)-amine;
(1-(2-Fluorobenzyl)-1H-indazol-5-yl)-(6-(5-methyl-1,3,4-oxadiazol-2-yl)-quinazolin-4-yl)-amine;
(1-(3-Fluorobenzyl)-1H-indazol-5-yl)-(6-(5-methyl-1,3,4-oxadiazol-2-yl)-quinazolin-4-yl)-amine;
(1-Pyridin-2-ylmethyl)-1H-indazol-5-yl)-(6-(5-methyl-1,3,4-oxadiazol-2-yl)-quinazolin-4-yl)-amine;
(1-(2,3-Difluorobenzyl)-1H-indazol-5-yl)-(6-(5-methyl-1,3,4-oxadiazol-2-yl)quinazolin-4-yl)-amine;
(3-Chloro-4-(2-fluoro-benzyloxy)-phenyl)-(6-(5-methyl-1,3,4-oxadiazol-2-yl)-quinazolin-4-yl)-amine;
(3-Chloro-4-(3-fluoro-benzyloxy)-phenyl)-(6-(5-methyl-1,3,4-oxadiazol-2-yl)-quinazolin-4-yl)-amine;
(4-Benzyloxy-phenyl)-(6-(5-methyl-1,3,4-oxadiazol-2-yl)-quinazolin-4-yl)-amine;
(4-(2-Fluoro-benzyloxy)-phenyl)-(6-(5-methyl-1,3,4-oxadiazol-2-yl)-quinazolin-4-yl)-amine;
(4-(3-Fluoro-benzyloxy)-phenyl)-(6-(5-methyl-1,3,4-oxadiazol-2-yl)-quinazolinyl)-amine;
(4-Benzenesulphonyl-phenyl)-(6-(5-methyl-1,3,4-oxadiazol-2-yl)-quinazolin-4-yl)-amine;
(1-(3,5-Difluoro-benzyl)-1H-indazol-5-yl)-(6-(5-methyl-1,3,4-oxadiazol-2-yl)-quinazolin-4-yl)-amine
(4-(4-Fluoro-benzyloxy)-phenyl)-(6-(5-methyl-1,3,4-oxadiazol-2-yl)-quinazolin-4-yl)-amine;
(4-(2-Fluoro-benzyloxy)-phenyl)-(6-(5-trifluoromethyl-1,3,4-oxadiazol-2-yl)-quinazolin-4-yl)-amine;
(4-(3-Fluorobenzyloxy)-phenyl)-(6-(5-trifluoromethyl-1,3,4-oxadiazol-2-yl)-quinazolin-4-yl)-amine;
(4-(4-Fluoro-benzyloxy)-phenyl)-(6-(5-trifluoromethyl-1,3,4-oxadiazol-2-yl)-quinazolin-4-yl)-amine;
(1-Benzyl-1H-indazol-5-yl)-(6-(5-trifluoromethyl-1,3,4-oxadiazol-2-yl)-quinazolin-4-yl)-amine;
(4-Pyridin-3-ylmethoxy)-phenyl)-(6-(5-trifluoromethyl-1,3,4-oxadiazol-2-yl)-quinazolin-4-yl)-amine;
(1-Benzyl-1H-indazol-5-yl)-(6-(3-methyl-3H-imidazol-4-yl)-quinazolin-4-yl)-amine;
(1-Benzyl-1H-indazol-5-yl)-(6-(1-methyl-1H-imidazol-2-yl)quinazolin-4-yl)-amine;
(4-Benzyloxy-phenyl)-(6-(1H-tetrazol-5-yl)-quinazolin-4-yl)-amine;
(1-Benzyl-1H-indazol-5-yl)-(6-(5-methyl-1,3,4-oxadiazol-2-yl)-quinazolin-4-yl0-amine;
(1-Benzyl-1H-indazol-5-yl)-(6-(5-methyl-1,3,4-triazol-2-yl)-quinazolin-4-yl)-amine;
(S)-1-(2-(4-(4-Benzyloxy-phenylamino)-quinazolin-6-yl)-3-methyl-3H-imidazol-4-ylmethyl)-pyrrolidine-2-carboxylic acid amide;

(1-Benzyl-1H-indazol-5-yl)-(6-(5-methanesulphonylmethyl-1,3,4-oxadiazol-2-yl)-quinazolin-4-yl)-amine;
(4-Benzyloxy-phenyl)-(6-(1-methylpyridinium-2-yl)quinazolin-4-yl)-amine; chloride;
(4-Benzyloxy-phenyl)-(6-(2,3-dimethyl-3H-imidazol-4-yl)-quinazolin-4-yl)-amine;
(4-Benzyloxy-phenyl)-(-6-(3-methylisoxazol-5-yl)-quinazolin-4-yl)-amine;
(4-Benzyloxy-phenyl)-(6-(5-(((2-methanesulphonyl-ethyl)-methyl-amino)-methyl)-furan-2-yl)-quinazolin-4-yl)-amine;
N-(2-((5-(4-(4-Benzyloxy-phenylamino)-quinazolin-6-yl)-furan-2-ylmethyl)-amino)-ethyl)-methanesulphonamide;
2-((5-(4-(4-Benzyloxy-phenylamino)-quinazolin-6-yl)-furan-2-ylmethyl)-amino)-ethanesulphonic acid amide;
5-(4-(4-Benzyloxy-phenylamino)-quinazolin-6-yl)-furan-2-carboxylic acid methyl ester;
5-(4-(4-Benzyloxy-phenylamino)-quinazolin-6-yl)-furan-2-carboxylic acid;
5-[4-(4-Benzyloxy-phenylamino)-quinazolin-6-yl]-furan-2-carboxylic acid (2-methanesulphonyl-ethyl)-amide;
2-((5-(4-(4-Benzyloxy-phenylamino)-quinazolin-6-yl)-furan-2-ylmethyl)-amino)-ethanesulphonic acid methylamide;
(1-Benzyl-1H-indazol-5-yl)-(6-(3-methyl-1,2,4-oxadiazol-5-yl)-quinazolin-4-yl)-amine;
(4-Benzyloxy-phenyl)-(6-(5-methyl-1,2,4-oxadiazol-3-yl)-quinazolin-4-yl)-amine;
(4-Benzyloxy-phenyl)-(6-(5-(2-dimethylamino-ethyl)-1,2,4-oxadiazol-3-yl)-quinazolin-4-yl)-amine;
(4-Benzyloxy-phenyl)-(6-(5-(dimethylaminomethyl)-1,2,4-oxadiazol-3-yl)-quinazolin-4-yl)-amine;
(1-Benzyl-1H-indazol-5-yl)-(6-(5-(((2-methanesulphonyl-ethyl)-amino)-methyl)-1,2,4-oxadiazol-3-yl)-quinazolin-4-yl)-amine;
(1-Benzyl-1H-indazol-5-yl)-(6-(5-methanesulphonylmethyl-1,2,4-oxadiazol-3-yl)-quinazolin-4-yl)-amine;
(1-Benzyl-1H-indazol-5-yl)-(6-(5-methyl-1,2,4-oxadiazol-3-yl)-quinazolin-4-yl0-amine;
(1-Benzyl-1H-indazol-5-yl)-6-(5-(pyridin-3-ylmethyl)-1,2,4-oxadiazol-3-yl)-quinazolin-4-yl)-amine;
(1-Benzyl-1H-indazol-5-yl)-(6-(1-methylpyrrol-2-yl)-quinazolin-4-yl)-amine;
5-(4-(1-Benzyl-1H-indazol-5-yl)-quinazolin-6-yl)-1-methyl-pyrrole-2-carbaldehyde;
1-(3-(4-(1-Benzyl-1H-indazol-5-ylamino)-quinazolin-6-yl)-1,2,4-oxadiazol-5-ylmethyl)-piperidin-4-one;
1-(3-(4-(1-Benzyl-1H-indazol-5-ylamino)-quinazolin-6-yl)-1,2,4-oxadiazol-5-ylmethyl)-pyrrolidin-2-one;
1-(3-(4-(1-Benzyl-1H-indazol-5-ylamino)-quinazolin-6-yl)-1,2,4-oxadiazol-5-ylmethyl)-imidazolidin-2,5-dione;
3-(4-(1-Benzyl-1H-indazol-5-ylamino)-quinazolin-6-yl)-4H-1,2,4-oxadiazolidin-3-one;
(1-Benzyl-1H-indazol-5-yl)-(6-(5-((2-methanesuphonyl-ethyl-amino)-methyl)-1-methyl-pyrrol-2-yl)-quinazolin-4-yl)-amine;
(4-Benzyloxy-phenyl)-(6-(1-(3-N,N-dimethylaminopropyl)-imidazol-5-yl)-quinazolin-4-yl)-amine;

(1-Benzyl-1H-indazolyl)-(6-(1-(3-N,N-dimethylaminopropyl)-imidazol-5-yl)-quinazolin-4-yl)-amine;

(4-Benzyloxy-phenyl)-(6-(1-(3-N,N-dimethylaminopropyl)-imidazol-2-yl)-quinazolin-4-yl)-amine;

(1-Benzyl-1H-indazolyl)-(6-(1-(3-N,N-dimethylaminopropyl)-imidazol-5-yl)-quinazolin-4-yl)-amine;

(4-Benzyloxy-phenyl)-(6-(5-trifluoromethyl-1,3,4-oxadiazol-2-yl)-quinazolin-4-yl)-amine;

(1-(2-Fluoro-benzyl)-1H-indazol-5-yl)-(6-(5-trifluoromethyl-1,3,4-oxadiazol-2-yl)-quinazolin-4-yl)-amine;

(1-(3-Fluoro-benzyl)-1H-indazol-5-yl)-(6-(5-trifluoromethyl-1,3,4-oxadiazol-2-yl)-quinazolin-4-yl)-amine;

(1-(4-Fluoro-benzyl)-1H-indazol-5-yl)-(6-(5-trifluoromethyl-1,3,4-oxadiazol-2-yl)-quinazolin-4-yl)-amine;

(1-Benzyl-1H-indazol-5-yl)-(7-(5-methyl-[1,3,4]oxadiazol-2-yl)-quinazolin-4-yl)-amine;

(1-Benzyl-1H-indazol-5-yl)-(7-(3-methyl-3H-imidazol-4-yl)quinazolin-4-yl)-amine;

(1-Benzyl-1H-indazol-5-yl)-[7-(furan-2-yl)-quinazolin-4-yl]-amine;

(1-Benzyl-1H-indazol-5-yl)-[7-(5-(1,3-dioxolan-2-yl)-furan-2-yl)quinazolin-4-yl]amine;

5-[4-(1-Benzyl-1H-indazol-5-ylamino)-quinazolin-7-yl]-furan-2-carbaldehyde;

(1-Benzyl-1H-indazol-5-yl)-[7-{5-[(2-methanesulphonyl-ethylamino)-methyl]-furan-2-yl}-quinazolin-4-yl]-amine;

(S)-1-{5-[4-(1-Benzyl-1H-indazol-5-ylamino)-quinazolin-7-yl]-furan-2-yl-methyl}-pyrrolidine-2-carboxylic acid amide;

(4-Benzyloxy-phenyl)-(6-(3-methyl-[1,2]oxazol-4-yl)-quinazolin-4-yl)-amine;

(4-Benzyloxy-phenyl)-(6-(4-(1,3-dioxolan-2-yl)-3-methyl-3H-imidazol-2-yl)-quinazolin-4-yl)-amine;

2-(4-(4-Benzyloxy-phenylamino)-quinazolin-6-yl)-3-methyl-3H-imidazol-4-carbaldehyde;

and salts or solvates thereof, particularly pharmaceutically acceptable salts or solvates thereof.

Other preferred compounds of the present invention include:

(4-Benzyloxy-phenyl)-(6-(imidazol-2-yl)-quinazolin-4-yl)-amine;

(4-Benzyloxy-phenyl)-(6-[5-(4-methyl-piperazinylmethyl)-1-methylimidazol-2-yl]-quinazolin-4-yl)-amine;

(4-Benzyloxy-phenyl)-(6-[5-(N,N-dimethylaminomethyl)-1-methylimidazol-2-yl]-quinazolin-4-yl)-amine;

(4-Benzyloxy-phenyl)-(6-[5-(4-methyl-piperazinylmethyl)-imidazol-2-yl]-quinazolin-4-yl)-amine;

(4-Benzyloxy-phenyl)-(6-[5-(N,N-dimethylaminomethyl)-imidazol-2-yl]-quinazolin-4-yl)-amine;

(4-Benzyloxy-phenyl)-(6-[1-(4-methyl-piperazinylmethyl)-imidazol-2-yl]-quinazolin-4-yl)-amine;

(4-Benzyloxy-phenyl)-(6-[1-(N,N-dimethylaminomethyl)-imidazol-2-yl]-quinazolin-4-yl)-amine;

(4-Benzyloxy-phenyl)-(6-(5-carboxymethylaminomethyl-furan-2-yl)-quinazolin-4-yl)-amine;

and salts or solvates thereof, particularly pharmaceutically acceptable salts or solvates thereof.

Particularly preferred compounds of the present invention include:

(4-Benzyloxy-phenyl)-(6-furan-2-yl-quinazolin-4-yl)-amine;

(4-Benzyloxy-phenyl)-(6-(3-methyl-3H-imidazol-4-yl)-quinazolin-4-yl)-amine;

(4-(4-Fluoro-benzyloxy)-phenyl)-(6-(5-methyl-1,3,4-oxadiazol-2-yl)quinazolin-4-yl)-amine;

(1-Benzyl-1H-indazol-5-yl)-(6-(5-methyl-1,3,4-triazol-2-yl)-quinazolin-4-yl)-amine;

(4-Benzyloxy-phenyl)-(6-(5-methyl-1,2,4-oxadiazol-3-yl)-quinazolin-4-yl)-amine;

and salts or solvates thereof, particularly pharmaceutically acceptable salts or solvates thereof.

Further particularly preferred compounds of the present invention include:

(4-Benzyloxy-phenyl)-(6-(5-(4-methylpiperazin-1-ylmethyl)-furan-2-yl)-quinazolin-4-yl)-amine;

(S)-1-(5-(4-(4-Benzyloxy-phenylamino)-quinazolin-6-yl)-furan-2-ylmethyl)-pyrrolidine-2-carboxylic acid amide;

(S)-1-(5-(4-(1-Benzyl-1H-indazol-5-ylamino)-quinazolin-6-yl)-furan-2-ylmethyl)-pyrrolidine-2-carboxylic acid amide;

(1-Benzyl-1H-indazol-5-yl)-(6-(5-((2-methanesulphonyl-ethylamino)-methyl)-furan-2-yl)-quinazolin-4-yl)-amine;

(4-Benzyloxy-phenyl)-(6-(5-(((2-methanesulphony-ethyl)-methyl-amino)-methyl)-furan-2-yl)-quinazolin-4-yl)-amine;

N-(2-((5-(4-(4-Benzyloxy-phenylamino)-quinazolin-6-yl)-furan-2-ylmethyl)-amino)-ethyl)-methanesulphonamide;

and salts or solvates thereof, particularly pharmaceutically acceptable salts or solvates thereof.

Further particularly preferred compounds of the present invention include:

1-(3-(4-(1-Benzyl-1H-indazol-5-ylamino)-quinazolin-6-yl)-1,2,4-oxadiazol-5-ylmethyl)-piperidin-4-one;

1-(3-(4-(1-Benzyl-1H-indazol-5-ylamino)-quinazolin-6-yl)-1,2,4-oxadiazol-5-ylmethyl)-pyrrolidin-2-one;

and salts or solvates thereof, particularly pharmaceutically acceptable salts or solvates thereof.

Certain compounds of formula (I) may exist in stereoisomeric forms (e.g. they may contain one or more asymmetric carbon atoms or may exhibit cis-trans isomerism). The individual stereoisomers (enantiomers and diastereoisomers) and mixtures of these are included within the scope of the present invention. Likewise, it is understood that compounds of formula (I) may exist in tautomeric forms other than that shown in the formula and these are also included within the scope of the present invention.

Salts of the compounds of the present invention may comprise acid addition salts derived from a nitrogen in the compound of formula (I). The therapeutic activity resides in the moiety derived from the compound of the invention as defined herein and the identity of the other component is of less importance although for therapeutic and prophylactic purposes it is, preferably, pharmaceutically acceptable to the patient. Examples of pharmaceutically acceptable acid addition salts include those derived from mineral acids, such as hydrochloric, hydrobromic, phosphoric, metaphosphoric, nitric and sulphuric acids, and organic acids, such as tartaric, acetic, trifluoroacetic, citric, malic, lactic, fumaric, benzoic, glycolic, gluconic, succinic and methanesulphonic and arylsulphonic, for example p-toluenesulphonic, acids.

According to a further aspect of the present invention there is provided a process for the preparation of a compound of formula (I) as defined above which comprises the steps:

(a) the reaction of a compound of formula (II)

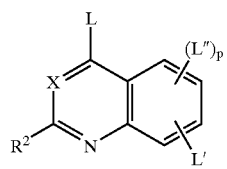
(II)

wherein X, p and $R^2$ are as defined above and L, L' and L" are suitable leaving groups, with a compound of formula (III)

UYH (III)

wherein U and Y are as defined above, to prepare a compound of formula (IV)

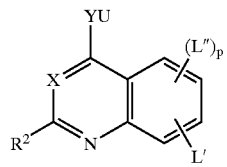
(IV)

and subsequently (b) reaction with an appropriate reagent to substitute the group $R^1$ onto the phenyl ring by replacement of the leaving group L'; and (c) where p is other than 0, reaction with appropriate reagent(s) to substitute the group (s) $R^3$ onto the phenyl ring by replacement of the leaving group(s) L"; and, if desired, (d) subsequently converting the compound of formula (I) thereby obtained into another compound of formula (I) by means of appropriate reagents.

Alternatively, the compound of formula (II) as defined above is reacted with the appropriate reagents to substitute the groups $R^1$ and $R^3$ onto the phenyl ring by replacement of the respective leaving groups and then the product thereby obtained (of formula (V) below) is reacted with the compound of formula (III) as defined above, followed, if desired, by conversion of the compound of formula (I) thereby obtained into another compound of formula (I).

In a variant of this alternative the compound of formula (V)

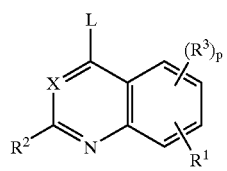
(V)

may be prepared by the reaction of a compound of formula (VI)

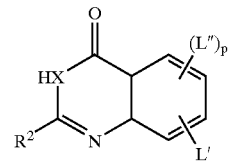
(VI)

with appropriate reagents to substitute the group(s) $R^3$ and the group $R^1$ onto the phenyl ring to prepare a compound of formula (VII)

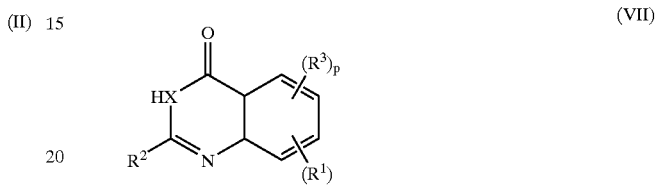
(VII)

and subsequent reaction to incorporate the leaving group L. For example, a chloro leaving group can be incorporated by reaction of a corresponding 3,4-dihydropyrimidone with carbon tetrachloride/triphenylphosphine in an appropriate solvent.

Simplified versions of these general processes will apply where p is 0.

The group $R^1$ may, therefore, be substituted onto the phenyl ring by replacement of a suitable leaving group. This is especially suitable for preparing compounds where $R^1$ is a substituted or unsubstituted phenyl or heterocyclic ring system; such compounds may, for example, be prepared by reaction of the corresponding aryl or heteroaryl stannane derivative with the corresponding compound of formula (IV) carrying the leaving group L' in the appropriate position on the ring.

The group(s) $R^3$ may, therefore, also be substituted onto the phenyl ring by replacement of suitable leaving group(s). This is especially suitable for preparing compounds of formula (I) wherein an $R^3$ group is linked to the phenyl ring by a nitrogen atom; such compounds may, for example, be obtained by reaction of the amine corresponding to the group $R^3$ with the corresponding compound carrying a halo substituent in the appropriate position on the ring.

The reagents used to effect the substitution of the groups $R^1$ and $R^3$ onto the phenyl ring may, in certain circumstances, include appropriate protecting group(s) well known to the person skilled in the art for particular functionalities. This may, for example, be suitable where either of the groups $R^1$ or $R^3$ contain a free amino functionality. Such protecting group(s) would be removed by standard methods after the substitution onto the phenyl ring has been effected. For a description of protecting groups and their use see T. W. Greene and P. G. M. Wuts, "Protective Groups in Organic Synthesis", 2nd edn., John Wiley & Sons, New York, 1991.

According to a further aspect of the present invention there is provided a process for the preparation of a compound of formula (I) as defined above which comprises the steps:

(a) reacting a compound of formula (IV) as defined above with appropriate reagent(s) to prepare a compound wherein either the group L' or the group(s) L" (when p is other than 0) is(are) replaced with an appropriately functionalised group Z;

and (b) subsequently converting the group Z into the group $R^1$ where L' has been replaced or into the group $R^3$ where L" has been replaced by means of appropriate reagent(s); (c) reacting with appropriate reagents to substitute the other of $R^3$ and $R^1$ onto the phenyl ring by replacement of the remaining leaving group L" and L' respectively, if present; and, if desired, (d) subsequently converting the compound of formula (I) thereby obtained into another compound of formula (I) by means of appropriate reagents.

Such processes are particularly suitable for the preparation of compounds of formula (I) wherein either $R^1$ carries or $R^3$ represents a substituent selected from $M^1$-$M^2$-$M^3$-$M^4$, $M^1$-$M^5$ or $M^1$-$M^2$-$M^3$'-$M^6$ as defined above in which $M^2$ represents $NR^{12}$. In such cases preferably the group Z carries a terminal formyl group (CHO).

Such processes are especially suitable for the preparation of compounds of formula (I) wherein p is 0 and $R^1$ carries a substituent selected from $M^1$-$M^2$-$M^3$-$M^4$, $M^1$-$M^5$ or $M^1$-$M^2$-$M^3$'-$M^6$ as defined above in which $M^2$ represents $NR^{12}$.

Where Z carries a formyl group the compound may be suitably prepared from the corresponding dioxolanyl substituted compound, for example by acid hydrolysis.

The dioxolanyl substituted compound may be prepared by reaction of a compound of formula (IV) with an appropriate reagent to substitute the relevant leaving group with the substituent carrying the dioxolanyl ring. This reagent could, for example, be an appropriate heteroaryl stannane derivative.

Where Z carries a terminal formyl group the compound could suitably be prepared by reaction of a compound of formula (IV) with an appropriate heteroaryl stannane derivative. This derivative is either readily available or can be readily synthesised by those skilled in the art using conventional methods of organic synthesis. Suitable possibilities for preparation of compounds where $R^1$ carries the aforementioned substituents include the following schematic examples:

Analogous methods could be used for phenyl and other heterocyclic ring systems and also for the preparation of compounds where $R^3$ represents one of the aforementioned substituents.

Therefore a suitable process may comprise reaction of the compound in which the group Z carries a terminal formyl group (i.e. a —CHO or —($C_{1-3}$ alkylene)-CHO group) with a compound of formula $HM^2$-$M^3$-$M^4$, a compound of formula $HM^2$-$M^3$'-$M^6$ or a compound of formula $HM^5$, wherein $M^2$ represents $NR^{12}$. The reaction preferably involves a reductive amination by means of an appropriate reducing agent, for example sodium triacetoxyborohydride.

A similar process would be involved where in $M^1$ one $CH_2$ group was replaced with a CO group and $M^2$ was $NR^{12}$. If necessary, in certain circumstances, the ketone could be protected by standard methods to ensure that the reductive amination involved the aldehyde functionality.

For the preparation of those compounds wherein in $M^1$ the $CH_2$ group adjacent to $M^2$ is replaced with a CO group a suitable process would comprise reaction of a compound in which the group Z carries a —($C_{0-3}$ alkylene)-$CO_2H$ group with a compound of formula $HM^2$-$M^3$-$M^4$, a compound of formula $HM^2$-$M^3$-$M^6$ or a compound of formula $HM^5$, wherein $M^2$ represents $NR^{12}$.

Alternatively, an analogous scheme to those described above could be used wherein the substitution of the groups $R^1$ and $R^3$ onto the phenyl ring occurs prior to the coupling reaction with the compound of formula (III).

According to a further alternative process the group Z is converted into the group $R^1$ by a de novo synthesis of a substituted or unsubstituted heterocyclic ring system using appropriate reagents. Such a process would involve standard synthetic methodology known to the person skilled in the art for building up the heterocyclic ring system.

For example, Z could suitably represent an alkyne group which when reacted with an appropriate nitrile oxide results in the formation of an isoxazole ring system; reaction with an azide would result in the formation of a triazole ring system. The group Z could also suitably represent an amidoxime group (derived from a cyano group) which when

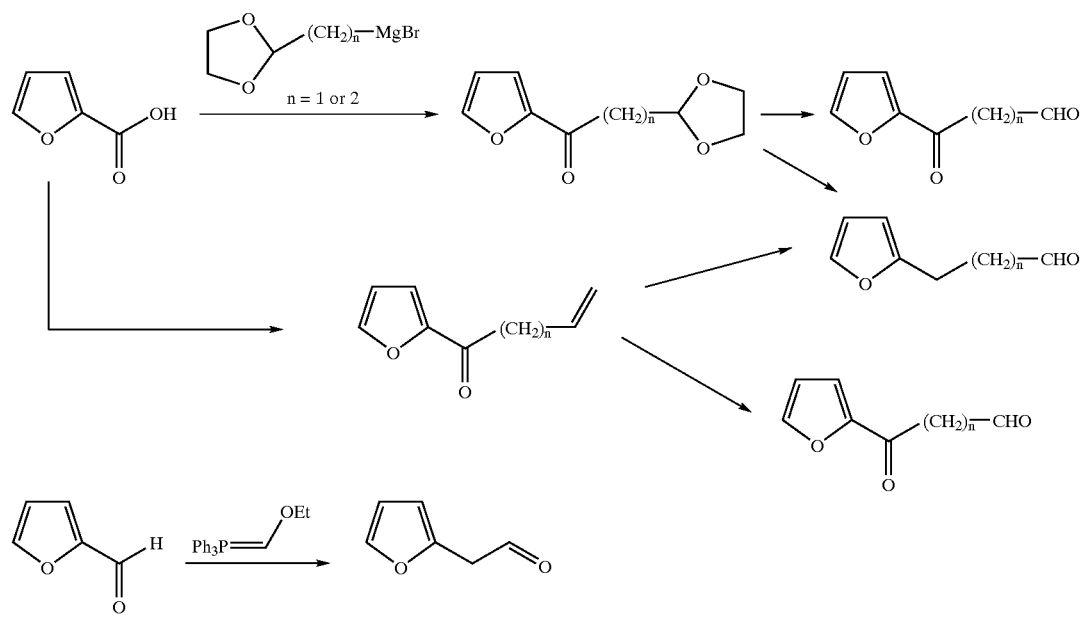

The resulting compounds would, for example, then be converted into the respective stannane derivative.

reacted with an activated carboxylic acid derivative (such as an acid chloride or an acid imidazolide) would result in the formation of a 1,2,4-oxadiazole ring system. The group Z could also suitably represent a bromomethylenecarbonyl group which would be reacted with an imidate to result in the formation of an oxazole ring system, with a guanidino group to result in the formation of an N-imidazole ring system or with an amidine group to result in the formation of a C-imidazole ring system. The group Z could also suitably represent an activated carboxylic acid group which would be reacted to form a hydrazinoketone which would subsequently be reacted with another activated carboxylic acid derivative to result in the preparation of a 1,3,4-oxadiazole ring system. Thus reaction of a compound carrying a relevant Z group with appropriate reagents carrying one of —C=N=O, —NH—C(NH$_2$)=NH, —COX, —C(NH$_2$)=NOH, —C(OMe)=NH, or —C(NH$_2$)=NH as a terminal group would result in the formation of the ring systems indicated above.

Alternatively, an analogous scheme to those described above could be used wherein the substitution of the group R$^1$ onto the phenyl ring occurs prior to the coupling reaction with the compound of formula (III).

The following scheme outlines, for example, the synthesis of derivatives carrying a substituted 1,3,4-oxadiazole ring as an R$^1$ substituent:

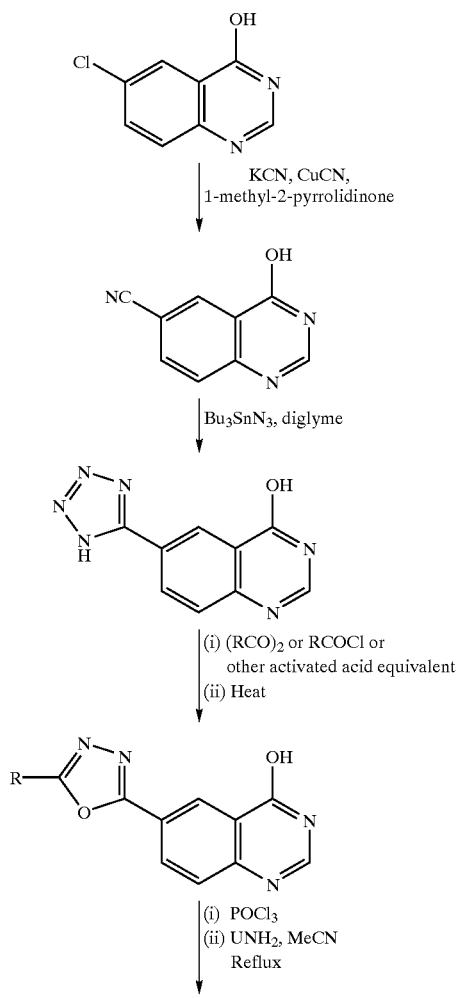

-continued

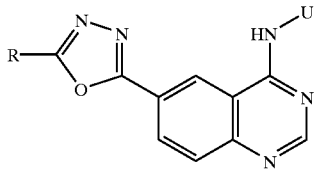

Such processes are particularly suitable for the preparation of the compounds of formula (I) wherein R$^1$ carries a substituent selected from M$^1$-M$^2$-M$^3$-M$^4$, M$^1$M$^5$ or M$^1$-M$^2$-M$^3'$-M$^6$ as defined above in which M$^2$ represents CR$^{12}$R$^{13}$, including those in which in M$^1$ one CH$_2$ group is replaced by a CO group.

For example, a group R$^3$ may be substituted onto the phenyl ring by replacement of another group R$^3$ which is a suitable leaving group. This is especially suitable for preparing compounds of formula (I) wherein an R$^3$ group is linked to the phenyl ring by a nitrogen atom; such compounds may, for example, be obtained by reaction of the amine corresponding to the group R$^3$ with the corresponding compound of formula (I) carrying a halo substituent in the appropriate position on the ring.

Similarly a group R$^1$ may be substituted onto the phenyl ring by replacement of a group R$^3$ which is a suitable leaving group. This is especially suitable for preparing compounds where R$^1$ is a phenyl or heterocyclic ring system; such compounds may, for example, be prepared by reaction of the corresponding aryl or heteroaryl stannane derivative with the corresponding compound of formula (I) carrying a halo substituent in the appropriate position on the ring.

For example, a compound containing an alkyl or aryl mercapto group may be oxidised to the corresponding sulphinyl or sulphonyl compound by use of an organic peroxide (eg benzoyl peroxide) or suitable inorganic oxidant (eg OXONE®).

A compound containing a nitro substituent may be reduced to the corresponding amino-compound, eg by use of hydrogen and an appropriate catalyst (if there are no other susceptible groups) or by use of Raney Nickel and hydrazine hydrate.

Amino or hydroxy substituents may be acylated by use of an acid chloride or an anhydride under appropriate conditions. Equally an acetate or amide group may be cleaved to the hydroxy or amino compound respectively by treatment with, for example, dilute aqueous base.

In addition reaction of an amino substituent with triphosgene and another amine (eg aqueous ammonia, dimethylamine) gives the urea substituted product.

An amino substituent may also be converted to a dimethylamino substituent by reaction with formic acid and sodium cyanoborohydride.

Such processes are especially suitable for the preparation of compounds of formula (I) wherein p is 0 and R$^1$ carries a substituent selected from M$^1$-M$^2$-M$^3$-M$^4$, M$^1$-M$^5$ or M$^1$-M$^2$-M$^3'$-M$^6$ as defined above in which M$^2$ represents CR$^{12}$R$^{13}$.

Suitable leaving groups for L, L' and L" will be well known to those skilled in the art and include, for example, halo such as chloro and bromo; sulphonyloxy groups such as methanesulphonyloxy and toluene-p-sulphonyloxy; alkoxy groups; and triflate.

The coupling reaction referred to above with the compound of formula (III) is conveniently carried out in the presence of a suitable inert solvent, for example a C$_{1-4}$ alkanol, such as isopropanol, a halogenated hydrocarbon, an ether, an aromatic hydrocarbon or a dipolar aprotic solvent such as acetone or acetonitrile at a non-extreme temperature, for example from 0 to 150°, suitably 10 to 100° C., preferably 50 to 100° C.

Optionally, the reaction is carried out in the presence of a base when Y=NH. Examples of suitable bases include an organic amine such as triethylamine, or an alkaline earth metal carbonate, hydride or hydroxide, such as sodium or potassium carbonate, hydride or hydroxide. When YH=OH or SH it is necessary to perform the reaction in the presence of a base, and in such a case the product is not obtained as the salt.

The compound of formula (I) in the case in which Y=NR$^b$ may be obtained from this process in the form of a salt with the acid HL, wherein L is as hereinbefore defined, or as the free base by treating the salt with a base as hereinbefore defined.

The compounds of formulae (II) and (III) as defined above, the reagents to substitute the group(s) R$^3$ and the group R$^1$, and the reagent(s) to convert the group Z into the group R$^3$ or R$^1$ are either readily available or can be readily synthesised by those skilled in the art using conventional methods of organic synthesis.

As indicated above, the compound of formula (I) prepared may be converted to another compound of formula (I) by chemical transformation of the appropriate substituent or substituents using appropriate chemical methods (see for example, J. March "Advanced Organic Chemistry", Edition III, Wiley Interscience, 1985).

A formyl substituent may be converted to a hydroxymethyl or a carboxy substituent by standard reduction or oxidation methods respectively.

All of the above-mentioned chemical transformations may also be used to convert one compound of formula (II) to a further compound of formula (II) prior to any subsequent reaction; or to convert one compound of formula (II) to a further compound of formula (III) prior to any subsequent reaction.

Various intermediate compounds used in the above-mentioned processes, including but not limited to certain of the compounds of formulae (II), (III), (IV), (V), (VI) and (VII) as illustrated above, are novel and thus represent a further aspect of the present invention.

The compounds of formula (I) and salts thereof have anticancer activity as demonstrated hereinafter by their inhibition of the protein tyrosine kinase c-erbB-2, c-erbB-4 and/or EGF-r enzymes and their effect on selected cell lines whose growth is dependent on c-erbB-2 or EGF-r tyrosine kinase activity.

The present invention thus also provides compounds of formula (I) and pharmaceutically acceptable salts or solvates thereof for use in medical therapy, and particularly in the treatment of disorders mediated by aberrant protein tyrosine kinase activity such as human malignancies and the other disorders mentioned above. The compounds of the present invention are especially useful for the treatment of disorders caused by aberrant c-erbB-2 and/or EGF-r activity such as breast, ovarian, gastric, pancreatic, non-small cell lung, bladder, head and neck cancers, and psoriasis.

A further aspect of the invention provides a method of treatment of a human or animal subject suffering from a disorder mediated by aberrant protein tyrosine kinase activity, including susceptible malignancies, which comprises administering to said subject an effective amount of a compound of formula (I) or a pharmaceutically acceptable salt or solvate thereof.

A further aspect of the present invention provides the use of a compound of formula (I), or a pharmaceutically acceptable salt or solvate thereof, in therapy.

A further aspect of the present invention provides the use of a compound of formula (I), or a pharmaceutically acceptable salt or solvate thereof, in the preparation of a medicament for the treatment of cancer and malignant tumours.

A further aspect of the present invention provides the use of a compound of formula (I), or a pharmaceutically acceptable salt or solvate thereof, in the preparation of a medicament for the treatment of psoriasis.

Whilst it is possible for the compounds or salts of the present invention to be administered as the new chemical, it is preferred to present them in the form of a pharmaceutical formulation.

According to a further feature of the present invention there is provided a pharmaceutical formulation comprising at least one compound of formula (I), or a pharmaceutically acceptable salt or solvate thereof, together with one or more pharmaceutically acceptable carriers, diluents or excipients.

Pharmaceutical formulations may be presented in unit dose forms containing a predetermined amount of active ingredient per unit dose. Such a unit may contain for example 0.5 mg to 1 g, preferably 70 mg to 700 mg, more preferably 5 mg to 100 mg of a compound of the formula (I) depending on the condition being treated, the route of administration and the age, weight and condition of the patient.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists which may be generated by means of various types of metered dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Preferred unit dosage formulations are those containing a daily dose or sub-dose, as herein above recited, or an appropriate fraction thereof, of an active ingredient.

It should be understood that in addition to the ingredients particularly mentioned above, the formulations may include other agents conventional in the art having regard to the type of formulation in question, for example those suitable for oral administration may include flavouring agents.

The animal requiring treatment with a compound, salt or solvate of the present invention is usually a mammal, such as a human being.

A therapeutically effective amount of a compound, salt or solvate of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of the present invention for the treatment of neoplastic growth, for example colon or breast carcinoma will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt or solvate of the present invention may be determined as a proportion of the effective amount of the compound per se.

The compounds of the present invention and their salts and solvates may be employed alone or in combination with other therapeutic agents for the treatment of the above-mentioned conditions. In particular, in anti-cancer therapy, combination with other chemotherapeutic, hormonal or antibody agents is envisaged. Combination therapies according to the present invention thus comprise the administration of at least one compound of formula (I) or a pharmaceutically acceptable salt or solvate thereof and at least one other pharmaceutically active agent. The compound(s) of formula (I) and the other pharmaceutically active agent(s) may be administered together or separately and, when administered separately this may occur simultaneously or sequentially in any order. The amounts of the compound(s) of formula (I) and the other pharmaceutically active agent(s) and the relative timings of administration will be selected in order to achieve the desired combined therapeutic effect.

Certain embodiments of the present invention will now be illustrated by way of example only. The physical data given for the compounds exemplified is consistent with the assigned structure of those compounds.

$^1$H NMR spectra were obtained at 250 MHz on a Bruker AC250 or Bruker AM250 spectrophotometer. J values are given in Hz. Mass spectra were obtained on one of the following machines: VG Micromass Platform (electrospray positive or negative) or HP5989A Engine (thermospray positive). Analytical thin layer chromatography (tlc) was used to verify the purity of some intermediates which could not be isolated or which were too unstable for full characterisation, and to follow the progress of reactions. Unless otherwise stated, this was done using silica gel (Merck Silica Gel 60 F254). Unless otherwise stated, column chromatography for the purification of some compounds used Merck Silica gel 60 (Art. 1.09385, 230–400 mesh), and the stated solvent system under pressure.

Petrol refers to petroleum ether, either the fraction boiling at 40–60° C., or at 60–80° C.

Ether refers to diethylether.

DMAP refers to 4-dimethylaminopyridine.

DMF refers to dimethylformamide.

DMSO refers to dimethylsulphoxide.

IMS refers to industrial methylated spirit.

THF refers to tetrahydrofuran.

TMEDA refers to N,N,N',N'-tetramethylethylenediamine.

HPLC refers to high pressure liquid chromatography.

RT refers to retention time.

Useful preparative techniques are described in WO096/09294, WO097/03069 and WO097/13771; also described in these publications are appropriate intermediate compounds other than those detailed below.

General Procedures (A) Reaction of an Amine with a Quinazoline or Quinoline

The optionally substituted quinazoline or quinoline and the specified amine were mixed in an appropriate solvent and heated to reflux. When the reaction was complete (as judged by tlc), the reaction mixture was allowed to cool. The resulting suspension was diluted, e.g. with acetone, and the solid collected by filtration, washing e.g. with excess acetone, and dried at 60° C. in vacuo, giving the product as the hydrochloride salt. If the free base was required (e.g. for further reaction), this was obtained by treatment with a base e.g. triethylamine; purification by chromatography was then performed, if required.

(B) Reaction of a Product from Procedure (A) with a Heteroaryl Tin Reagent

A stirred mixture of the product from Procedure (A), (containing a suitable leaving group such as chloro, bromo, iodo or triflate), a heteroaryl stannane and a suitable palladium catalyst, such as bis-(triphenylphosphine)palladium (II) chloride or 1,4-bis(diphenylphosphino)-butane palladium (II) chloride (prepared as described in C. E. Housecroft et. al, Inorg. Chem. (1991), 30(1), 125–30), together with other appropriate additives, were heated at reflux in dry dioxane or another suitable solvent under nitrogen until the reaction was complete. The resulting mixture was generally purified by chromatography on silica.

(C) Preparation of 6-(5-substituted-1,2,4-oxadiazol-3-yl) quinazolines

Powdered molecular sieves (0.025 g) were added to a solution of a 4-substituted-quinazolin-6-yl-(N-hydroxycarboximidamide) (0.20 mmol) in dry THF (10 ml), and the mixture was stirred at room temperature for 15 minutes. Sodium hydride (0.008 g of 60% dispersion in mineral oil, 0.20 mmol) was added and stirring continued for 30 minutes. An appropriate ester (0.20 mmol or more) was added and the mixture was heated to reflux for several hours. The reaction mixture was concentrated in vacuo, and purified by chromatography on silica using a Bond Elut™ cartridge, using appropriate solvents for elution.

Preparation of Intermediates

4-Benzyloxyaniline is commercially available as the hydrochloride salt; this is treated with aqueous sodium carbonate solution, and the mixture extracted with ethyl acetate; the organic solution is dried (MgSO$_4$) and concentrated to give the free base as a brown solid, used without further purification.

Other substituted anilines were in general prepared by analogous methods to those outlined in WO 96/09294 and/or as follows:

Step 1: Preparation of the Precursor Nitro-compounds

4-Nitrophenol (or an appropriate substituted analogue, such as 3-chloro-4-nitrophenol) was treated with a base such as potassium carbonate or sodium hydroxide in an appropriate solvent, such as acetone or acetonitrile. The appropriate aryl or heteroaryl halide was added and the reaction mixture heated or stirred at room temperature overnight.

Purification A: Most of the acetonitrile was removed in vacuo, and the residue was partitioned between water and dichloromethane. The aqueous layer was extracted with further dichloromethane (×2), and the combined dichloromethane layers were concentrated in vacuo.

Purification B: removal of insoluble material by filtration, followed by concentration of the reaction mixture in vacuo, and chromatography on silica.

Step 2: Reduction to the Corresponding Aniline

The precursor nitro compound was reduced by catalytic hydrogenation at atmospheric pressure using 5%Pt/carbon, in a suitable solvent (e.g. ethanol, THF, or mixtures thereof to promote solubility). When reduction was complete, the mixture was filtered through Harborlite™, washing with excess solvent, and the resulting solution concentrated in vacuo to give the desired aniline. In some cases, the anilines were acidified with HCl (e.g. in a solution in dioxane) to give the corresponding hydrochloride salt.

Anilines prepared by such methods include:
4-(2-Fluorobenzyloxy)aniline; m/z (M+1)$^+$ 218
4-(3-Fluorobenzyloxy)aniline; m/z (M+1)$^+$ 218
4-(4-Fluorobenzyloxy)aniline; m/z (M+1)$^+$ 218
3-Chloro-4-(2-fluorobenzyloxy)aniline; m/z (M+1)$^+$ 252
3-Chloro-4-(3-fluorobenzyloxy)aniline; m/z (M+1)$^+$ 252
3-Chloro-4-(4-fluorobenzyloxy)aniline; m/z (M+1)$^+$ 252
4-(Pyridyl-2-methoxy)aniline; m/z (M+1)$^+$ 201
4-(Pyridyl-4-methoxy)aniline; m/z (M+1)$^+$ 201
4-(Pyridyl-3-methoxy)aniline; m/z (M+1)$^+$ 201
4-Benzyloxy-3-chloroaniline; m/z (M+1)$^+$ 234
and, in appropriate cases, their hydrochloride salts.

4-Benzenesulphonylaniline was prepared by the published method (Helv. Chim. Acta., 1983, 66(4), p1046.

1-Benzyl-5-nitro-1H-indole

Dry dimethylsulphoxide (20 ml) was added to potassium hydroxide (4.2 g, 0.074 mol) (crushed pellets) and the mixture was stirred under nitrogen for 5 mins. 5-Nitroindole (commercially available) (3.0 g, 0.019 mol) was then added and the red mixture stirred for 30 min at room temperature. The mixture was then cooled to −10° C., benzyl bromide (4.4 ml, 0.037 mol) was slowly added and the mixture stirred and allowed to warm to room temperature over a period of 40 mins. Water (50 ml) was then added and the mixture was extracted with diethyl ether (2×200 ml). The extracts were washed with water (4×50 ml), dried over sodium sulphate and evaporated to leave an oily solid. The excess benzyl bromide was removed by dissolving the whole in diethyl ether (50 ml), diluting this solution with 40–60 petrol (50 ml) and then gradually removing the diethyl ether in vacuo to leave a yellow solid suspended in the petrol. The solid was filtered, washed with copious amounts of 40–60 petrol and dried to give 1-benzyl-5-nitroindole (2.4 g, 51%) as a yellow solid, m.p. 102–104° C.; δH [$^2$H$_6$]-DMSO 8.53 (1H, s, 4-H), 8.00 (1H, d, J 9, 6-H), 7.78 (1H, s, 2-H), 7.68 (1H, d, J 9, 7-H), 7.36–7.20 (5H, m, 2'-H, 3'-H, 4'-H, 5'-H, 6'-H), 6.81 (1H, s, 3-H), 5.52 (2H, s, CH$_2$).

5-Amino-1-benzyl-1H-indole

A solution of 1-benzyl-5-nitroindole (0.51 g, 0.02 mol) in a mixture of ethyl acetate (25 ml) and methanol (25 ml) was carefully added to 10% palladium on charcoal (45 mg). The resulting suspension was stirred at room temperature under an atmosphere of hydrogen. When the reaction was complete (indicated by tlc or calculated uptake of hydrogen) the suspension was filtered through a pad of Harbolite™, and the filtrate evaporated to dryness to give 5-amino-1-benzylindole (0.40 g, 91%) as an off-white solid; m.p. 66–68° C.; δH [$^2$H$_6$]-DMSO 7.30–7.12 (6H, m, 2-H, 2"-H, 3"-H, 4"-H, 5"-H, 6"-H), 7.08 (1H, d, J 8, 7-H), 6.70 (1H, s, 4-H), 6.49 (1H, d, J 8, 6-H), 6.18 (1H, s, 3-H), 5.28 (2H, s, CH$_2$), 4.38 (2H, br s, NH$_2$).

2-Benzyl-5-nitro-1H-benzimidazole

A mixture of 4-nitro-o-phenylene diamine (1.54 g) and phenylacetic acid (2.04 g) in 5N aqueous HCl (16 ml) were heated at 110° C. under nitrogen for 22 hours. The mixture was cooled to room temperature and the accumulated black solid collected by filtration. This crude residue was then adsorbed onto silica and chromatographed to give the title compound (0.84 g) as a purple foam; δH CDCl$_3$ 9.70 (1H, bs), 8.15 (1H, d), 7.30 (7H, m), 4.30 (2H, s); m/z (M+1)$^+$ 254.

5-Amino-2-benzyl-1H-benzimidazole

The title compound was prepared from 5-nitro-2-benzylbenzimidazole by an analogous reduction method to that described above for 5-amino-1-benzyl-1H-indole; m/z (M+1)$^+$ 224. Also note the published method (J. Het. Chem., 23, 1109–13, (1986)).

1-N-Benzyl-5-nitro-1H-indazole and 2-N-Benzyl-5-nitro-1H-indazole

A stirred mixture of 5-nitroindazole (50 g), potassium carbonate (46.6 g, 1.1 equiv.) and benzyl bromide (57.6 g, 1.1 equiv) in N,N-dimethylformamide (500 ml) was heated at 75° C. for a period of 4 hours. The reaction was then cooled and water (500 ml) was gradually added to precipitate the product which was filtered off and washed with water (50 ml) and dried in the air at ambient temperature. The weight of pale yellow solid thus obtained was 72.3 g (93%), m.pt. 95–97° C.; HPLC (Partisil 5, dichloromethane, 4 ml /min, 250 nm) gave an isomer ratio (1-N-benzyl:2-N-benzyl) of 63:37 (RT-1N 3.4 min, RT-2N 6.6 min). To a filtered solution of the mixed regioisomers (100 g) in acetone (470 ml) at room temperature was added, gradually with stirring, water (156 ml) and the mixture was stirred for one hour. The resultant yellow crystalline solid was filtered off and dried in the air at ambient temperature to give 36.4 g (34%) of material; m.pt.124–126° C.; HPLC showed an isomer ratio (1-N-benzyl:2-N-benzyl) of 96:4; δH (CDCl$_3$) 5.58 (2H, s, CH$_2$), 7.12–7.15(2H) & 7.22–7.29(3H)-(phenyl), 7.33(1H, dt, J=1 Hz & 9 Hz, H-7), 8.15(1H, dd, J=2 Hz & 9 Hz, H-6), 8.19(1H, d, J=1 Hz, H-3), 8.67 (1H, dd, J=1 Hz & 2 Hz, H-4).

Also note the published method in FR 5600, Jan. 8, 1968.

5-Amino-1-N-benzyl-1H-indazole

1-Benzyl-5-nitroindazole (400 g) was suspended in ethanol (5 liter) and hydrogenated in the presence of 5% platinum on carbon catalyst (20 g) operating at 1 bar pressure and 50–60° C. When hydrogen uptake was complete the reactor contents were heated to 70° C., discharged and filtered while still hot and the filtrate concentrated to ~4 liter which caused some crystallisation. Water (4 liter) was then gradually added with stirring and the mixture was stirred at 5° C. overnight. The resultant crystals were filtered off and air-dried at ambient temperature to give 305 g (86%) of material, m.pt.150–152° C.; HPLC (Supelcosil ABZ+, gradient 0.05% trifluoroacetic acid in water/0.05% trifluoroacetic acid in acetonitrile, 1.5 ml/min, 220 nm) showed <1% of the corresponding 2-N-isomer (RT-1N 6.03 min, RT-2N 5.29 min); δH (CDCl$_3$) 3.3–3.8(2H, broad s, NH$_2$), 5.47 (2H, s, CH$_2$), 6.74(1H, dd, J=2 Hz & 9 Hz, H-6), 6.87(1H, dd, J=1 Hz & 2 Hz,H-4), 7.06–7.11(3H) & 7.17–7.25(3H)-(phenyl & H-7), 7.77(1H, d, J=1 Hz, H-3).

Also note the published method in FR 5600, Jan. 8, 1968.

1-Benzyl-3-methyl-5-nitro-1H-indazole

2-Fluoro-5-nitroacetophenone (H. Sato et al, Bioorganic and Medicinal Chemistry Letters, 5(3), 233–236, 1995) (0.24 g) was treated with triethylamine (0.73 ml)and benzyl hydrazine dihydrochloride (0.255 g) in ethanol (20 ml) at reflux under N$_2$ for 8 days. The mixture was cooled and the solid 1-benzyl-3-methyl-5-nitroindazole (0.16 g) was collected by filtration; m/z (M+1)$^+$ 268.

1-Benzyl-3-methyl-1H-indazol-5-ylamine

1-Benzyl-3-methyl-5-nitroindazole (0.15 g) in THF (15 ml) was treated with platinum on carbon (0.05 g, 5%) under an atmosphere of hydrogen at room temperature. When hydrogen uptake was complete, the mixture was filtered and concentrated in vacuo to give the title compound; m/z (M+1)$^+$ 268.

Further amino-indazole intermediates

The relevant nitro-substituted 1H-indazole was treated with a base such as potassium carbonate or sodium hydroxide in a suitable solvent, such as acetone or acetonitrile. The appropriate aryl halide or heteroaryl halide was added and the reaction mixture heated or stirred at room temperature overnight. Subsequent concentration in vacuo and chromatography on silica gave the desired 1-substituted nitro-1H-indazoles. Hydrogenation was carried out by analogy with the preparation of 5-amino-1-benzyl-1H-indole described above.

Amines prepared by such methods include:

5-Amino-1-benzyl-1H-indazole; m/z (M+1)$^+$ 224

5-Amino-1-(2-fluorobenzyl)-1H-indazole; m/z (M+1)$^+$ 242

5-Amino-1-(3-fluorobenzyl)-1H-indazole; m/z (M+1)$^+$ 242

5-Amino-1-(4-fluorobenzyl)-1H-indazole; m/z (M+1)$^+$ 242

5-Amino-1-(2-pyridylmethyl)-1H-indazole; m/z (M+1)$^+$ 225

5-Amino-1-(3-pyridylmethyl)-1H-indazole; m/z (M+1)$^+$ 225

5-Amino-1-(4-pyridylmethyl)-1H-indazole; m/z (M+1)$^+$ 225

5-Amino-1-(2,3-difluorobenzyl)-1H-indazole; m/z (M+1)$^+$ 260

5-Amino-1-(3,5-difluorobenzyl)-1H-indazole; m/z (M+1)$^+$ 260.

1-Benzenesulphonylindol-5-yl-amine was prepared according to the published method (J. Org. Chem., 55, 1379–90, (1990)).

3-Benzenesulphonylindol-6-yl-amine

3-Benzenesulphonyl-6-nitroindole (K. Wojciechowski and M Makosza, Tet. Lett., 25 (42), p4793, 1984) was hydrogenated by analogy with the procedures above to give the title compound; δH [$^2$H$_6$]DMSO 11.64 (1H, s), 7.94 (2H, m), 7.81 (1H, s), 7.57 (3H, m), 7.49(1H, d), 6.60(1H, s), 6.55 (1H, dd), 5.40 (2H, s).

4-Chloro-6-bromoquinazoline and 4-Chloro-6-iodoquinazoline were prepared as described in WO 96/09294.

(4-Benzyloxy-phenyl)-(6-bromoquinazolin-4-yl)-amine hydrochloride

4-Chloro-6-bromoquinazoline (0.25 g, 1.0 mmol) and 4-benzyloxyaniline (0.25 g, 1.3 mmol) were mixed in 2-propanol (6 ml) and heated at reflux for 10 mins (Procedure A). The solution was allowed to cool at room temperature and the 2-propanol removed in vacuo. The resulting solid was triturated with acetone to give the product as a yellow solid (0.39 g, 88%); δH [$^2$H$_6$]-DMSO 11.60 (1H, b, NH), 9.21 (1H, s, 5-H), 8.86 (1H, s, 2-H), 8.20 (1H, d, 7-H), 7.90 (1H, d, 8-H), 7.65 (2H, d, 2'-H, 6'-H), 7.50–7.25 (5H, m, Ph-H), 7.10 (2H, d, 3'-H, 5'-H), 5.15 (2H, s, CH$_2$); m/z 405/407 (M+).

(1-Benzyl-1H-indazol-5-yl)-(6-bromoquinazolin-4-yl)-amine (Procedure A)

6-Bromo-4-chloroquinazoline (5.0 g) was reacted with 5-amino-1-benzyl-1H-indazole (5.0 g) in acetonitrile (100 ml) at 100° C. The resulting precipitate was treated with triethylamine in ethyl acetate and water to give the title compound as a yellow solid, (7.37 g); δH [$^2$H$_6$]-DMSO 9.93(1H, s), 8.82 (1H, d), 8.52(1H, s), 8.19(1H, s), 8.09(1H, s), 7.92(1H, dd), 7.65(3H, m), 7.25(5H, m), 5.62(2H, s).

(1-Benzyl-1H-indazol-5-yl)-(6-iodoquinazolin-4-yl)-amine hydrochloride

4-Chloro-6-iodoquinazoline (5.8 g) was treated with 5-amino-1-benzyl-1H-indazole (3.90 g) in acetonitrile (500 ml) at reflux under N$_2$ for 18 hours (Procedure A). Subsequent cooling and filtration gave the title compound (8.26 g); m/z (M+1)$^+$ 478.

4-Nitro-1,3-dibenzoic acid

4-Nitro-m-xylene (27.0 g, 178.6 mmol) was added to water (1.20 l) and heated to reflux. Potassium permanganate (174 g, 1101 mmol) was added portionwise over 6 hours. The reaction was allowed to cool and left to stand for three days. It was then reheated and filtered while hot. The filtrate was cooled (ice bath), and acidified with conc. HCl. After standing for 2 hours, the resulting cream precipitate was collected by filtration to give the title compound (21.5 g, 101.8 mmol, 57%); δH [$^2$H$_6$] DMSO 13.0 (2H, br s), 8.33 (1H, s), 8.36 (1H, d), 8.27 (1H, d).

4-Amino-1,3-dibenzoic acid

A solution of 4-nitro-1,3-dibenzoic acid (21.5 g, 101.8 mmol) in ethanol (540 ml) was reduced using hydrogen at atmospheric pressure and catalytic palladium/carbon (2.0 g, 10%Pd/C on dry weight, 50% water). The mixture was diluted with DMF to dissolve the product and filtered through Harbolite™. Concentration of the filtrate in vacuo gave a white solid which was washed with water and dried at 60° C. in vacuo to give the title compound (17.77 g, 98.1 mmol, 96%); δH [$^2$H$_6$] DMSO 12.5 (2H, br s), 8.35 (1H, d), 7.73 (1H, dd), 6.77 (1H, d).

6-(Carboxy)-quinazolin-4-one

4-Amino-1,3-dibenzoic acid (6.9 g) was treated with formamide (14 ml) at 180° C. under N$_2$. After 3.5 hours, the mixture was cooled and diluted with acetone (100 ml). Filtration gave the title compound (4 g) as a white solid; δH [$^2$H$_6$]DMSO 8.74(1H, d), 8.35 (1H, dd), 8.23 (1H, s), 7.72 (1H, d).

6-(Hydrazido)quinazolin-4-one 6-(Carboxy)quinazolin-4-one (4.84 g) was treated with 1,1'-carbonyldiimidazole (8.28 g) in THF at room temperature under N$_2$. After 8 hours, hydrazine hydrate (1.6 ml) was added and stirring was continued for a further 16 hours. The resulting solid was filtered, washed with THF and dried in vacuo to yield the title compound (4.66 g) as a cream solid; δH [$^2$H$_6$]DMSO 10.1 (1H, bs), 8.60(1H, s), 8.70 (1H, m), 7.70 (1H, d), 7.02 (1H, s); m/z (M+1$^+$) 205.

6-(5-Methyl-1,3,4-oxadiazol-2-yl)quinazolin-4-one 6-(Hydrazido)quinazolin-4-one (3.00 g) in triethylorthoacetate (100 ml) was heated at reflux under N$_2$ for 5 hours. The cooled mixture was filtered to give the title compound as a cream solid; δH [$^2$H$_6$]DMSO 12.65 (1H, bs), 8.71(1H, d), 8.45 (1H, dd), 8.33 (1H, s), 7.95 (1H, s) 2.73 (3H, s); m/z (M+1$^+$) 229.

4-Chloro-6-(5-methyl-1,3,4-oxadiazol-2-yl)quinazoline 6-(5-Methyl-1,3,4-oxadiazol-2-yl)quinazolin-4-one (0.3 g) was treated with phosphorus oxychloride at reflux under N$_2$ for 5 hours. The mixture was concentrated in vacuo and the residue azeotroped with toluene. This was then taken up in ethyl acetate and washed with 5% sodium bicarbonate and saturated brine, dried over magnesium sulphate and concentrated in vacuo to give the title compound (0.22 g) as a yellow solid; δH [$^2$H$_6$]DMSO 12.65 (1H, bs), 8.71(1H, d), 8.45 (1H, dd), 8.33 (1H, s), 7.95 (1H, s) 2.73 (3H, s).

6-Cyanoquinazolin-4-one

6-Iodoquinazolin-4-one (10 g) in 1-methyl-2-pyrrolidinone (50 ml) was treated with copper (I) cyanide (4.28 g) at 206° C. under N$_2$ for 16 hours. The resulting mixture was cooled to 170° C. and the methyl-2-pyrrolidinone removed by vacuum distillation. Potassium cyanide (2.4 g) in water (30 ml) and ethyl acetate (150 ml) were added to the cooled residue and heating continued at 110° C. for 1.5 hours. This mixture was then filtered hot through a pad of celite and the filter cake washed thoroughly with ethyl acetate. Subsequent separation, drying and concentration in vacuo gave the title compound (2.29 g) as a beige solid; δH [$^2$H$_6$]DMSO 12.65(1H, bs), 8.53(1H, d), 8.28(1H, s), 8.19(1H, dd), 7.82(1H, d); m/z (M-1$^+$) 171.

An alternative synthetic method to prepare this compound is illustrated below.

6-(1,2,3,4-Tetrazol-5-yl)-quinazolin-4-one

6-Cyanoquinazolin-4-one (0.5 g) in dimethylformamide (5 ml) was treated with ammonium chloride (0.33 g) and sodium azide (0.38 g) and heated at 100° C. under nitrogen for 45 minutes. The resulting mixture was cooled, diluted with ethyl acetate and filtered. The filter cake was washed with dimethylformamide and ethyl acetate to give the title compound (0.56 g) as a cream solid; δH [$^2$H$_6$]DMSO 13.00(1H, bs), 8.70(1H, d), 8.40(1H, dd), 8.38(1H, bs), 8.05(1H, s), 7.68(1H, d); m/z (M-1$^+$) 213.

6-(5-Methyl-1,3,4-oxadiazol-2-yl)quinazolin-4-one 6-(1,2,3,4-Tetrazol-5-yl)-quinazolin-4-one (3.31 g) was treated with acetic anhydride (115 ml) at reflux under N$_2$ for 1 hour. The anhydride was removed in vacuo, the residue absorbed onto silica and purified by chromatography to give the title compound as a white solid (3.47 g). The analytical data was consistent with that given earlier.

6-(5-Trifluoromethyl-1,3,4-oxadiazol-2-yl)quinazolin-4-one 6-(1,2,3,4-Tetrazol-5-yl)-quinazolin-4-one (1.0 g) was treated with trifluoroacetic anhydride (50 ml) at 50° C. under N$_2$ for 5 hours. The anhydride was removed in vacuo, the residue absorbed onto silica and purified by chromatography to give the title compound as a white solid (0.79 g); δH [$^2$H$_6$]DMSO 12.63(1H, bs), 8.71(1H, d), 8.45(1H, dd), 8.27 (1H, s), 7.90(1H, d); m/z (M-1$^+$) 281.

4-Chloro-6-(5-trifluoromethyl-1,3,4-oxadiazol-2-yl) quinazoline 6-(5-Trifluoromethyl-1,3,4-oxadiazol-2-yl)quinazolin-4-one (0.79 g) was treated with phosphorus oxychloride (18 ml) and triethylamine (8 ml) at reflux under N$_2$ for 2 hours. The mixture was concentrated in vacuo and the residue azeotroped with toluene. This was then taken up in ethyl acetate and washed with 5% sodium bicarbonate and saturated brine, dried over magnesium sulphate and concentrated in vacuo to give the title compound (0.76 g) as an orange solid; δH CDCl$_3$ 9.17(1H, s), 9.05 (1H, d), 8.69(1H, dd), 8.30(1H, d).

(4-Benzyloxy-phenyl)-(6-iodoquinazolin-4-yl)-amine hydrochloride

4-Chloro-6-iodoquinazoline (8 g) was treated with 4-benzyloxyaniline (5.5 g) in acetonitrile (500 ml) at reflux under N$_2$ for 18 hours. Subsequent cooling and filtration gave the title compound (13.13 g); m/z (M+1)$^+$ 454.

(4-Benzyloxy-phenyl)-(6-cyanoquinazolin-4-yl)-amine (4-Benzyloxy-phenyl)-(6-iodoquinazolin-4-yl)-amine (1.2 g) in dioxane (10 ml) under N$_2$ was treated with tributyltin cyanide (0.79 g) and catalytic quantities of 1.4-bis-(diphenylphosphino)-butane palladium (II) chloride and tetrakis (triphenylphosphine) palladium at reflux for 23 hours. The mixture was absorbed onto silica and chromatographed to give the title compound (0.65 g); δH [$^2$H$_6$]DMSO 10.01(1H, s), 9.14(1H, s), 8.63(1H, s), 8.15(1H, d), 7.87(1H, d), 7.73(2H, d), 7.45(5H, m), 7.10(2H, d), 5.13(2H, s); m/z (M+1)$^+$ 353.

(4-(1-Benzyl-1H-indazol-5-ylamino)-quinazolin-6-yl)-carboxylic acid (1-Benzyl-1H-indazol-5-yl)-(6-iodoquinazolin-4-yl)-amine (0.48 g) in DMF under CO was treated with sodium formate (0.1 g) and catalytic quantities of triphenyl phosphine and bistriphenylphosphine palladium (II) chloride at 110° C. The mixture was cooled, added to 5% sodium hydroxide and extracted with ethyl acetate. The aqueous phase was treated with 2N HCl and the precipitated solid filtered and dried to give the title compound (0.07 g); δH [$^2$H$_6$]DMSO 13.35(1H, bs), 10.40(1H, s), 9.30(1H, s), 8.60 (1H, s), 8.30(1H, d), 8.17(2H, d), 7.84(1H, d), 7.72(1H, s), 7.30(5H, m), 5.70(2H, s); m/z (M+1)$^+$ 396.

(1-Benzyl-1H-indazol-5-yl)-(6-hydrazidoquinazolin-4-yl)-amine (4-(1-Benzyl-1H-indazol-5-ylamino)-quinazolin-6-yl)-carboxylic acid (0.15 g) and carbonyl diimidazole (0.123 g) in dry THF (10 ml) was stirred at 20° C. for 3 hours under N$_2$. Hydrazine hydrate (0.04 ml) was added and the mixture stirred at 20° C. for 18 hours. The mixture was concentrated in vacuo to give the title compound as a solid (0.28 g) which was used in subsequent synthetic steps without further purification; tlc (silica, CH$_2$Cl$_2$:EtOH:NH$_3$ 100:8:1) Rf 0.18; m/z (M+1)$^+$ 410.

(1-Benzyl-1H-indazol-5-yl)-(6-(methanesulphonylethanoylhydrazido)-quinazolin-4-yl)-amine Methanesulphonyl acetic acid (0.067 g) and carbonyl diimidazole (0.119 g) were stirred in a THF/DMF mixture (10 ml/1 ml) under N$_2$ for 3 hours. (1-Benzyl-1H-indazol-5-yl)-(6-hydrazidoquinazolin-4-yl)-amine (0.10 g) was added and the mixture stirred at 20° C. for 18 hours. The mixture was absorbed onto silica and chromatographed to give the title compound (0.06 g); m/z (M+1)$^+$ 530.

(1-Benzyl-1H-indazol-5-yl)-(6-cyanoquinazolin-4-yl)-amine (1-Benzyl-1H-indazol-5-yl)-(6-iodoquinazolin-4-yl)-amine (3.58 g) in dioxane (30 ml) under N$_2$ was treated with tributyltin cyanide (2.51 g) and catalytic quantities of 1.4-bis-(diphenylphosphino)-butane palladium (II) chloride and tetrakis (triphenylphosphine) palladium at reflux for 5 days. The mixture was absorbed onto silica and chromatographed to give the title compound (1.25 g); δH [$^2$H$_6$]DMSO 10.20 (1H, s), 9.15(1H, s), 8.65(1H, s), 8.24(1H, s), 8.18(2H, m), 7.89(1H, s), 7.70(2H, m), 7.30(5H, m), 5.70(2H, s); m/z (M+1)$^+$ 377.

1-Methyl-5-(1,3-dioxolan-2-yl)-imidazole

1-Methyl-5-formyl imidazole (0.64 g) was treated with ethylene glycol (0.3 ml), p-toluenesulphonic acid monohydrate (0.0015 g) and powdered 4A molecular seives under N$_2$ for 18 hours at reflux. Subsequent cooling and filtration was followed by washing of the organic phase with aqueous sodium carbonate solution (2N), drying and concentration to give the title compound; δH (CDCl$_3$) 7.43 (1H, s), 7.12 (1H, s), 5.91 (1H, s), 4.10(4H, m), 3.70(3H, s).

5-Cyano-3-methylthio-2-oxoindole

Sulphuryl chloride (3.4 ml, 5.71 g, 42.4 mmol) was added via syringe to a stirred solution of ethyl 2-(methylthio)

acetate (5.4 ml, 5.63 g, 42.0 mmol) in dry dichloromethane (30 ml) cooled to −78° C., under a nitrogen atmosphere. After stirring for 15 min, a solution of 4-cyanoaniline (5.0 g, 42.3 mmol) and 1,8-bis(dimethylamino) naphthalene (9.0 g, 42.0 mmol) in dry dichloromethane (50 ml) was added maintaining the temperature at −78° C. Stirring was continued for 3 hours at −78° C., and then triethylamine (5.9 ml, 4.28 g, 42.3 mmol) was added at −78° C., and then the mixture was allowed to warm to room temperature. Stirring was continued under a nitrogen atmosphere for 3 days. Glacial acetic acid (5.0 ml, 5.25 g, 87.3 ml) was then added and the mixture was stirred for 1 hour. The reaction mixture was washed with 8%aq. NaHCO$_3$ (50 ml) and water (2×100 ml), dried (Na$_2$CO$_3$), and concentrated in vacuo. Silica gel chromatography, eluting with 1:2 ethyl acetate/i-hexane, gave 5-cyano-3-methylthio-2-oxoindole as a yellow solid (2.8 g, 13.7 mmol, 32%); δH CDCl$_3$ 8.95 (1H, br s), 7.67 (1H, s). 7.60 (1H, d), 7.01 (1H, d), 4.30 (1H, s), 2.08 (3H, s).

2-Amino-5-cyanobenzoic acid

Air was bubbled through a stirred solution of 5-cyano-3-methylthio-2-oxoindole (18.0 g, 88.1 mmol) and potassium hydroxide (5.9 g, 105.2 mmol) in a 9:1 mixture of methanol:water at room temperature for 5 hours. Further potassium hydroxide (5.9 g, 105.2 mmol) was added and the air bubbling continued overnight. The methanol was removed in vacuo, and the residue was carefully acidifed with 2N aq. HCl. The resulting precipitate was collected by filtration, and triturated with ethyl acetate to give 2-amino-5-cyanobenzoic acid as a pale brown solid (4.8 g, 29.6 mmol, 34%); δH [$^2$H$_6$]DMSO 8.02 (1H, d), 7.55 (1H, dd), 7.50 (2H, br s), 6.86 (1H, d).

6-Cyano-quinazolinone

A stirred solution of 2-amino-5-cyanobenzoic acid (2.0 g, 12.3 mmol) in formamide (10 ml) was heated at 190° C. for 7 hours. The dark solution was allowed to cool and poured into water (50 ml). The resulting precipitate was collected by filtration and dried in vacuo at 60° C. to give 6-cyanoquinazolinone (0.93 g, 5.43 mmol, 44%); [$^2$H$_6$]DMSO 12.65 (1H, s), 8.50 (1H, s), 8.28 (1H, s), 8.18 (1H, dd), 7.81(1H, d).

(4-Benzyloxy-phenyl)-(6-(trimethylsilylethynyl)quinazolin-4-yl)-amine

The (4-benzyloxy-phenyl)-(6-iodoquinazolin-4-yl)-amine hydrochloride (1.0 g, 2.04 mmol) was reacted with trimethylsilylacetylene (8.0 ml, 5.56 g, 5.66 mmol), triethylamine (5.0 ml, 3.63 g, 3.58 mmol), bis(triphenylphosphine) palladium (II) chloride (0.10 g, 0.14 mmol) and copper(I) iodide (0.10 g, 0.53 mmol) at room temperature in acetonitrile (15 ml) under a nitrogen atmosphere overnight. Purification by silica gel chromatography (eluting with 50% i-hexane/EtOAc) gave the title compound as an off-white solid (0.70 g, 1.65 mmol, 81%).

(4-Benzyloxy-phenyl)-(6-ethynylquinazolin-4-yl)-amine

The (4-benzyloxy-phenyl)-(6-(trimethylsilylethynyl) quinazolin-4-yl)-amine (0.65 g, 1.53 mmol) was reacted with tetrabutylammonium fluoride in tetrahydrofuran (1.0 M, 5.0 ml, 5.0 mmol) at room temperature for 20 min. The solvent was removed in vacuo, and the residual oil was partitioned between water (20 ml) and ethyl acetate (20 ml). After separation, the aqueous was extracted with further ethyl acetate (2×20 ml). The combined organic solutions were dried (Na$_2$SO$_4$) and concentrated in vacuo to give the title compound as an off-white solid (0.43 g, 1.22 mmol, 80%).

N-Methyl-N-(2-methylsulphonylethyl)amine hydrochloride

Methylvinyl sulphone (2.1 g, 19.78 mmol) and methylamine (33% solution in IMS, 40 ml, excess) were mixed and heated at reflux under a nitrogen atmosphere for 6 hours. After standing overnight at room temperature, the mixture was concentrated in vacuo to give a yellow oil, which was treated with ethereal HCl to give a sticky solid. Trituration with absolute ethanol gave the title compound as a white solid which was collected by filtration and dried at 60° C. in vacuo (1.01 g, 5.82 mmol, 29%); δH [$^2$H$_6$]DMSO 9.27 (2H, br s), 3.59 (2H, dd), 3.31 (2H, dd), 3.12 (3H, s), 2.57 (3H, s).

N-[2-(Methylsulphonamido)ethyl]acetamide

N-Acetyethylenediamine (10.2 g, 100 mmol) and triethylamine (15 ml, 10.9 g, 108 mmol) were dissolved in dichloromethane (300 ml) and the solution cooled to 0° C. Methane sulphonyl chloride (8 ml, 11.8 g, 103 mmol) was dissolved in dichloromethane (10 ml) and added dropwise, and stirring was continued at 0° C. for 3 hours. The dichloromethane was removed in vacuo, and the residue was suspended in a mixture of ether and acetone, removing the insoluble material by filtration. The filtrate was concentrated in vacuo to give the title compound as a pale brown gum (14.5 g, 88.3 mmol, 88%); δH [$^2$H$_6$]DMSO 7.93 (1H, br t), 7.05 (1H, t), 3.11 (2H, t), 2.97 (2H, t), 2.89 (3H, s), 2.09 (3H, s).

2-(Methylsulphonamido)ethylamine hydrochloride

N-[2-(Methylsulphonamido)ethyl]acetamide (14.5 g, 88.3 mmol) and concentrated hydrochloric acid (100 ml) were dissolved in water (100 ml) and heated to reflux for a total of 3 hours. After cooling, the water was removed in vacuo, and the residue was left for several days at room temperature until crystallisation was underway. Trituration with a mixture of ethanol and ether gave the title compound as a white solid which was dried in vacuo at 60° C. (7.5 g, 42.9 mmol, 49%); δH [$^2$H$_6$]DMSO 8.22 (2H, br s), 7.42 (1H, t), 3.23 (2H, q), 2.87 (3H, s), 2.85–2.95 (2H, m).

2-Phthalamidoethylsulphonamide

2-Phthalamidoethylsulphonyl chloride (prepared as described in J. Am. Chem. Soc., 69,1393–1401, (1947)) (10.0 g, 36.5 mmol) was added to conc. aqueous ammonia solution (0.880 Mol, 120 ml), cooled to 0° C. The mixture was stirred at 0° C. for 30 min and then at room temperature for 2 hours. Concentration in vacuo, followed by trituration with water gave 2-phthalamidoethylsulphonamide as a white solid (3.70 g, 14.6 mmol, 40%); δH [$^2$H$_6$]DMSO 7.80–7.92 (4H, m), 7.03 (2H, br s), 3.96 (2H, dd), 3.30–3.38 (2H, m, obscured by water).

2-Aminoethylsulphonamide hydrochloride

2-Phthalamidoethylsulphonamide (3.68 g, 14.5 mmol) was suspended in ethanol (50 ml) and hydrazine hydrate (0.70 g, 71.5 mmol) was added. The mixture was heated to reflux for 4 hours. The mixture was partially concentrated in vacuo, diluted with water, acidified to pH 1 with 2N HCl, and filtered. The filtrate was concentrated in vacuo to give a white solid. Treatment with more 2N HCl, followed by trituration with a mixture of ethanol and acetone gave the title compound as a white solid (1.0 g, 6.23 mmol, 43%); δH D$_2$O 3.60–3.69 (2H, m), 3.50–3.58 (2H, m).

(3-Methyl-3-oxetane)methyl 2-furoate

2-Furoic acid (9.0 g, 80.3 mmol) was added to a solution of 3-methyl-3-oxetanemethanol (16.5 g, 161.6 mmol), 1,3-dicyclohexylcarbodiimide (25.0 g, 121.1 mmol) and DMAP (0.50 g, 4.1 mmol) in dichloromethane (250 ml), and the mixture was stirred under a nitrogen atmosphere overnight. The mixture was filtered and the filtrate was concentrated in vacuo to give an oil. Crystallisation from ethanol/water gave a white solid collected by filtration and shown by NMR to be 2-furoic acid. The filtrate was concentrated in vacuo to remove the ethanol, and the resulting aqueous solution was extracted with dichloromethane (×2). This solution was dried (MgSO$_4$) and concentrated to give the title compound as a colourless oil (11.8 g, 60.1 mmol, 75%); δH [$^2$H$_6$]DMSO 8.00 (1H, s), 7.34 (1H, d), 7.71 (1H, dd), 4.44 (2H, d), 4.35 (2H, s), 4.28 (2H, d), 1.31 (3H, s).

2-(4-Methyl-2,6,7-trioxabicyclo[2.2.2]oct-1-yl)furan (3-Methyl-3-oxetane)-methyl-2-furoate (11.8 g, 60.1 mmol) was dissolved in dichloromethane (250 ml) and the solution was cooled to 0° C. Boron trifluoride-etherate (10 drops) was added and the mixture stirred at room temperature, and then left to stand for two months. Triethylamine (0.5 ml, 0.36 g, 3.6 mmol) was added and the mixture concentrated to give a sticky white solid. Trituration with ether/acetone gave the title compound as a white solid (2.2 g, 11.2 mmol, 19%); δH [$^2$H$_6$]DMSO 8.00 (1H, s), 7.34 (1H, d), 7.71 (1H, dd), 4.44 (2H, d), 4.35 (2H, s), 4.28 (2H, d), 1.31 (3H, s).

5-(4-Methyl-2,6,7-trioxabicyclo[2.2.2]oct-1-yl)-2-[tri(n-butyl)stannyl]furan 2-(4-Methyl-2,6,7-trioxabicyclo[2.2.2]oct-1-yl)furan (2.0 g, 10.2 mmol) was dissolved in THF (20 ml) and the solution was cooled to −78° C. n-BuLi (1.6 M solution in hexanes, 7.7 ml, 12.32 mmol) was added and the mixture stirred at −78° C. for 30 min, allowed to warm to 0° C. for 20 min. and then recooled to −78° C. The tributyltin chloride (3.5 ml, 4.68 g, 14.4 mmol) was added and stirring was continued at −78° C. for 15 min. The mixture was allowed to warm gradually to room temperature and stirring continued for three days. The reaction was quenched by the addition of water, and extracted with ethyl acetate. This solution was washed with water, dried (MgSO$_4$), and concentrated in vacuo to give the title compound as a yellow oil (4.7 g, 9.7 mmol, 95%); δH [$^2$H$_6$]DMSO 6.52 (1H, d), 6.38 (1H, d), 3.96 (6H, s), 0.77–1.63 (30H, m).

(4-Benzyloxy-phenyl)-(6-[5-(4-methyl-2,6,7-trioxabicyclo[2.2.2]oct-1-yl)furan-2-yl]quinazolinyl)-amine (4-Benzyloxy-phenyl)-(6-iodoquinazolin-4-yl)-amine (0.925 g, 2.04 mmol), 5-(4-methyl-2,6,7-trioxabicyclo[2.2.2]oct-1-yl)-2-[tri(n-butyl)stannyl]furan (2.00 g, 4.1 mmol) and bis(triphenylphosphine)palladium (II) chloride (catalytic) were reacted in dry dioxane (25 ml) according to Procedure B. Purification by silica gel chromatography and eluting with 100% EtOAc gave the title compound as a yellow solid (0.700 g, 1.34 mmol, 66%); δH [$^2$H$_6$]DMSO 10.0 (1H, s), 8.75 (1H, s), 8.48 (1H, s), 8.12 (1H, d), 7.79 (1H, d), 7.66 (2H, d), 7.30–7.52 (5H, m), 7.03–7.12 (3H, m), 6.64 (1H, d), 5.14 (2H, s), 4.06 (6H, s), 0.85 (3H, s).

(4-(4-Benzyloxyanilino)quinazolin-6-yl)-(N-hydroxycarboximidamide)

Sodium hydroxide (0.62 g, 15.5 mmol) and hydroxylamine hydrochloride (1.03 g, 14.8 mmol) were added to a solution of (4-benzyloxy-phenyl)-(6-cyanoquinazolin-4-yl)-amine (0.472 g, 1.34 mmol) in ethanol (30 ml), and the resulting mixture was heated to reflux overnight. After cooling, the mixture was concentrated in vacuo. The residue was washed thoroughly with water, and then with a little ether and dried in vacuo to give the title amidoxime (0.452 g, 1.18 mmol, 88%); δH [$^2$H$_6$]DMSO 9.88 (1H, s), 9.73 (1H, s), 8.72 (1H, s), 8.52 (1H, s), 8.13 (1H, d), 7.67–7.78 (3H, m), 7.31–7.52 (5H, m), 7.07 (2H, d), 6.65 (2H, s), 5.14 (2H, s); m/z (M+1$^+$) 386.

(4-(1-Benzyl-1H-indazol-5-yl)quinazolin-6-yl)-(N-hydroxycarboximidamide)

Sodium hydroxide (0.563 g, 14.1 mmol) and hydroxylamine hydrochloride (0.931 g, 13.4 mmol) were added to a solution of (1-benzyl-1H-indazol-5-yl)-(6-cyanoquinazolin-4-yl)-amine (0.504 g, 1.34 mmol) in ethanol (40 ml), and the resulting mixture was heated to reflux overnight. After cooling, the mixture was concentrated in vacuo. The residue was washed thoroughly with water, and then with a little ether and dried in vacuo to give the title amidoxime (0.452 g, 1.10 mmol, 82%); δH [$^2$H$_6$]DMSO 9.87 (2H, m), 8.76 (1H, s), 8.54 (1H, s), 8.23 (1H, s), 8.10–8.18 (2H, m), 7.65–7.80 (3H, m), 7.18–7.38 (5H, m), 5.96 (2H, s), 5.68 (2H, s); m/z (M+1$^+$) 410.

N-(2-Methylthioethyl)-trifluoroacetamide

Trifluoroacetic anhydride (17 ml, 25.28 g, 120.6 mmol) was added dropwise to a solution of 2-methylthioethylamine (10.0 g, 109.7 mmol) and triethylamine (16.8 ml, 12.2 g, 120.5 mmol) in anhydrous dichloromethane (50 ml) cooled to 0° C. using an ice bath. On completion of the addition, the reaction was stirred at room temperature under a nitrogen atmosphere for 18 hours. Water (200 ml) was added, the layers were separated, and the aqueous was extracted with further dichloromethane (100 ml). The combined dichloromethane solutions were dried (MgSO$_4$), and concentrated in vacuo to give the title compound as a yellow oil (19.0 g, 109.7 mmol, 100%); δH CDCl$_3$ 6.8 (1H, br s), 3.59 (2H, q), 2.72 (2H, t), 2.13 (3H, s).

N-(2-Methylsulphonylethyl)-trifluoroacetamide

A solution of N-(2-methylthioethyl) trifluoroacetamide (19.0 g, 109.7 mmol) in methanol (200 ml) was cooled to 0° C. using an ice bath. A suspension of Oxone™ (2KHSO$_5$·KHSO$_4$·K$_2$SO$_4$) (74.19 g, 120.67 mmol) in water (100 ml) was added portionwise over 10 minutes, and the reaction was stirred at room temperature for 24 hours. The methanol was removed in vacuo, water (600 ml) was added and the mixture was extracted with dichloromethane (3×300 ml). The combined extracts were dried (MgSO$_4$), and concentrated in vacuo to give the title compound as a white solid (12.42 g, 56.7 mmol, 52%); δH CDCl$_3$ 7.33 (1H, br s), 3.93 (2H, q), 3.31 (2H, t), 3.02 (3H, s).

N-(Ethoxycarbonylmethyl)-N-(2-methylsulphonylethyl)-trifluoroacetamide

Sodium hydride (60% dispersion in mineral oil, 0.190 g, 4.75 mmol) was added to a solution of N-(2-methylsulphonylethyl)trifluoroacetamide (0.986 g, 4.50 mmol) in dry DMF (10 ml) and the mixture was stirred under a nitrogen atmosphere for 30 minutes. Ethyl bromoacetate (0.55 ml, 0.828 g, 4.96 mmol) was added and the mixture was stirred at room temperature overnight. The mixture was poured into ice-water, and extracted with ethyl acetate. This solution was washed with water, dried (MgSO$_4$), and concentrated in vacuo to give the title compound as a white solid (1.239 g, 4.03 mmol, 90%); δH CDCl$_3$ 4.17 (4H, m), 3.91 (2H, t), 3.46 (2H, t), 2.98 (3H, s), 1.30 (3H, t).

Methyl 2-(4-piperidon-1-yl)acetate

A solution of methyl bromoacetate (13.6 ml, 21.98 g, 144 mmol) in acetonitrile (20 ml) was added to a mixture of 4-piperidone monohydrate hydrochloride (20 g, 130 mmol) and potassium carbonate (36 g, 260 mmol) in more acetonitrile (100 ml). The mixture was heated at reflux under a nitrogen atmosphere for 18 hours. The solvent was removed in vacuo and the residue was partitioned between EtOAc and water, and the aqueous extratced with further EtOAc. The organic solution was washed with brine, dried (Na$_2$SO$_4$), and concentrated in vacuo to give methyl 2-(4-piperidon-1-yl)acetate as a yellow oil (14.29 g, 83.5 mmol, 64%); tlc (SiO$_2$, 1:1 EtOAc/hexane, Rf=0.23).

1-(N,N-Dimethylaminopropyl)-imidazole

Imidazole (10.9 g) was treated with sodium hydroxide (10.9 g) in acetonitrile (80 ml) at room temperature for 30 minutes. Tetra-N-butyl ammonium hydrogen sulphate (2.16 g) was added and 3-N,N-dimethylaminopropyl chloride hydrochloride (27.19 g). After 24 hours at reflux, the cooled mixture was concentrated, filtered and concentrated in vacuo. Chromatography on silica gave the title compound (19.82 g) as a red oil; δH CDCl$_3$ 7.48 (1H, s), 7.04 (1H, s), 6.91 (1H, s), 4.01 (2H, t), 2.11 (6H, s), 2.10 (2H, t), 1.91 (2H, m).

1-(N,N-Dimethylaminopropyl)-5-tri-n-butylstannylimidazole 1-(N,N-Dimethylaminopropyl)-imidazole (3 g) was added to a mixture of TMEDA (7 ml) and n-butyl lithium (29.4 ml, 1.6 M) in n-hexane (25 ml) at −20° C. under nitrogen. After 30 minutes at −20° C. and 30 minutes at 20° C., the mixture was recooled to −20° C. and tri-n-butylstannyl chloride (13.05 ml) was added dropwise. The mixture was allowed to warm to 20° C. and stirred there for 20 hours. The mixture was partitioned between ethyl acetate and water, the aqueous phase was extracted with ethyl acetate and combined organic extracts were dried and concentrated. Purification by flash chromatography gave the title compound (2.10 g); δH CDCl$_3$ 7.70 (1H, s), 7.01 (1H, s), 3.98 (2H, t), 2.20(6H, s), 2.20 (2H, t), 1.90 (2H, m) 1.55 (6H, m), 1.37 (12H, m), 0.92 (9H, m).

1-(N,N-Dimethylaminopropyl)-2-tri-n-butylstannylimidazole 1-(N,N-Dimethylaminopropyl) imidazole (2 g) in THF (20 ml) at −78° C. was treated with nBuLi (8.6 ml, 1.6 M) under nitrogen. After 30 minutes at −78° C., tri-n-butylstannyl chloride was added and the mixture allowed to warm to 20° C. The mixture was concentrated in vacuo, taken up in n-hexane and filtered. The filtrate was concentrated in vacuo to give the title compound (4.33 g) as a yellow oil; δH CDCl$_3$ 7.28 (1H, s), 7.09 (1H, s), 3.97 (2H, t), 2.25 (2H, t), 2.20(6H, s), 1.90 (2H, m) 1.55 (6H, m), 1.34 (12H, m), 0.92 (9H, m).

(4-Hydroxy-quinazolin-7-yl)-carboxylic acid

3-Amino-1,4-dibenzoic acid (8.6 g) was heated at 180° C. in formamide (30 ml) for 2 hours. The mixture was allowed to cool and filtered, washing with acetone to give the title compound (9.1 g); R.T. (LC), 3.33 mins.

4-Hydroxy quinazoline-7-hydrazide (4-Hydroxy-quinazolin-7-yl)-carboxylic acid (0.5 g) in dry THF (20 ml) was treated with carbonyl diimidazole (0.85 g) under nitrogen for 6 hours at room temperature. Hydrazine hydrate was added and stirring was continued for 18 hours. The mixture was filtered to give the title compound (0.41 g); m/z (M+1+) 205.

7-(5-Methyl-[1,3,4]oxadiazol-2-yl)quinazolin-4-one

4-Hydroxy quinazoline-7-hydrazide (0.41 g) was treated with triethyl orthoacetate (10 ml) at reflux under nitrogen for 24 hours. The mixture was cooled, filtered and purified by chromatography to give the title compound (0.09 g); m/z (M+1+) 229.

4-Chloro-7-(5-methyl-[1,3,4]oxadiazol-2-yl)quinazoline 7-(5-Methyl-[1,3,4]oxadiazol-2-yl)quinazolin-4-one (0.09 g) was treated with phosphorous oxychloride (5 ml) at reflux under nitrogen for 2 hours. The mixture was cooled, evaporated and partitioned between saturated aqueous sodium carbonate and ethyl acetate. The organic phase was dried, concentrated in vacuo to give the title compound which was used crude in the subsequent synthetic step.

7-Iodoquinazolin-4-one

7-Amino-quinazolin-4-one (R. Dempcy and E. Skito, Biochemistry, 30, 1991, 8480) (1.61 g) was suspended in 6N HCl (20 ml) and cooled in an ice bath. A solution of sodium nitrite (0.75 g) in water (10 ml) was added dropwise over 15 minutes. After a further 10 minutes, a solution of potassium iodide (1.66 g) in water (5 ml) was added dropwise. The mixture was warmed to 20° C. and after 3 hours partitioned between ethyl acetate and sodium thiosulphate. The organic phase was dried and concentrated in vacuo to give the title compound (0.485 g); m/z (M+1+) 271.

4-Chloro-7-iodoquinazoline

7-Iodoquinazolin-4-one (0.46 g) was treated with phosphorous oxychloride (5 ml) at reflux under nitrogen for 2 hours. The mixture was cooled, evaporated and partitioned between saturated aqueous sodium carbonate and ethyl acetate. The organic phase was dried and concentrated in vacuo to give the title compound (0.43 g); m/z (M+1+) 291.

(1-Benzyl-1H-indazol-5-yl)-(7-iodoquinazolin-4-yl)-amine hydrochloride

4-Chloro-7-iodoquinazoline (0.42 g) was treated with 1-benzyl-1H-indazol-5-ylamine (0.323 g) in acetonitrile (20 ml) at reflux under nitrogen for 18 hours (Procedure A). The mixture was cooled and filtered to give the title compound (0.57 g); m/z (M+1+) 478.

EXAMPLES

Example 1

(4-Benzyloxy-phenyl)-(6-furan-2-yl-quinazolin-4-yl)-amine (Procedure B)

The (4-benzyloxy-phenyl)-(6-bromo-quinazolin-4-yl)-amine (300 mg, 0.74 mmol), 2-(tributylstannyl)furan (290 mg, 0.81 mmol) and bis(triphenylphosphine) palladium(II) chloride (catalytic) were dissolved in dioxane (3.5 ml) and heated at reflux under nitrogen for 2 hr. The cooled reaction mixture was absorbed onto silica and purified by flash column chromatography (silica gel, eluting with 1:1 ethyl acetate/iso-hexane) to give the title product (290 mg, 79%) as a pale yellow solid; δH [$^2$H$_6$]-DMSO 9.94 (1H, b, NH), 8.85 (1H, s, 5-H), 8.53 (1H, s, 2-H), 8.21 (1H, d, 7-H), 7.91 (1H, d, furan-H), 7.81 (1H, d, 8-H), 7.72 (2H, d, 2'-H, 6'-H), 7.57–7.33 (5H, m, 5×Ph-H), 7.16 (1H, d, furan-H), 7.10 (2H, d, 3'-H, 5'-H), 6.72, (1H, dd, furan-4H), 5.17 (2H, s, CH$_2$); m/z 394 (M+1)$^+$.

Example 2

(4-Benzyloxy-phenyl)-(6-(thiophen-2-yl)-quinazolin-4-yl)-amine (Procedure B)

The (4-benzyloxy-phenyl)-(6-bromoquinazolin-4-yl)-amine (200 mg, 0.49 mmol), 2-(tributylstannyl)thiophene (200 mg, 0.53 mmol) and bis(triphenylphosphine)palladium (II) chloride (catalytic) were dissolved in dioxan (3 ml) and heated at reflux under nitrogen for 4 hr. The cooled reaction mixture was absorbed onto silica and purified by flash column chromatography (silica gel, eluting with an ethyl acetate/iso-hexane gradient). The resulting solid was triturated with iso-hexane/ethyl acetate to give the product (120 mg, 60%) as a pale yellow solid; δH [$^2$H$_6$]-DMSO 9.88 (1H, b, NH), 8.76 (1H, s, 5-H), 8.49 (1H, s, 2-H), 8.12 (1H, d, 7-H), 7.82–7.60 (5H, m, thiophene-3-H, thiophene-5-H, 8-H, 2'-H, 6'-H), 7.52–7.30 (5H, m, 5×Ph-H), 7.23 (1H, t, thiophene-4H), 7.18 (2H, d, 3'-H, 5'-H), 5.11 (2H, s, CH$_2$); m/z 410 (M+1)$^+$.

Example 3

(4-Benzyloxy-phenyl)-(6-(pyridin-2-yl)-quinazolin-4-yl)-amine (Procedure B)

The (4-benzyloxy-phenyl)-(6-bromoquinazolin-4-yl)-amine (200 mg, 0.49 mmol), 2-(tributylstannyl)pyridine (200 mg, 0.53 mmol) and bis(triphenylphosphine)palladium (II) chloride (catalytic) were dissolved in dioxan (3 ml) and heated at reflux under nitrogen for 9 hr. The cooled reaction mixture was absorbed onto silica and purified by flash column chromatography (silica gel, eluting with an ethyl acetate/iso-hexane gradient). The resulting solid was triturated with iso-hexane/ethyl acetate to give the product (110 mg, 56%) as a pale yellow solid; δH [$^2$H$_6$]-DMSO 9.99 (1H, b, NH), 9.18 (1H, s, 5-H), 8.76 (1H, d, pyridine-H), 8.60 (1H, d, 7-H), 8.54 (1H, s, 2-H), 8.23 (1H, d, pyridine-H), 8.00 (1H, t, pyridine-H), 7.87 (1H, d, 8-H), 7.70 (2H, d, 2'-H, 6'-H), 7.53–7.31 (6H, m, 5×Ph-H, pyridine-H), 7.09 (2H, d, 3'-H, 5'-H), 5.14 (2H, s, CH$_2$); m/z 405 (M+1)$^+$.

Example 4

(4-Benzyloxy-phenyl)-(6-(pyrimidin-2-yl)-quinazolin-4-yl)-amine

The (4-benzyloxy-phenyl)-(6-bromoquinazolin-4-yl)-amine (200 mg, 0.49 mmol), 2-(tributylstannyl)pyrimidine (200 mg, 0.54 mmol) and bis(triphenylphosphine)palladium (II) chloride (catalytic) were dissolved in dioxan (3 ml) and heated at reflux under nitrogen for 27 hr (Procedure B). The solvent was removed from the cooled reaction under vacuum, and the residue was purified by flash column chromatography (silica gel, eluting with an ethyl acetate/iso-hexane gradient). The resulting oily solid was triturated with iso-hexane/ethyl acetate to give the product (80 mg, 40%) as a pale yellow solid; δH [$^2$H$_6$]-DMSO 10.30 (1H, b, NH), 9.61 (1H, s, 5-H), 9.07 (2H, d, pyrimidine 4-H, pyrimidine 6-H), 8.86 (1H, d, 7-H), 8.51 (1H, s, 2-H), 7.93 (1H, d, 8-H), 7.78 (2H, d, 2'-H, 6'-H), 7.65–7.36 (6H, m, 5×Ph-H, pyrimidine 5-H), 7.11 (2H, d, 3'-H, 5'-H), 5.18 (2H, s, CH$_2$); m/z 406 (M+1)$^+$.

Example 5

(4-Benzyloxy-phenyl)-(6-(5-(1,3-dioxolan-2-yl)-furan-2-yl)-quinazolin-4-yl)-amine (Procedure B)

The (4-benzyloxy-phenyl)-(6-bromoquinazolin-4-yl)-amine (1.5 g, 3.7 mmol), 5-(1,3-dioxolan-2-yl)-2-(tributylstannyl)-furan (1.9 g, 4.42 mmol) and bis(triphenylphosphine)palladium(II) chloride (catalytic) were dissolved in dioxan (30 ml) and heated at reflux under nitrogen for 6 hr. The solvent was removed from the cooled reaction under vacuum, and the residual oil was triturated with iso-hexane/ethyl acetate to give the product (1.07 g, 62%) as a pale yellow solid; δH [$^2$H$_6$]-DMSO 9.96 (1H, b, NH), 8.80 (1H, s, 5-H), 8.51 (1H, s, 2-H), 8.18 (1H, d, 7-H), 7.80 (1H, d, 8-H), 7.70 (1H, d, 2'-H, 6'-H), 7.58–7.30 (5H, m, 5×Ph-H), 7.10 (3H, m, 3'-H, 5'-H, furan 3-H), 6.78 (1H, d, furan 4-H), 6.12 (1H, s, CHO$_2$), 5.18 (2H, s, PhC$\underline{H}$$_2$), 4.22–3.94 (4H, m, 2×CH$_2$); m/z 466 (M+1)$^+$.

Example 6

(4-Benzyloxy-phenyl)-(6-(3-methyl-3H-imidazol-4-yl)-quinazolin-4-yl)-amine

The (4-benzyloxy-phenyl)-(6-bromoquinazolin-4-yl)-amine (1.0 g, 2.46 mmol), 1-methyl-5-(tributylstannyl)imidazole (prepared according to Gaare, K., et al. Acta Chem. Scand. (1993), 47(1), 57–62) (1.25 g, 3.37 mmol) and bis(triphenylphosphine)palladium (II) chloride (catalytic amount) were reacted according to Procedure B in dioxane (50 ml) for 3 hours. The solvent was removed in vacuo, and the solid was washed with i-hexane. The resulting dark solid was suspended in IMS, and undissolved material removed by filtration. The resulting filtrate was concentrated in vacuo to give the product as a pale baige solid (0.90 g, 2.21 mmol, 90%); δH [$^2$H$_6$]-DMSO 9.69 (1H, b, NH), 8.60 (1H, s, 5-H), 8.55 (1H, s, 2-H), 8.00 (1H, d, 7-H), 7.83 (2H, m, 8-H, imidazole-H), 7.69 (2H, d, 2'-H, 6'-H), 7.52–7.33 (5H, m, 5×Ph-H), 7.22 (1H, s, imidazole-H), 7.09 (2H, d, 3'-H, 5'-H), 5.14 (2H, s, CH$_2$), 3.80 (3H, s, CH$_3$); m/z 408 (M+1)$^+$.

Example 7

(4-Benzyloxy-phenyl)-(6-(2,3-dihydrofuran-5-yl)-quinazolin-4-yl)-amine

The (4-benzyloxy-phenyl)-(6-bromoquinazolin-4-yl)-amine (200 mg, 0.49 mmol), 5-(tributylstannyl)-2,3-dihydrofuran (250 mg, 0.70 mmol) and bis(triphenylphosphine)palladium(II) chloride (catalytic) were dissolved in dioxan (10 ml) and heated at reflux under nitrogen for 2 hr (Procedure B). The solvent was removed from the cooled reaction under vacuum, and the residue was suspended in 1:1 iso-hexane/ethyl acetate and filtered. The solvent was removed from the filtrate under vacuum to give the product (140 mg, 72%) as a yellow solid; δH [$^2$H$_6$]-DMSO 9.88 (1H, b, NH), 8.62 (1H, s, 5-H), 8.50 (1H, s, 2-H), 8.05 (1H, d, 7-H), 7.67 (3H, m, 8-H, 2'-H, 6'-H), 7.55–7.29 (5H, m, 5×Ph-H), 7.03 (2H, m, 3'-H, 5'-H), 5.81 (1H, s, 3"-H), 5.12 (2H, s, PhC$\underline{H}$$_2$), 4.52 (2H, t, 5"-H$_2$), 2.88 (2H, t, 4"-H$_2$); m/z 396 (M+1)$^+$.

Example 8

(4-Benzyloxy-phenyl)-(6-(3-methyl-1,2,3-triazol-4-yl)-quinazolin-4-yl)-amine (Procedure B)

The (4-benzyloxy-phenyl)-(6-bromoquinazolin-4-yl)-amine (250 mg, 0.62 mmol), 1-methyl-5-(tributylstannyl)-1,2,3-triazole (300 mg, 0.81 mmol) and bis(triphenylphosphine)palladium(II) chloride (catalytic) were dissolved in dioxan (10 ml) and heated at reflux under nitrogen for 48 hr. The solvent was removed from the cooled reaction under vacuum. The resulting material was dissolved in ethyl acetate, filtered and the filtrate evaporated to dryness. Trituration with ethyl acetate/iso-hexane gave the product (115 mg, 45%) as a beige solid; δH [$^2$H$_6$]-DMSO 9.90 (1H, b, NH), 8.76 (1H, s, 5-H), 8.61 (1H, s, 2-H), 8.10 (2H, m, 7-H, triazole-H), 7.92 (1H, d, 8-H), 7.70 (2H, d, 2'-H, 6'-H), 7.58–7.38 (5H, m, 5×Ph-H), 7.12 (2H, d, 3'-H, 5'-H), 5.19 (2H, s, CH$_2$), 4.22 (3H, s, CH$_3$); m/z 409 (M+1)$^+$.

Example 9

5-(4-(4-Benzyloxy-phenylamino)-quinazolin-6-yl)-furan-2-carbaldehyde

The 4-(4-benzyloxy-phenylamino)-(6-(5-(1,3-dioxolan-2-yl)-furan-2-yl)-quinazolin-4-yl)-amine (1.0 g, 2.1 mmol) was dissolved in THF (20 ml) and hydrochloric acid (2N, 10 ml) was added. The reaction was stirred at room temperature for 1 hr. The precipitate which formed was collected by filtration and washed with acetone, then partitioned between ethyl acetate, triethylamine and water. The organic phase was washed with water, dried (magnesium sulphate) and the solvent was removed under vacuum. Trituration with iso-hexane/ethyl acetate gave the product as an orange solid (610 mg, 69%); δH [$^2$H$_6$]-DMSO 10.05 (1H, b, NH), 9.62 (1H, s, CHO), 8.95 (1H, s, 5-H), 8.48 (1H, s, 2-H), 8.24 (1H, d, 7-H), 7.80 (1H, d, 8-H), 7.70 (1H, d, furan 4-H), 7.59 (2H, d, 2'-H, 6'-H), 7.48–7.25 (6H, m, 5×Ph-H, furan 3-H), 7.02 (2H, m, 3'-H, 5'-H), 5.09 (2H, s, CH$_2$); m/z 422 (M+1)$^+$.

5-(4-(4-Benzyloxy-phenylamino)-quinazolin-6-yl)-furan-2-carbaldehyde hydrochloride 4-(4-Benzyloxy-phenylamino)-(6-(5-(1,3-dioxolan-2-yl)-furan-2-yl)-quinazolin-4-yl)-amine (6.70 g, 14.4 mmol) was stirred at room temperature in a mixture of THF (70 ml) and 2N aqueous HCl (70 ml) for 1 hour. The THF was removed in vacuo and the resulting precipitate was collected by filtration and washed with water to give the hydrochloride salt as a yellow solid (6.50 g, 14.1 mmol, 98%); δH ($^2$H$_6$]DMSO 12.15 (1H, s), 9.69 (1H, s) 9.58 (1H, s), 8.88 (1H, s), 8.50 (1H, dd), 8.02 (1H, d), 7.77 (1H, d), 7.62–7.74 (3H, m), 7.31–7.52 (5H, m), 7.15 (2H, d), 5.17 (2H, s).

Example 10

(4-Benzyloxy-phenyl)-(6-(5-(4-methylpiperazin-1-ylmethyl)-furan-2-yl)-quinazolin-4-yl-amine 5-(4-(4-Benzyloxy-phenylamino)-quinazolin-6-yl)-furan-2-carbaldehyde (0.19 g) and 1-methylpiperazine (0.056 g) were mixed in dichloromethane (0.6 ml) and stirred at room temperature for 5 mins. The mixture was chilled to 0° C. and sodium triacetoxyborohydride (0.5 g) added in portions with stirring. The reaction was stirred at 0° C. for 2 hr. The reaction was quenched with water and extracted with dichloromethane (×2). The combined organic fractions were dried (magnesium sulphate) and the solvent removed under vacuum. The resulting orange glass was triturated with ethyl acetate/iso-hexane. The solid produced was filtered off and dried at 60° C. under vacuum to give the product as a yellow solid (0.11 g); δ H [$^2$H$_6$]-DMSO 10.89 (1H, b), 8.70 (1H, s), 8.47 (1H, s), 8.11 (1H, d), 7.77 (1H, d), 7.66 (2H, d), 7.50–7.30 (5H, m), 7.12–7.00 (3H, m), 6.50 (1H, d), 5.13 (2H, s), 3.58 (2H, s), 2.53–2.22 (8H, m), 2.12 (3H, s); m/z 506 (M+1)$^+$.

Example 11

(S)-1-(5-(4-(4-Benzyloxy-phenylamino)-quinazolin-6-yl)-furan-2-ylmethyl)-pyrrolidine-2-carboxylicacid amide 5-(4-(4-Benzyloxy-phenylamino)-quinazolin-6-yl)-furan-2-carbaldehyde and L-prolinamide were reacted in an analogous manner to Example 10 to give the title compound; δH

[$^2$H$_6$]-DMSO 9.85 (1H, b), 8.72 (1H, s), 8.50 (1H, s), 8.14 (1H, d), 7.79 (1H, d), 7.71 (2H, d), 7.54–7.31 (5H, m), 7.24 (1H, s), 7.17 (1H, s), 7.09 (2H, d), 7.02 (1H, d), 6.53 (1H, d), 5.15 (2H, s), 3.82 (2H, s), 3.42 (1H, b), 3.12 (2H, b), 1.85–1.67 (4H, m); m/z 520 (M+1)$^+$.

Acidification with ethereal HCl gave a yellow precipitate, which was dissolved in MeOH. This solution was concentrated in vacuo and the residue was triturated with ether to give the product as a yellow solid which was dried at 60° C. in vacuo to give the hydrochloride salt as a yellow solid; δH [$^2$H$_6$]DMSO 12.35 (1H, s), 9.64 (1H, s), 8.86 (1H, s), 8.42 (1H, d), 8.30 (1H, s), 8.00 (1H, d), 7.68–7.76 (3H, m), 7.31–7.55 (6H, m), 7.14 (2H, d), 6.89 (1H, d), 5.18 (2H, s), 4.57 (2H, s), 3.50–3.70 (3H, m), 1.80–2.10 (4H, m); m/z (M+1$^+$) 520.

Example 12

N2-(5-(4-(4-Benzyloxy-phenylamino)-quinazolin-6-yl)-furan-2-ylmethyl)-N1,N1-dimethyl-propane-1,2-diamine 5-(4-(4-Benzyloxy-phenylamino)-quinazolin-6-yl)-furan-2-carbaldehyde and N,N-dimethyl-1,2-propanediamine were reacted in an analogous manner to Example 10 to give the title compound; δH [$^2$H$_6$]-DMSO 9.83 (1H, b,), 8.70 (1H, s), 8.42 (1H, s), 8.10 (1H, d), 7.73 (1H, d), 7.64 (2H, d), 7.50–7.28 (5H, m), 7.02 (2H, d), 6.99 (1H, d), 6.52 (1H, d), 5.10 (2H, s), 3.93–3.70 (2H, m), 2.04 (9H, m), 0.92 (3H, m); m/z 508 (M+1)$^+$.

Example 13

N-(5-(4-(4-Benzyloxy-phenylamino)-quinazolin-6-yl)-furan-2-ylmethyl)-N-ethyl-N',N'-dimethyl-ethane-1,2-diamine 5-(4-(4-Benzyloxy-phenylamino)-quinazolin-6-yl)-furan-2-carbaldehyde and N-ethyl-N',N'-dimethyl-ethane-1,2-diamine were reacted in an analogous manner to Example 10 to give the title compound; δH [$^2$H$_6$]-DMSO 9.90 (1H, b), 8.79 (1H, s), 8.48 (1H, s), 8.12 (1H, d), 7.79 (1H, d), 7.70 (2H, d), 7.53–7.31 (5H, m), 7.12–7.02 (3H, m), 6.04 (1H, d), 5.13 (2H, s), 3.80 (2H, s), 2.68 (4H, s), 2.55 (2H, q), 2.36 (6H, s), 1.09 (3H, t); m/z 522 (M+1)$^+$.

Example 14

(4-Benzyloxy-phenyl)-(6-(5-(pyridin-3-ylaminomethyl)-furan-2-yl)quinazolin-4-yl)-amine 5-(4-(4-Benzyloxy-phenylamino)-quinazolin-6-yl)-furan-2-carbaldehyde and 3-aminopyridine were reacted in an analogous manner to Example 10 to give the title compound; δH [$^2$H$_6$]-DMSO 9.82 (1H, b), 8.70 (1H, s), 8.42 (1H, s), 8.11–8.01 (2H, m), 7.80–7.70 (2H, m), 7.62 (2H, d), 7.49–7.25 (5H, m), 7.10–6.95 (5H, m), 6.48 (1H, d), 6.40 (1H, t), 5.10 (2H, s), 4.38 (2H, d); m/z 500 (M+1)$^+$.

Example 15

(4-Benzyloxy-phenyl)-(6-(5-(((tetrahydro-furan-2-ylmethyl)-amino)-methyl)-furan-2-yl)-quinazolin-4-yl)-amine hydrochloride 5-(4-(4-Benzyloxy-phenylamino)-quinazolin-6-yl)-furan-2-carbaldehyde and tetrahydro-furfuralamine were reacted in an analogous manner to Example 10 to give the title compound; δH [$^2$H$_6$]-DMSO (of the free base) 9.82 (1H, s), 8.69 (1H, s), 8.41 (1H, s), 8.10 (1H, d), 7.71(1H, d), 7.62 (2H, d), 7.50–7.25 (5H, m), 7.10–7.06 (3H, m), 6.42 (1H, d), 5.10 (2H, s), 3.91–3.50 (9H, m), 2.60 (2H, d); m/z 507 (M+1)$^+$.

Example 16

(1-Benzyl-1H-indazol-5-yl)-(6-(5-(1,3)-dioxolan-2-yl-furan-2-yl)-quinazolin-4-yl)-amine (1-Benzyl-1H-indazol-5-yl)-(6-bromoquinazolin-4-yl)-amine (4.3 g), 2-(tributylstannyl)-5-(1,3-dioxolan-2-yl)-furan (J. Chem. Soc., Chem Commun., (1988), 560) (10 g) and 1,4-bis(diphenylphosphino) palladium (II) chloride (1 g) were heated at reflux in dioxane (150 ml) for 24 hr. The solvent was removed in vacuo and the residue chromatographed on silica. Subsequent trituration gave the title compound δH [$^2$H$_6$]-DMSO 10.13 (1H, s), 8.85 (1H, s), 8.54 (1H, s), 8.20 (3H, m), 7.80 (3H, m), 7.30 (5H, m), 7.13 (1H, d), 6.79 (1H, d), 6.04 (1H, s), 5.71 (2H, s), 4.15 (4H, m).

Example 17

5-(4-(1-Benzyl-1H-indazol-5-ylamino)-quinazolin-6-yl)-furan-2-carbaldehyde hydrochloride (1-Benzyl-1H-indazol-5-yl)-(6-(5-(1,3)-dioxolan-2-yl-furan-2-yl)-quinazolin-4-yl)-amine (2.0 g) and hydrochloric acid (2N, 50 ml) were stirred in THF (20 ml) for 16 hr. The resulting precipitate was filtered, washed with water and dried at 60° C. in vacuo to give the product as a yellow solid (1.80 g, 3.73 g, 91%); δH [$^2$H$_6$]-DMSO 12.30 (1H, s), 9.79 (1H, s), 9.62 (1H, s), 8.85 (1H, s), 8.62 (1H, m), 8.31 (1H, s), 8.19 (1H, m), 8.10 (1H, d), 7.90 (2H, m), 7.78 (2H, m), 7.40 (5H, m), 5.80 (2H, s).

Example 18

(S)-1-(5-(4-(1-Benzyl-1H-indazol-5-ylamino)-quinazolin-6-yl)-furan-2-ylmethyl)-pyrrolidine-2-carboxylic acid amide dihydrochloride 5-(4-(1-Benzyl-1H-indazol-5-ylamino)-quinazolin-6-yl)-furan-2-carbaldehyde and L-prolinamide were reacted in an analogous manner to Example 10. Purification by silica gel chromatography, eluting with 4–7%MeOH/CHCl$_3$, followed by acidification with ethereal HCl gave the product as a yellow solid (0.075 g, 0.122 mmol, 29%); δH [$^2$H$_6$]-DMSO 12.80 (1H, s), 9.79 (1H, s), 8.85 (1H, s), 8.45 (1H, d), 8.38 (1H, s), 8.22 (1H, s), 8.14 (1H, s), 8.06 (1H, d), 7.82 (1H, d), 7.75 (1H, dd), 7.70 (1H, s), 7.50 (1H, d), 7.30 (5H, m), 6.90 (1H, d), 5.72 (2H, s), 4.64 (1H, m), 4.59 (2H, s), 3.50 (2H, m), 1.90 (4H, m); m/z 544 (M +1)$^+$.

Example 19

(1-Benzyl-1H-indazol-5-yl)-(6-(5-((2-methanesulphonyl-ethylamino)-methyl)-furan-2-yl)-quinazolin-4-yl)-amine dihydrochloride 5-(4-(1-Benzyl-1H-indazol-5-ylamino)-quinazolin-6-yl)-furan-2-carbaldehyde and 2-methylsulphonylamine were reacted in an analogous manner to Example 10 to give the title compound; δH [$^2$H$_6$]-DMSO 12.15 (1H, s), 10.00 (1H, bs), 9.75 (1H, s), 8.88 (1H, s), 8.45 (1H, d), 8.24 (1H, s), 8.16 (1H, s), 8.00 (1H, d), 7.84 (1H, d), 7.77 (1H, dd), 7.39 (1H, d), 7.30 (5H, m), 6.87 (1H, d), 5.72 (2H, s), 4.46 (2H, s), 3.70 (4H, m), 3.15 (3H, s); m/z (M +1)$^+$ 553.

Example 20

(4-Phenoxy-phenyl)-(6-(5-methyl-1,3,4-oxadiazol-2-yl)quinazolin-4-yl)-amine hydrochloride 4-Chloro-6-(5-methyl-1,3,4-oxadiazol-2-yl)quinazoline was treated with 4-phenoxyaniline according to Procedure A to give the title compound as a yellow solid; δH [$^2$H$_6$]DMSO 11.78 (1H, bs), 9.45(1H, s), 8.95 (1H, s), 8.60(1H, dd), 8.10 (1H, d), 7.75 (2H, d) 7.45(2H, d), 7.10(5H, m), 2.68(3H, s); m/z (M+1$^+$) 396.

Example 21

(1-(2-Fluorobenzyl)-1H-indazol-5-yl)-(6-(5-methyl-1,3,4-oxadiazol-2-yl)-quinazolin-4-yl-amine hydrochloride The title compound was prepared according to Procedure A from 1-(2-fluorobenzyl)-1H-indazol-5-ylamine and 4-chloro-6-(5-methyl-1,3,4-oxadiazol-2-yl)-quinazoline; δH [$^2$H$_6$]DMSO 11.70(1H, s), 9.45(1H, s), 8.90(1H, s), 8.60(1H, d), 8.20(1H, s), 8.13(1H, s), 7.85(1H, d), 7.70(1H, d), 7.38(1H, m), 7.24 (1H, m), 7.17 (3H, m), 5.76(2H, s), 2.65 (3H, s); m/z (M+1$^+$) 452.

Example 22
(1-(3-Fluorobenzyl)-1H-indazol-5-yl)-(6-(5-methyl-1,3,4-oxadiazol-2-yl)-quinazolin-4-yl)-amine hydrochloride The title compound was prepared according to Procedure A from 1-(3-fluorobenzyl)-1H-indazol-5-ylamine and 4-chloro-6-(5-methyl-1,3,4-oxadiazol-2-yl)-quinazoline; δH [$^2$H$_6$]DMSO 11.80(1H, s), 9.45(1H, s), 8.90(1H, s), 8.60(1H, d), 8.25(1H, s), 8.13(2H, m), 7.87(1H, d), 7.79(1H, d), 7.39(1H, dd), 7.10(3H, m), 5.75(2H, s), 2.65 (3H, s); m/z (M+1$^+$) 452.

Example 23
(1-Pyridin-2-ylmethyl)-1H-indazol-5-yl)-(6-(5-methyl-1,3,4-oxadiazol-2-yl)-quinazolin-4-yl)-amine hydrochloride The title compound was prepared according to Procedure A from (1-pyridin-2-ylmethyl)-1H-indazol-5-ylamine and 4-chloro-6-(5-methyl-1,3,4-oxadiazol-2-yl)-quinazoline; δH [$^2$H$_6$]DMSO 11.70(1H, s), 9.46(1H, s), 8.90(1H, s), 8.55(2H, m), 8.24(1H, s), 8.11(2H, m), 7.80(2H, m), 7.69 (1H, dd), 7.33(1H, m), 7.10(1H, d), 5.83(2H, s), 2.66 (3H, s); m/z (M+1$^+$) 435.

Example 24
(1-(2,3-Difluorobenzyl)-1H-indazol-5-yl)-(6-(5-methyl-1,3,4-oxadiazol-2-yl)quinazolin-4-yl)-amine hydrochloride The title compound was prepared according to Procedure A from 1-(2,3-difluorobenzyl)-1H-indazol-5-ylamine and 4-chloro-6-(5-methyl-1,3,4-oxadiazol-2-yl)-quinazoline; δH [$^2$H$_6$]DMSO 11.90(1H, s), 9.47(1H, s), 8.91(1H, s), 8.60(1H, d), 8.25(1H, s), 8.15(2H, m), 7.89(1H, d), 7.72(1H, dd), 7.40(1H, m), 7.18(1H, m), 6.98(1H, m), 5.83(2H, s), 2.67(3H, s); m/z (M+1$^+$) 470.

Example 25
(3-Chloro-4-(2-fluoro-benzyloxy)-phenyl)-(6-(5-methyl-1,3,4-oxadiazol-2-yl)-s-quinazolin-4-yl)-amine hydrochloride The title compound was prepared according to Procedure A from 3-chloro-4-(2-fluoro-benzyloxy)aniline and 4-chloro-6-(5-methyl-1,3,4-oxadiazol-2-yl)-quinazoline; δH [$^2$H$_6$]DMSO 11.64(1H, bs), 9.40(1H, s), 8.97(1H, s), 8.58(1H, d), 8.11(1H, d), 7.94(1H, d), 7.71(1H, dd), 7.63 (1H, dd), 7.45(2H, m), 7.30(2H, m), 5.31 (2H, s), 2.68(3H, s); m/z (M+1$^+$) 462.

Example 26
(3-Chloro-4-(3-fluoro-benzyloxy)-phenyl)-(6-(5-methyl-1,3,4-oxadiazol-2-yl)-quinazolin-4-yl)-amine hydrochloride The title compound was prepared according to Procedure A from 3-chloro-4-(3-fluoro-benzyloxy)aniline and 4-chloro-6-(5-methyl-1,3,4-oxadiazol-2-yl)-quinazoline; δH [$^2$H$_6$]DMSO 11.73(1H, bs), 9.38(1H, s), 8.94(1H, s), 8.57(1H, d), 8.10(1H, d), 7.90(1H, d), 7.65(1H, dd), 7.45 (1H, m), 7.30(3H, m), 7.16(1H, m), 5.30(2H, s), 2.65(3H, s); m/z (M+1$^+$) 462.

Example 27
(4-Benzyloxy-phenyl)-(6-(5-methyl-1,3,4-oxadiazol-2-yl)-quinazolin-4-yl)-amine hydrochloride The title compound was prepared according to Procedure A from 4-benzyloxyaniline and 4-chloro-6-(5-methyl-1,3,4-oxadiazol-2-yl)-quinazoline; δH [$^2$H$_6$]DMSO 11.73(1H, bs), 9.41(1H, s), 8.90(1H, s), 8.58(1H, d), 8.10(1H, d), 7.65(2H, d), 7.40(5H, m), 7.15(2H, d), 5.19(2H, s), 2.65(3H, s); m/z (M+1$^+$) 410.

Example 28
(4-(2-Fluoro-benzyloxy)-phenyl)-(6-(5-methyl-1,3,4-oxadiazol-2-yl)-quinazolin-4-yl)-amine hydrochloride The title compound was prepared according to Procedure A from 4-(2-fluoro-benzyloxy)aniline and 4-chloro-6-(5-methyl-1,3,4-oxadiazol-2-yl)-quinazoline; δH [$^2$H$_6$]DMSO 11.72(1H, bs), 9.41(1H, s), 8.91(1H, s), 8.59(1H, d), 8.10 (1H, d), 7.65(3H, m), 7.45(1H, m), 7.25(2H, m), 7.18(2H, d), 5.20(2H, s), 2.65(3H, s); m/z (M+1$^+$) 428.

Example 29
(4-(3-Fluoro-benzyloxy)-phenyl)-(6-(5-methyl-1,3,4-oxadiazol-2-yl)-quinazolinyl)-amine hydrochloride The title compound was prepared according to Procedure A from 4-(3-fluoro-benzyloxy)aniline and 4-chloro-6-(5-methyl-1,3,4-oxadiazol-2-yl)-quinazoline; δH [$^2$H$_6$]DMSO 11.71(1H, bs), 9.40(1H, s), 8.90(1H, s), 8.58(1H, d), 8.09 (1H, d), 7.66(2H, d), 7.47(1H, m), 7.33(2H, m), 7.15(3H, m), 5.21(2H, s), 2.65(3H, s); m/z (M+1$^+$) 428.

Example 30
(4-Benzenesulphonyl-phenyl)-(6-(5-methyl-1,3,4-oxadiazol-2-yl)-quinazolin-4-yl)-amine hydrochloride The title compound was prepared according to Procedure A from 4-benzenesulphonylaniline and 4-chloro-6-(5-methyl-1,3,4-oxadiazol-2-yl)-quinazoline; δH [$^2$H$_6$]DMSO 11.63(1H, bs), 9.42(1H, s), 8.95(1H, s), 8.56(1H, d), 8.10 (6H, m), 7.70(4H, m), 2.65(3H, s); m/z (M+1$^+$) 444.

Example 31
(1-(3,5-Difluoro-benzyl)-1H-indazol-5-yl)-(6-(5-methyl-1,3,4-oxadiazol-2-yl)-quinazolin-4-yl)-amine hydrochloride The title compound was prepared according to Procedure A from 1-(3,5-difluoro-benzyl)-1H-indazol-5-ylamine and 4-chloro-6-(5-methyl-1,3,4-oxadiazol-2-yl)-quinazoline; δH [$^2$H$_6$]DMSO 12.50(1H, bs), 10.35(1H, s), 9.25(1H, s), 8.61(1H, s), 8.35(1H, m), 8.22(2H, m), 7.88(1H, dd), 7.75 (2H, m), 7.16(1H, m), 6.93(1H, m), 5.73(2H, s), 2.67(3H, s); m/z (M+1$^+$) 470.

Example 32
(4-(4-Fluoro-benzyloxy)-phenyl)-(6-(5-methyl-1,3,4-oxadiazol-2-yl)-quinazolin-4-yl)-amine hydrochloride The title compound was prepared according to Procedure A from 4-(4-fluoro-benzyloxy)aniline and 4-chloro-6-(5-methyl-1,3,4-oxadiazol-2-yl)-quinazoline; δH [$^2$H$_6$]DMSO 11.68(1H, bs), 9.39(1H, s), 8.89(1H, s), 8.56(1H, d), 8.07 (1H, d), 7.64(2H, d), 7.54(2H, m), 7.24(2H, dd), 7.14(2H, d), 5.14(2H, s), 2.65(3H, s); m/z (M+1$^+$) 428.

Example 33
(4-(2-Fluoro-benzyloxy)-phenyl)-(6-(5-trifluoromethyl-1,3,4-oxadiazol-2-yl)-quinazolin-4-yl)-amine hydrochloride The title compound was prepared according to Procedure A from 4-(2-fluoro-benzyloxy)aniline and 4-chloro-6-(5-trifluoromethyl-1,3,4-oxadiazol-2-yl)-quinazoline; δH [$^2$H$_6$] DMSO 11.80(1H, bs), 9.54(1H, s), 8.93(1H, s), 8.67(1H, dd), 8.14(1H, d), 7.67(2H, d), 7.59(1H, m), 7.46(1H, m), 7.29(2H, m), 7.19(2H, d), 5.23(2H, s); m/z (M+1$^+$) 482.

Example 34
(4-(3-Fluorobenzyloxy)-phenyl)-(6-(5-trifluoromethyl-1,3,4-oxadiazol-2-yl)-quinazolin-4-yl)-aminehydrochloride The title compound was prepared according to Procedure A from 4-(3-fluoro-benzyloxy)aniline and 4-chloro-6-(5-trifluoromethyl-1,3,4-oxadiazol-2-yl)-quinazoline; δH [$^2$H$_6$] DMSO 11.74(1H, bs), 9.51(1H, s), 8.91(1H, s), 8.66(1H, dd), 8.12(1H, d), 7.65(2H, d), 7.48(1H, m), 7.32(2H, m), 7.19(1H, m), 7.17(2H, d), 5.20(2H, s); m/z (M+1$^+$) 482.

Example 35
(4-(4-Fluoro-benzyloxy)-phenyl)-(6-(5-trifluoromethyl-1,3,4-oxadiazol-2-yl)-quinazolin-4-yl-aminehydrochloride The title compound was prepared according to Procedure A from 4-(4-fluoro-benzyloxy)aniline and 4-chloro-6-(5- trifluoromethyl-1,3,4-oxadiazol-2-yl)-quinazoline; δH [$^2$H$_6$] DMSO 11.81(1H, bs), 9.53(1H, s), 8.91(1H, s), 8.67(1H, dd), 8.13(1H, d), 7.63(2H, d), 7.54(2H, dd), 7.25(2H, dd), 7.15(2H, d), 5.15(2H, s); m/z (M+1$^+$) 482.

Example 36
(1-Benzyl-1H-indazol-5-yl)-(6-(5-trifluoromethyl-1,3,4-oxadiazol-2-yl)-quinazolin-4-yl)-amine hydrochloride The title compound was prepared according to Procedure A from 1-benzyl-1H-indazol-5-ylamine and 4-chloro-6-(5-trifluoromethyl-1,3,4-oxadiazol-2-yl)-quinazoline; δ[$^2$H$_6$] DMSO 11.96(1H, bs), 9.58(1H, s), 8.91(1H, s), 8.69(1H, dd), 8.22(1H, s), 8.14(1H, d), 8.10(1H, d), 8.85(1H, d), 8.67(1H, dd), 7.30(5H, m), 5.71(2H, s); m/z (M+1$^+$) 488.

Example 37
(4-Pyridin-3-ylmethoxy)-phenyl)-(6-(5-trifluoromethyl-1,3,4-oxadiazol-2-yl)-quinazolin-4-yl)-amine hydrochloride The title compound was prepared according to Procedure A from (4-pyridin-3-ylmethoxy)aniline and 4-chloro-6-(5-trifluoromethyl-1,3,4-oxadiazol-2-yl)-quinazoline; δH [$^2$H$_6$] DMSO 11.44(1H, bs), 9.50(1H, s), 8.85(2H, m), 8.70(1H, d), 8.62(1H, d), 8.16(1H, d), 8.10(1H, d), 7.69(2H, d), 7.65(1H, m), 7.18(2H, d), 5.29(2H, s); m/z (M+1$^+$) 465.

Example 38
(1-Benzyl-1H-indazol-5-yl)-(6-(3-methyl-3H-imidazol-4-yl)-quinazolin-4-yl)-amine Prepared in an analogous manner to Example 6 according to Procedure B from (1-Benzyl-1H-indazol-5-yl)-(6-iodoquinazolin-4-yl)-amine and 5-(tributylstannyl)-1-methylimidazole; δH [$^2$H$_6$]DMSO 9.98(1H, s), 8.62(1H, s), 8.55(1H, s), 8.20(1H, s), 8.15(1H, s), 7.99(1H, dd), 7.83(2H, m), 7.70(2H, m), 7.28(6H, m), 5.70(2H, s), 3.70(3H, s); m/z (M+1)$^+$ 432.

Example 39
(1-Benzyl-1H-indazol-5-yl)-(6-(1-methyl-1H-imidazol-2-yl)quinazolin-4-yl)-amine Prepared in an analogous manner to Example 6 according to Procedure B from (1-Benzyl-1H-indazol-5-yl)-(6-iodoquinazolinyl)-amine and 2-(tributylstannyl)-1-methylimidazole (prepared according to the published method: J. Organometallic Chem., (1989), 61); δH [$^2$H$_6$] DMSO 10.09(1H, s), 8.80(1H, s), 8.57(1H, s), 8.20(1H, s), 8.15(2H, m), 7.85(1H, d), 7.70(2H, m), 7.30(6H, m), 7.09 (1H, s), 5.70(2H, s), 3.88(3H, s); m/z (M+1)$^+$ 432.

Example 40
(4-Benzyloxy-phenyl)-(6-(1H-tetrazol-5-yl)-quinazolin-4-yl)-amine (4-Benzyloxy-phenyl)-(6-cyanoquinazolin-4-yl)-amine (0.106 g) in dimethylformamide was treated with sodium azide (0.06 g) and ammonium chloride (0.05 g) and the mixture stirred at 180° C. for 18 hours. The mixture was cooled, poured onto water and extracted with ethyl acetate/THF (3:1). The organic extracts were dried and concentrated in vacuo. The residue was purified using solid phase extraction to yield the title compound (0.024 g); δ H [$^2$H$_6$]DMSO 10.18(1H, s), 9.25(1H, s), 8.55(1H, s), 8.40(1H, d), 7.88(1H, d), 7.74(2H, d), 7.45(6H, m), 7.07(2H, d), 5.17(1H, s); m/z (M+1)$^+$ 396.

Example 41
(1-Benzyl-1H-indazol-5-yl)-(6-(5-methyl-1,3,4-oxadiazol-2-yl)-quinazolin-4-yl)-amine hydrochloride (1-Benzyl-1H-indazol-5-yl)-(6-hydrazidoquinazolin-4-yl)-amine (0.155 g) was treated with triethylorthoacetate (8 ml) at reflux for 18 hours. Concentration in vacuo and chromatography on silica was followed by precipitation from methanolic HCl to give the title compound as a yellow solid; δH [$^2$H$_6$]DMSO 11.93(1H, s), 9.50(1H, s), 8.97(1H, s), 8.67(1H, d), 8.30(1H, s), 8.16(2H, m), 7.91 (1H, d), 7.74(1H, dd), 7.38(5H, m), 5.80(2H, s), 2.74(3H, s); m/z (M+1)$^+$ 434.

Example 42
(1-Benzyl-1H-indazol-5-yl)-(6-(5-methyl-1,3,4-triazol-2-yl)-quinazolin-4-yl)-amine (1-Benzyl-1H-indazol-5-yl)-(6-hydrazido-quinazolin-4-yl)-amine (0.102 g) in methanol (5 ml) under N$_2$ was treated with ethyl imidate hydrochloride (0.03 g) and triethylamine (0.05 g) at reflux for 18 hours. The resulting mixture was absorbed onto silica and chromatographed to give the title compound (0.018 g); δH [$^2$H$_6$]DMSO 10.25(1H, s), 9.20 (1H, s), 8.55(1H, s), 8.45(1H, d), 8.22(1H, s), 8.12(2H, s), 7.82(1H, d), 7.73(2H, s), 7.30(5H, m), 5.70(2H, s), 2.50(3H, s); m/z (M+1)$^+$ 433.

Example 43
(S)-1-(2-(4-(4-Benzyloxy-phenylamino)-quinazolin-6-yl)-3-methyl-3H-imidazol-4-ylmethyl)-pyrrolidine-2-carboxylic acid amide 2-(4-(4-Benzyloxy-phenylamino)-quinazolin-6-yl)-3-methyl-3H-imidazole-4-carbaldehyde was dissolved in dichloromethane (5 ml) containing glacial acetic acid (0.03 ml). L-prolinamide (0.028 g) was added and the mixture stirred at 20° C. for 0.75 hours. Sodium acetoxyborohydride (0.08 g) was added and the reaction stirred at 20° C. for 18 hours. The mixture was partitioned between 2N sodium carbonate and ethyl acetate, the organic phase was dried over magnesium sulphate and concentrated in vacuo. Chromatography on silica gave the title compound (0.008 g) as a yellow solid; tlc (SiO$_2$, CH$_2$Cl$_2$:EtOH:NH$_3$, 100:8:1) Rf 0.18; m/z (M+1)$^+$ 534.

Example 44
(1-Benzyl-1H-indazol-5-yl)-(6-(5-methanesulphonylmethyl-1,3,4-oxadiazol-2-yl)-quinazolin-4-yl)-amine (1-Benzyl-1H-indazol-5-yl)-(6-(methanesulphonylethanoyl-hydrazido)-quinazolin-4-yl)-amine (0.06 g) was treated with phosphorus oxychloride (0.02 ml) in dry acetonitrile (10 ml) at reflux under N$_2$ for 18 hours. Further portions of the chloride were added (2×0.1 ml and 1×0.2 ml) over a period of 8 days. Cooling, concentration in vacuo and chromatography on silica gave the desired compound after precipitation from methanolic HCl; LC R.T. 3.97 mins., m/z (M+1)$^+$ 434.

Example 45
(4-Benzyloxy-phenyl)-(6-(1-methylpyridinium-2-yl)quinazolin-4-yl)-amine chloride hydrochloride Methyl iodide (20 drops) was added to a solution of (4-benzyloxy-phenyl)-(6-(pyridin-2-yl)-quinazolin-4-yl)-amine (0.10 g, 0.247 mmol) and the mixture was stirred at room temperature for 24 hours. As tlc indicated incomplete reaction, further methyl iodide (1.0 ml) was added and stirring was continued for 4 days, by which time tlc showed complete reaction. The yellow precipitate was collected by filtration and washed with acetone. It was treated with 2N aqueous HCl, and the deeper yellow solid was collected by filtration and again washed with acetone to give the product (0.090 g, 0.183 mmol, 74%); δH [$^2$H$_6$]DMSO 12.1 (1H, s), 9.62 (1H, s), 8.98 (1H, s), 8.93 (1H, dd), 8.81 (1H, d), 8.43 (1H, d), 8.19 (1H, d), 8.08 (1H, td), 7.64 (2H, d), 7.33–7.58 (6H, m), 7.18 (2H, d), 5.18 (2H, s), 4.09 (3H, s); m/z (M+1$^+$) 419.

Example 46
(4-Benzyloxy-phenyl)-(6-(2,3-dimethyl-3H-imidazol-4-yl)-quinazolin-4-yl)-amine hydrochloride.

The (4-benzyloxy-phenyl)-(6-iodoquinazolin-4-yl)-amine (0.30 g, 0.61 mmol), 1,2-dimethyl-5-(tributylstannyl) imidazole (Iddon, B. and Lim, B. L., *J. Chem., Soc., Perkin Trans.* 1(1983), (2), 271–7) (0.46 g, 1.19 mmol) and bis(triphenylphosphine)palladium (II) chloride (0.05 g, 0.07 mmol) were reacted in dioxane (10 ml) according to Procedure B for 18 hours. Purification by silica gel chromatography (eluting with 10%MeOH/EtOAc), followed by acidification with methanolic HCl and trituration with ether gave the product (0.163 g, 0.36 mmol, 58%); δH [$^2$H$_6$]DMSO 12.4 (1H, s), 9.52 (1H, s), 8.91 (1H, s), 8.22 (1H, d), 8.15 (1H, d), 8.03 (1H, s), 7.70 (2H, d), 7.30–7.60 (5H, m), 7.13 (2H, d), 5.17 (2H, s), 3.73 (3H, s), 2.57 (3H, s); m/z (M+1$^+$) 422.

Example 47
(4-Benzyloxy-phenyl)-(-6-(3-methylisoxazol-5-yl)-quinazolin-4-yl)-amine hydrochloride A stirred mixture of (4-benzyloxy-phenyl)-(6-ethynylquinazolin-4-yl)-amine (0.20 g, 0.57 mmol), nitroethane (0.20 g, 2.7 mmol), phenylisocyanate (0.15 ml, 0.164 g, 1.38 mmol), and triethylamine (3 drops) in a mixture of ethyl acetate (10 ml) and dichloromethane (5 ml) was heated at reflux for 18 hours. After cooling the mixture was filtered to remove solid, and the concentrated filtrate was purified by silica gel chromatography, eluting with 50% ethyl acetate/i-hexane. After concentration of the appropriate fractions, the material obtained was treated with methanolic HCl, the solvent was removed in vacuo and the residue was triturated with ether to give the title compound as a yellow solid (0.027 g, 0.061 mmol, 11%); δH [$^2$H$_6$]DMSO 12.0 (1H, s), 9.55 (1H, s), 8.91 (1H, s), 8.48 (1H, d), 8.03 (1H, d), 7.68 (2H, d), 7.32–7.55 (5H, m), 7.22 (1H, s), 7.15 (2H, d), 5.18 (2H, s), 2.35 (3H, s); m/z (M+1$^+$) 409.

Example 48
(4-Benzyloxy-phenyl)-(6-(5-(((2-methanesulphonyl-ethyl)-methyl-amino)-methyl)-furan-2-yl)-quinazolin-4-yl)-amine In an analogous manner to Example 10, 5-(4-(4-Benzyloxy-phenylamino)-quinazolin-6-yl)-furan-2-carbaldehyde hydrochloride (0.217 g, 0.474 mmol) was reacted with N-methyl-N-(2-methanesulphonyl-ethyl)amine (0.411 g, 3.0 mmol). Purification by silica gel chromatography, eluting with 2–3% MeOH/CHCl$_3$, followed by trituration with ether, gave the title compound as a pale yellow solid (0.100 g, 0.184 mmol, 39%); δH [$^2$H$_6$]DMSO 9.84 (1H, s), 8.63 (1H, s), 8.48 (1H, s), 8.12 (1H, d), 7.78 (1H, d), 7.68 (2H, d), 7.13–7.52 (5H, m), 7.02–7.10 (3H, m), 6.55 (1H, d), 5.14 (2H, s), 3.70 (2H, s), 3.35–3.44 (2H, obscured by water), 3.05 (3H, s), 2.84 (2H, t), 2.28 (3H, s).

Example 49
N-(2-((5-(4-(4-Benzyloxy-phenylamino)-quinazolin-6-yl)-furan-2-ylmethyl)-amino) -ethyl)-methanesulphonamide dihydrochloride In an analogous manner to Example 10, 5-(4-(4-Benzyloxy-phenylamino)-quinazolin-6-yl)-furan-2-carbaldehyde hydrochloride (0.200 g, 0.436 mmol) was reacted with 2-(methanesulphonamido)ethylamine (0.350 g, 2.53 mmol). On completion of the reaction the mixture was acidified with dilute HCl and diluted with water, but no solid was formed. The mixture was concentrated in vacuo, and the residue was washed with acetone, 2N HCl and acetone again, and dried at 60° C. in vacuo to give the title compound as a yellow solid (0.210 g, 0.340 mmol, 78%); δH [$^2$H$_6$]DMSO 12.01 (1H, s), 9.82 (1H, br s), 9.77 (1H, s), 8.88 (1H, s), 8.40 (1H, d), 8.02 (1H, d), 7.76 (2H, d), 7.31–7.53 (6H, m), 7.14 (2H, d), 6.84 (1H, d), 5.18 (2H, s), 4.40 (2H, s), 3.34–3.48 (2H, m), 3.08–3.18 (2H, m), 2.96 (3H, s); m/z (M+1$^+$) 544.

Example 50
2-((5-(4-(4-Benzyloxy-phenylamino)-quinazolin-6-yl)-furan-2-ylmethyl)-amino)-ethanesulphonic acid amide In an analogous manner to Example 10, 5-(4-(4-Benzyloxy-phenylamino)-quinazolin-6-yl)-furan-2-carbaldehyde hydrochloride (0.200 g, 0.436 mmol) was reacted with 2-aminoethylsulphonamide hydrochloride (0.200 g, 1.245 mmol) and triethylamine (10 drops). On completion of the reaction, the mixture was acidified with dilute HCl and diluted with water, to give the crude product as a precipitate collected by filtration. Treatment with triethylamine followed by purification by silica gel chromatography, eluting with 3–10% MeOH/CHCl$_3$ gave the title compound as a yellow solid (0.085 g, 0.160 mmol, 37%); δH [$^2$H$_6$]DMSO 9.61 (2H, brs), 9.25 (1H, s), 8.58 (1H, s), 8.23 (1H, d), 7.77–7.88 (3H, m), 7.30–7.52 (5H, m), 7.26 (2H, s), 7.20 (1H, d), 7.08 (2H, d), 6.81 (1H, d), 5.14 (2H, s), 4.44 (2H, s), 3.34–3.60 (2H, m), 3.25–3.45 (2H, obscured by water); m/z (M+1$^+$) 530.

Example 51
5-(4-(4-Benzyloxy-phenylamino)-quinazolin-6-yl)-furan-2-carboxylic acid methyl ester (4-Benzyloxy-phenyl)-(6-(5-(4-methyl-2,6,7-trioxabicyclo[2.2.2]oct-1-yl)-furan-2-yl)-quinazolin-4-yl)-amine (0.680 g, 1.30 mmol) was dissolved in THF (10 ml) and 2N aqueous HCl (10 ml) was added. The mixture was stirred at room temperature for 2 hours. The THF was removed in vacuo and the residue diluted with water to preciptate the intermediate (partial hydrolysis) 5-(4-(4-benzyloxy-phenylamino)-quinazolin-6-yl)-furan-2-carboxylic acid (3-methyloxetan-3-yl)-methyl ester which was collected by filtration and washed with water and acetone; δH [$^2$H$_6$]DMSO 12.10 (1H, s), 9.50 (1H, s), 8.87 (1H, s), 8.43 (1H, s), 8.00 (1H, s), 7.66 (2H, d), 7.58 (1H, d), 7.30–7.54 (6H, m), 7.13 (2H, d), 5.16 (2H, s), 4.14 (2H, s), 3.28–3.41 (4H, m), 0.88 (3H, s). This solid was suspended in a mixture of MeOH (15 ml) and NaOH (2N, 15 ml), and the mixture was stirred at room temperature for 2 hours. The reaction was diluted with water to give the title product as a yellow solid, which was collected by filtration (0.375 g, 0.831 mmol, 64%); δH [$^2$H$_6$]DMSO 10.06 (1H, s), 8.91 (1H, s), 8.48 (1H, s), 8.21 (1H, d), 7.80 (1H, d), 7.63 (2H, d), 7.25–7.52 (7H, m), 7.05 (2H, d), 5.10 (2H, s), 3.85 (3H, s); m/z (M+1$^+$) 452.

Example 52
5-(4-(4-Benzyloxy-phenylamino)-quinazolin-6-yl)-furan-2-carboxylic acid hydrochloride 5-(4-(4-Benzyloxy-phenylamino)-quinazolin-6-yl)-furan-2-carboxylic acid methyl ester (0.150 g, 0.332 mmol) was suspended in a mixture of EtOH (2 ml) and 2N aqueous NaOH (2 ml). The mixture was stirred at room temperature for 15 mins. To facilitate dissolution, CHCl$_3$ (2 ml) was added and stirring was continued for 3 days, by which time tlc showed there to be no remaining starting material. The organic solvents were removed in vacuo and the residue diluted with water and treated with 2N aqueous HCl to give the product as a yellow solid, which was collected by filtration (0.130 g, 0.274 mmol, 83%); m/z (M+1$^+$) 438.

Example 53
5-[4-(4-Benzyloxy-phenylamino)-quinazolin-6-yl]-furan-2-carboxylic acid (2-methanesulphonyl-ethyl)-amide hydrochloride 5-(4-(4-Benzyloxy-phenylamino)-quinazolin-6-yl)-furan-2-carboxylic acid hydrochloride (0.130 g, 0.274 mmol) and carbonyldiimidazole (0.053 g, 0.326 mmol) were mixed in THF (2 ml) and stirred at room temperature under a nitrogen atmosphere for 2.5 hours. 2-(Methylsulphonyl)ethylamine hydrochloride (0.055 g, 0.45 mmol) and triethylamine (5 drops) were added, and the resulting mixture was stirred at room temperature for 3 days. The mixture was diluted with water, and treated with conc. HCl until at pH 1, to give the crude product as a yellow solid, which was further purified by silica gel chromatography, eluting with 5–10% MeOH/CHCl$_3$. Concentration of the relevant fractions, followed by treatment with 2N aqueous HCl gave the product as an yellow solid, which was collected by filtration and washed with acetone and ether (0.028 g, 0.048 mmol, 18%); δH [$^2$H$_6$]DMSO 12.05 (1H, s), 9.66 (1H, s), 9.21 (1H, t), 8.88 (1H, s), 8.55 (1H, d), 7.91 (1H, d), 7.71 (2H, d), 7.28–7.54 (7H, m), 7.15 (2H, d), 5.18 (2H, s), 3.72 (2H, dd), 3.40–3.52 (2H obscured by water signal), 3.07 (3H, s); m/z (M+1$^+$) 543.

Example 54

2-((5-(4-(4-Benzyloxy-phenylamino)-quinazolin-6-yl)-furan-2-ylmethyl)-amino)-ethanesulphonic acid methylamide In an analogous manner to Example 10, 5-(4-(4-Benzyloxy-phenylamino)-quinazolin-6-yl)-furan-2-carbaldehyde hydrochloride (0.200 g, 0.436 mmol) was reacted with 2-(methylsulphonamido)ethylamine (Int. J. Pept. Protein Res., (1984), 24(4), 367–76) (0.200 g, 1.145 mmol) and triethylamine (10 drops). On completion of the reaction the mixture was diluted with water and acidified with dilute HCl and the resulting solid collected. Treatment with triethylamine followed by purification by silica gel chromatography, eluting with 4–6% MeOH/CHCl$_3$, gave the title compound as a yellow solid (0.080 g, 0.147 mmol, 34%); δH [$^2$H$_6$]DMSO 9.85 (1H, s), 8.74 (1H, s), 8.48 (1H, s), 8.14 (1H, d), 7.75 (1H, d), 7.65 (2H, d), 7.33–7.54 (5H, m), 7.02–7.12 (3H, m), 6.91 (1H, br), 6.49 (1H, d), 5.14 (2H, s), 3.84 (2H, s), 3.20 (2H, t), 2.88–2.98 (2H, m), 2.53–2.60 (3H, m, obscured by DMSO); m/z (M+1$^+$) 544.

Example 55

(1-Benzyl-1H-indazol-5-yl)-(6-(3-methyl-1,2,4-oxadiazol-5-yl)-quinazolin-4-yl)-amine hydrochloride (4-(1-Benzyl-1H-indazol-5-yl)-quinazolin-6-yl)-carboxylic acid (0.150 g, 0.379 mmol) was stirred with 1,1'-carbonyldiimidazole (0.123 g, 0.759 mmol) in dry THF at room temperature for 3 hours. Acetamidoxime (0.084 g, 1.13 mmol) was added and the mixture was stirred at room temperature overnight. The mixture was partitioned between water and ethyl acetate, and the organic extracts were dried and concentrated. Purification by silica gel chromatography, eluting with 100:8:1 dichloromethane:EtOH:NH$_3$, gave a pale yellow gum. Treatment with methanolic HCl, followed by concentration in vacuo gave the product as a bright yellow solid (0.038 g, 0.081 mmol, 21%); δH [$^2$H$_6$]DMSO 9.62 (1H, s), 8.95 (1H, s), 8.69 (1H, d), 8.23 (1H, d), 8.08–8.15 (2H, m), 7.85 (1H, d), 7.67 (1H, dd), 7.23–7.39 (5H, m), 5.72 (2H, s), 3.40–3.60 (3H, s, obscured by water); m/z (M+1$^+$) 434.

Example 56

(4-Benzyloxy-phenyl)-(6-(5-methyl-1,2,4-oxadiazol-3-yl)-quinazolin-4-yl)-amine (4-(4-Benzyloxyanilino)quinazolin-6-yl)-(N-hydroxycarboximidamide) (0.077 g, 0.20 mmol) and ethyl acetate (0.02 ml, 0.018 g, 0.20 mmol) were reacted according to Procedure C to give the product as a cream solid (0.020 g, 0.049 mmol, 24%); δH CDCl$_3$ 8.76 (1H, s), 8.62 (1H, s), 8.45 (1H, dd), 7.98 (1H, d), 7.57–7.65 (3H, m), 7.30–7.50 (5H, m), 7.05 (2H, d), 5.09 (2H, s), 2.71 (3H, s); m/z (M+1$^+$) 410.

Example 57

(4-Benzyloxy-phenyl)-(6-(5-(2-dimethylamino-ethyl)-1,2,4-oxadiazol-3-yl)-quinazolin-4-yl)-amine (4-(4-Benzyloxyanilino)quinazolin-6-yl)-(N-hydroxycarboximidamide) (0.20 mmol) and methyl 3-(dimethylamino)propionate (0.20 mmol) were reacted according to Procedure C to give the product as a cream solid (0.035 g, 0.075 mmol, 38%); δH [$^2$H$_6$]DMSO 10.22 (1H, s), 9.22 (1H, s), 8.57 (1H, s), 8.37 (1H, dd), 7.89 (1H, d), 7.69 (2H, d), 7.32–7.52 (5H, m), 7.07 (2H, d), 5.14 (2H, s), 3.21 (2H, t), 2.79 (2H, t), 2.20 (6H, s); m/z (M+1$^+$) 467.

Example 58

(4-Benzyloxy-phenyl)-(6-(5-(dimethylaminomethyl)-1,2,4-oxadiazol-3-yl)-quinazolin-4-yl)-amine ((4-Benzyloxy-phenyl)-quinazolin-6-yl)-(N-hydroxycarboximidamide) (0.20 mmol) and N,N-dimethylglycine methyl ester (0.20 mmol) were reacted according to Procedure C, followed by acidification with a solution of HCl in dioxane, to give the product as a yellow solid; δH [$^2$H$_6$]DMSO 9.51 (1H, s), 8.91 (1H, s), 8.63 (1H, d), 8.12 (1H, d), 7.64 (2H, d), 7.39–7.54 (5H, m), 7.16 (2H, d), 5.18 (2H, s), 3.02 (2H, s), 2.20 (6H, s); m/z (M+1$^+$) 453.

Example 59

(1-Benzyl-1H-indazol-5-yl)-(6-(5-(((2-methanesulphonyl-ethyl)-amino)-methyl)-1,2,4-oxadiazol-3-yl)-quinazolin-4-yl)-amine (4-(1-Benzyl-1H-indazol-5-yl)-quinazolin-6-yl)-(N-hydroxycarboximidamide) (0.123 g, 0.30 mmol) and N-(ethoxycarbonylmethyl)-N-(2-methylsulphonylethyl) trifluoroacetamide (0.183 g, 0.60 mmol) were reacted according to Procedure C. After being left overnight the reaction had not gone to completion so further sodium hydride (60% dispersion on mineral oil, 0.013 g, 0.33 mmol) and ester (0.183 g, 0.60 mmol) were added and the reaction was stirred for a further 24 hours. The mixture was concentrated in vacuo and the residue was purified by silica gel chromatography, eluting with 10% MeOH/CHCl$_3$ to give the title compound as a yellow solid (0.028 g, 0.050 mmol, 17%); δH [$^2$H$_6$]DMSO 10.39 (1H, s), 9.30 (1H, s), 8.59 (1H, s), 8.40 (1H, d), 8.11–8.22 (2H, m), 7.91 (1H, d), 7.72 (2H, m), 7.22–7.38 (5H, m), 5.68 (2H, s), 4.20 (2H, s), 3.28–3.38 (2H, obscured by water), 3.08 (2H, t), 3.05 (3H, s); m/z (M+1$^+$) 555.

Example 60

(1-Benzyl-1H-indazol-5-yl)-(6-(5-methanesulphonylmethyl-1,2,4-oxadiazol-3-yl)-quinazolin-4-yl)-amine (4-(1-Benzyl-1H-indazol-5-yl)-quinazolin-6-yl)-(N-hydroxycarboximidamide) (0.30 mmol) and ethyl 2-(methylsulphonyl)acetate (0.60 mmol) were reacted according to Procedure C to give the product as a yellow solid (0.030 g, 0.059 mmol, 20%); δH [$^2$H$_6$]DMSO 10.41 (1H, s), 9.30 (1H, s), 8.60 (1H, s), 8.42 (1H, dd), 8.13–8.21 (2H, m), 7.94 (1H, d), 7.69–7.76 (2H, m), 7.21–7.38 (5H, m), 5.69 (2H, s), 5.35 (2H, s), 3.30 (3H, s); m/z (M+1$^+$) 512.

Example 61

(1-Benzyl-1H-indazol-5-yl)-(6-(5-methyl-1,2,4-oxadiazol-3-yl)-quinazolin-4-yl0-amine (4-(1-Benzyl-1H-indazol-5-yl)-quinazolin-6-yl)-(N-hydroxycarboximidamide) (0.30 mmol) and ethyl acetate were reacted according to Procedure C to give the product as a yellow solid (0.065 g, 0.150 mmol, 50%); δH [$^2$H$_6$]DMSO 10.38 (1H, s), 9.28 (1H, d), 8.59 (1H, s), 8.38 (1H, dd), 8.21 (1H, s), 8.14 (1H, s), 7.90 (1H, d), 7.72 (2H, s), 7.22–7.38 (5H, m), 5.68 (2H, s), 2.73 (3H, s); m/z (M+1$^+$) 434.

Example 62

(1-Benzyl-1H-indazol-5-yl)-6-(5-(pyridin-3-ylmethyl)-1,2,4-oxadiazol-3-yl)-quinazolin-4-yl)-amine (4-(1-Benzyl-1H-indazol-5-yl)-quinazolin-6-yl)-(N-hydroxycarboximidamide) (0.30 mmol) and methyl 3-pyridineacetate (available from Salor) were reacted according to Procedure C to give the product as a yellow solid (0.028 g, 0.055 mmol, 18%); δH [$^2$H$_6$]DMSO 10.38 (1H, s), 9.26 (1H, s), 8.70 (1H, s), 8.54–8.60 (2H, m), 8.37 (1H, d), 8.14–8.20 (2H, m), 7.86–7.94 (2H, m), 7.68–7.77 (2H, m), 7.42–7.50 (1H, m), 7.20–7.38 (5H, m), 5.69 (2H, s), 4.59 (2H, s); m/z (M+1$^+$) 511.

Example 63

(1-Benzyl-1H-indazol-5-yl)-(6-(1-methylpyrrol-2-yl)-quinazolin-4-yl)-amine hydrochloride A stirred solution of 1-methyl-2-(tri-n-butylstannyl)pyrrole (prepared as described in H. M. R. Hoffmann et al. Synthesis, 1996, 164) (1.07 g, 2.89 mmol), (1-benzylindazol-5-yl)-(6-iodoquinazolin-4-yl)-amine hydrochloride (1.0 g, 1.95 mmol), triethylamine (0.4 ml, 0.29 g, 2.87 mmol) and 1,4-bis(diphenylphosphino)-butane palladium (II) chloride (0.1 g, catalytic) in dioxane (10 ml) was heated to reflux under a nitrogen atmosphere for 18 hours. The mixture was concentrated in vacuo and purified by silica gel chromatography, eluting with 2:1 i-hexane/EtOAc. Concentration of the appropriate fractions gave a yellow solid which was dissolved in EtOAc and treated with a solution of HCl in dioxane. The precipitate was collected by filtration, washed with EtOAc and dried at 60C in vacuo to give the product as a green-yellow solid (0.26 g, 0.557 mmol, 29%); δH [$^2$H$_6$]DMSO 11.95 (1H, s), 8.86–8.96 (2H, m), 8.18–8.27 (2H, m), 8.07 (1H, s), 7.99 (1H, d), 7.83 (1H, d), 7.65 (1H, dd), 7.22–7.40 (5H, m), 7.01 (1H, t), 6.49 (1H, dd), 6.19 (1H, t), 5.71 (2H, s), 3.82 (3H, s); m/z (M+1$^+$) 431.

Example 64

5-(4-(1-Benzyl-1H-indazol-5-yl)-quinazolin-6-yl)-1-methyl-pyrrole-2-carbaldehyde A stirred solution of 5-formyl-1-methyl-2-(tri-n-butylstannyl)pyrrole (prepared as described in F. Denat et al. J. Organometallic Chem., 423, 173, (1992)) (1.60 g, 4.02 mmol), (1-benzyl-1H-indazol-5-yl)-(6-iodoquinazolin-4-yl)-amine hydrochloride (1.0 g, 1.95 mmol), triethylamine (0.3 ml, 0.218 g, 2.2 mmol) and 1,4-bis(diphenylphosphino)-butane palladium (II) chloride (0.2 g, catalytic) in dioxane (20 ml) was heated to reflux under a nitrogen atmosphere for 18 hours (Procedure B). The mixture was concentrated in vacuo and purified by silica gel chromatography, eluting with 60%–100% EtOAc/i-hexane. Concentration of the appropriate fractions gave the product as a yellow solid (0.460 g, 1.00 mmol, 51%); δH [$^2$H$_6$]DMSO 10.00 (1H, s), 9.64 (1H, s), 8.73 (1H, s), 8.59 (1H, s), 8.22 (1H, s), 8.13–8.16 (1H, m), 8.01 (1H, dd), 7.86 (1H, d), 7.68–7.75 (2H, m), 7.19–7.37 (6H, m), 6.59 (1H, d), 5.68 (2H, s), 3.98 (3H, s); m/z (M+1$^+$) 459.

Example 65

1-(3-(4-(1-Benzyl-1H-indazol-5-ylamino)-quinazolin-6-yl)-1,2,4-oxadiazol-5-ylmethyl)-piperidin-4-one (4-(1-Benzyl-1H-indazol-5-ylamino)-quinazolin-6-yl)-(N-hydroxycarboximidamide) (0.30 mmol) and methyl 2-(4-piperidon-1-yl)acetate were reacted according to Procedure C to give the product as a yellow solid (0.035 g, 0.066 mmol, 22%); δH [$^2$H$_6$]DMSO 10.39 (1H, s), 9.28 (1H, d), 8.57 (1H, s), 8.39 (1H, d), 8.10-8.22 (2H, m), 7.91 (1H, d), 7.67–7.74 (2H, m), 7.21–7.37 (5H, m), 5.67 (2H, s), 4.20 (2H, s), 3.27–3.62 (4H, m, obscured by water), 2.82–2.99 (4H, m); m/z (M+1$^+$) 531.

Example 66

1-(3-(4-(1-Benzyl-1H-indazol-5-ylamino)-quinazolin-6-yl)-1,2,4-oxadiazol-5-ylmethyl)-pyrrolidin-2-one (4-(1-Benzylindazol-5-ylamino)-quinazolin-6-yl)-(N-hydroxycarboximidamide) (0.30 mmol) and ethyl 2-(pyrrolidin-2-on-1-yl)acetate (Aldrich) were reacted according to Procedure C to give the product as a yellow solid (0.072 g, 0.139 mmol, 46%); δH [$^2$H$_6$]DMSO 10.30 (1H, s), 9.27 (1H, d), 8.59 (1H, s), 8.39 (1H, dd), 8.15–8.20 (2H, m), 7.91 (1H, d), 7.70–7.74 (2H, m), 7.22–7.37 (5H, m), 5.69 (2H, s), 4.88 (2H, s), 3.55 (2H, t), 2.35 (2H, t), 2.00–2.11 (2H, m); m/z (M+1$^+$) 517.

Example 67

1-(3-(4-(1-Benzyl-1H-indazol-5-ylamino)-quinazolin-6-yl)-1,2,4-oxadiazol-5-ylmethyl)-imidazolidin-2,5-dione (4-(1-Benzyl-1H-indazol-5-ylamino)quinazolin-6-yl)-(N-hydroxycarboximidamide) (0.30 mmol) and methyl 2-(2,5-dioxo-imidazolidin-1-yl)acetate (Tarlton and McKay, Can. J. Chem., 36 (1958), 496) were reacted according to Procedure C to give the product as a yellow solid (0.097 g, 0.182 mmol, 61%); δH [$^2$H$_6$]DMSO 10.41(1H, s), 9.25 (1H, s), 8.58 (1H, s), 8.31–8.41 (2H, m), 8.12–8.19 (2H, m), 7.90 (1H, d), 7.70–7.73 (2H, m), 7.21–7.38 (5H, m), 5.68 (2H, s), 5.04 (2H, s), 4.11 (2H, s); m/z (M+1$^+$) 532.

Example 68

3-(4-(1-Benzyl-1H-indazol-5-ylamino)-quinazolin-6-yl)-4H-1,2,4-oxadiazolidin-3-one Carbonyl diimidazole (0.054 g, 0.33 mmol) was added to a solution of 4-(1-benzylindazol-5-yl)quinazolin-6-yl-(N-hydroxycarboximidamide) (0.123 g, 0.30 mmol) in dry THF (10 ml) under a nitrogen atmosphere, and the mixture was stirred at room temperature overnight. LC/MS showed complete disappearance of the starting material, so the mixture was treated with 1,5-diazabicyclo[4.3.0]non-5-ene (0.148 g, 1.2 mmol) and the mixture stirred for 20 hours. Concentration in vacuo, and chromatography on silica using a Bond Elut™ cartridge, eluting with CHCl$_3$ then a gradient of 2%–5% MeOH/CHCl$_3$, gave the product as a yellow solid (0.027 g, 0.062 mmol, 21%); δH [$^2$H$_6$]DMSO 10.25 (1H, brs), 9.08 (1H, s), 8.58 (1H, s), 8.12–8.23 (3H, m), 7.88 (1H, d), 7.71 (2H, s), 7.17–7.38 (5H, m), 5.68 (2H, s); m/z (M+1$^+$) 436.

Example 69

(1-Benzyl-1H-indazol-5-yl)-(6-(5-((2-methanesuphonyl-ethyl-amino)-methyl)-1-methyl-pyrrol-2-yl)-quinazolin-4-yl)-amine hydrochloride 5-(4-(1-Benzyl-1H-indazol-5-ylamino)-quinazolin-6-yl)-furan-2-carbaldehyde (0.10 g, 0.22 mmol) was stirred with 2-(methylsulphonyl)ethylamine (0.10 g, 0.81 mmol) and molecular sieves in dry dichloromethane (2 ml) for 30 min under a nitrogen atmosphere. Sodium triacetoxyborohydride (0.17 g, 0.80 mmol) and glacial acetic acid (2 drops) were added and the mixture was stirred at room temperature for 5 hours. The solution was decanted, washed with 8% aq. NaHCO$_3$, dried (Na$_2$SO$_4$) and concentrated in vacuo. The residue was purified by silica gel chromatography, eluting with 10% MeOH/EtOAc. Concentration of the appropriate fractions gave the free base of the product as a yellow solid, which was redissolved in EtOAc and treated with ethereal HCl. This mixture was concentrated in vacuo to give the title compound as a yellow solid (0.066 g, 0.103 mmol, 47%); δH [$^2$H$_6$]DMSO 12.15 (1H, s), 9.71 (2H, br s), 9.02 (1H, s), 8.89 (1H, s), 8.22 (1H, s), 8.16 (1H, d), 8.02–8.09 (2H, m), 7.83 (1H, d), 7.67 (1H, dd), 7.22–7.39 (5H, m), 6.51 (2H, s), 5.72 (2H, s), 4.38 (2H, s,) 3.81 (3H, s), 3.65–3.75 (2H, m), 3.38–3.50 (2H, m), 3.15 (3H, s); m/z (M+1$^+$) 566.

Example 70

(4-Benzyloxy-phenyl)-(6-(1-(3-N,N-dimethylaminopropyl)-imidazol-5-yl)-quinazolin-4-yl)-amine 1-(3-N,N-Dimethylaminopropyl)-5-tri-n-butylstannylimidazole (0.44 g) was treated with (4-benzyloxy-phenyl)-(6-iodoquinazolin-4-yl)amine (0.3 g) and silver (I) oxide (0.085 g), 1,4-bis(diphenylphosphino)butane palladium (II) chloride (37 mg) in dioxane (10 ml) at 90° C. under nitrogen for 60 hours. The cooled mixture was absorbed onto silica and purified by chromatography to give the title product (0.10 g); δH ($^2$H$_6$ DMSO) 9.80 (1H, s), 8.62 (1H, s), 8.57 (1H, s), 7.95 (1H, d), 7.85 (2H, d), 7.72 (2H, d), 7.45 (5H, m), 7.19 (1H, s), 7.10 (2H, d), 5.15 (2H, s), 4.22 (2H, t), 2.06 (2H, t), 2.01 (6H, s), 1.65 (2H, m); m/z (m+1)$^+$ 479.

Example 71

(1-Benzyl-1H-indazolyl)-(6-(1-(3-N,N-dimethylaminopropyl)-imidazol-5-yl)-quinazolin-4-yl)-amine Prepared via an analogous procedure to Example 70 from (1-Benzyl-1H-indazolyl)-(6-iodoquinazolin-4-yl)-amine and 1-(3-N,N-dimethylaminopropyl)-5-tri-n-butylstannylimidazole; δH ($^2$H$_6$ DMSO) 9.90 (1H, s), 8.60 (1H, s), 8.52 (1H, s), 8.17 (1H, s), 8.10 (1H, s), 7.90 (2H, d), 7.80 (2H, m), 7.65 (2H, m), 7.24 (5H, m), 7.12 (1H, s), 5.61 (2H, s), 4.14 (2H, t), 1.95 (2H, t), 1.90 (6H, s), 1.58 (2H, m); m/z (m+1)$^+$ 503.

Example 72

(4-Benzyloxy-phenyl)-(6-(1-(3-N,N-dimethylaminopropyl)-imidazol-2-yl)-quinazolin-4-yl)-amine 1-(N,N-Dimethylaminopropyl)-2-tri-n-butylstannylimidazole was treated with (4-benzyloxy-phenyl)-(6-iodoquinazolin-4-yl)amine as described above in Example 70 to give the title product; δH ($^2$H$_6$ DMSO) 9.90 (1H, s), 8.73 (1H, s), 8.54 (1H, s), 8.01 (1H, d), 7.82 (1H, d), 7.69 (2H, d), 7.40 (6H, m), 7.06 (3H, m), 5.12 (2H, s), 4.08 (2H, t), 2.57 (2H, m), 2.48 (6H, s), 1.93 (2H, m); m/z (m+1)$^+$ 479.

Example 73

(1-Benzyl-1H-indazolyl)-(6-(1-(3-N,N-dimethylaminopropyl)-imidazol-5-yl)-quinazolin-4-yl)-amine Prepared via an analogous procedure to Example 72 from (1-benzyl-1H-indazolyl)-(6-iodoquinazolin-4-yl)-amine and 1-(3-N,N-dimethylaminopropyl)-2-tri-n-butylstannylimidazole; δH ($^2$H$_6$ DMSO) 9.90 (1H, s), 8.88 (1H, s), 8.67 (1H, s), 8.41 (1H, s), 8.31 (1H, s), 8.23 (1H, s), 8.15 (1H, d), 7.94 (1H, d), 7.80 (2H, m), 7.51 (1H, s), 7.48 (5H, m), 7.20 (1H, s), 5.77 (2H, s), 4.25 (2H, t), 2.14 (2H, t), 2.07 (6H, s), 1.86 (2H, m); m/z (m+1)$^+$ 503.

Example 74

(4-Benzyloxy-phenyl)-(6-(5-trifluoromethyl-1,3,4-oxadiazol-2-yl)-quinazolin-4-yl)-amine The title compound was prepared according to Procedure A from 4-benzyloxyaniline and 4-chloro-6-(5-trifluoromethyl-1,3,4-oxadiazol-2-yl)-quinazoline; δH [$^2$H$_6$] DMSO 11.69(1H, bs), 9.53(1H, s), 8.91 (1H, s), 8.65(1H, dd), 8.11 (1H, d), 7.64(2H, d), 7.45(5H, m), 7.15(2H, d), 5.19(2H, s); m/z (M+1$^+$) 464.

Example 75

(1-(2-Fluoro-benzyl)-1H-indazol-5-yl)-(6-(5-trifluoromethyl-1,3,4-oxadiazol-2-yl)-quinazolin-4-yl)-amine The title compound was prepared according to Procedure A from 1-(2-fluoro-benzyl)-1H-indazol-5-ylamine and 4-chloro-6-(5-trifluoromethyl-1,3,4-oxadiazol-2-yl)-quinazoline; δH [$^2$H$_6$]DMSO 11.79(1H, bs), 9.53(1H, s), 8.89(1H, s), 8.77(1H, dd), 8.21(1H, s), 8.11(1H, m), 8.10 (1H, d), 7.84(1H, d), 7.70(1H, dd), 7.37(1H, m), 7.24 (1H, m), 7.18 (2H, m), 5.76(2H, s); m/z (M+1$^+$) 506.

Example 76

(1-(3-Fluoro-benzyl)-1H-indazol-5-yl)-(6-(5-trifluoromethyl-1,3,4-oxadiazol-2-yl)-quinazolin-4-yl)-amine The title compound was prepared according to Procedure A from 1-(3-fluoro-benzyl)-1H-indazol-5-ylamine and 4-chloro-6-(5-trifluoromethyl-1,3,4-oxadiazol-2-yl)-quinazoline; δH [$^2$H$_6$]DMSO 11.84(1H, bs), 9.54(1H, s), 8.89(1H, s), 8.77(1H, dd), 8.25(1H, s), 8.11(2H, m), 7.87 (1H, d), 7.69(1H, dd), 7.39(1H, m), 7.10 (3H, m), 5.73(2H, s); m/z (M+1$^+$) 506.

Example 77

(1-(4-Fluoro-benzyl)-1H-indazol-5-yl)-(6-(5-trifluoromethyl-1,3,4-oxadiazol-2-yl)-quinazolin-4-yl)-amine The title compound was prepared according to Procedure A from 1-(4-fluoro-benzyl)-1H-indazol-5-ylamine and 4-chloro-6-(5-trifluoromethyl-1,3,4-oxadiazol-2-yl)-quinazoline; δH [$^2$H$_6$]DMSO 11.91(1H, bs), 9.55(1H, s), 8.91(1H, s), 8.69(1H, dd), 8.23(1H, s), 8.14(2H, m), 7.88 (1H, d), 7.69(1H, dd), 7.36(2H, m), 7.18 (2H, dd), 5.71(2H, s); m/z (M+1$^+$) 506

Example 78

(1-Benzyl-1H-indazol-5-yl)-(7-(5-methyl-[1,3,4]oxadiazol-2-yl)-quinazolin-4-yl)-amine hydrochloride The crude solid 4-Chloro-7-(5-Methyl-[1,3,4]oxadiazol-2-yl)-quinazoline was suspended in dry acetonitrile. 1-Benzyl-1H-indazol-5-ylamine (0.03 g) was added and the mixture heated at reflux for 18 hours under nitrogen (Procedure A). The mixture was cooled and the title compound collected by filtration; δH [$^2$H$_6$]DMSO 11.82(1H, bs), 9.08(1H, s), 8.99(1H, s), 8.47(1H, s), 8.44(1H, d), 8.37(1H, s), 8.17(1H, s), 7.89(1H, d), 7.72(1H, d), 7.35(5H, m), 5.80(2H, s) 2.72 (3H, s); m/z (M+1+) 434.

Example 79

(1-Benzyl-1H-indazol-5-yl)-(7-(3-methyl-3H-imidazol-4-yl)quinazolin-4-yl)-amine

Prepared according to Procedure B from (1-benzyl-1H-indazol-5-yl)-(7-iodoquinazolin-4-yl)-amine hydrochloride and (3-methyl-3H-imidazol-4-yl) tri-n-butylstannane; δH [$^2$H$_6$]DMSO 11.85(1H, bs), 9.25(1H, s), 9.19(1H, s), 9.02 (1H, d), 8.93(1H, s), 8.16(2H, d), 8.06(2H, d), 7.78(1H, d), 7.61(1H, dd), 7.22(5H, m), 5.66(2H, s) 3.92 (3H, s); m/z (M+1+) 432.

Example 80

(1-Benzyl-1H-indazol-5-yl)-[7-(furan-2-yl)-quinazolin-4-yl]-amine hydrochloride

Prepared according to Procedure B from (1-benzyl-1H-indazol-5-yl)-(7-iodoquinazolin-4-yl)-amine hydrochloride and (furan-2-yl)-tri-n-butylstannane; δH [$^2$H$_6$]DMSO 9.94 (1H, bs), 8.61 (1H, d), 8.55(1H, s), 8.21 (2H, d), 8.00(3H, m), 7.73(2H, s), 7.30(6H, s), 6.74(1H, s), 5.72(2H, s); m/z (M+1+) 418.

Example 81
(1-Benzyl-1H-indazol-5-yl)-[7-(5-(1 3-dioxolan-2-yl)-furan-2-yl)quinazolin-4-yl]amine hydrochloride Prepared according to Procedure B from (1-benzyl-1H-indazol-5-yl)-(7-iodoquinazolin-4-yl)-amine hydrochloride and 5-(1,3-dioxolan-2-yl)-2-(tri-n-butylstannyl)furan; tlc Rf, 0.25 (100% EtOAc on silica); m/z (M+1+) 490.

Example 82
5-[4-(1-Benzyl-1H-indazol-5-ylamino)-quinazolin-7-yl]-furan-2-carbaldehyde (1-Benzyl-1H-indazol-5-yl)-[7-(5-(1,3-dioxolan-2-yl)furan-2-yl)quinazolin-4-yl]-amine hydrochloride (0.27 g) was stirred in THF:2N HCl (2:1, 15 ml) at 20° C. for 1 hour. Filtration gave 5-[4-(1-benzyl-1H-indazol-5-ylamino)-quinazolin-7-yl]-furan-2-carbaldehyde, used directly in the subsequent synthetic step.

Example 83
(1-Benzyl-1H-indazol-5-yl)-[7-{5-[(2-methanesulphonyl-ethylamino)-methyl]-furan-2-yl}-quinazolin-4-yl]-amine Prepared by an analogous method to Example 10 from 5-[4-(1-benzyl-1H-indazol-5-ylamino)-quinazolin-7-yl]-furan-2-carbaldehyde and 2-methanesulphonylethylamine; δH [$^2$H$_6$] DMSO 9.92(1H, bs), 8.60(1H, d), 8.55(1H, s), 8.25(1H, s), 8.17(1H, s), 8.00(2H, m), 7.72(2H, m), 7.30 (6H, m), 6.53 (1H, d), 5.72(2H, s) 4.55 (1H, m), 3.87 (2H, m), 3.35 (2H, m), 3.08 (3H, s), 3.04 (2H, m); m/z (M+1+) 553.

Example 84
(S)-1-{5-[4-(1-Benzyl-1H-indazol-5-ylamino)-quinazolin-7-yl]-furan-2-yl-methyl}-pyrrolidine-2-carboxylic acid amide Prepared by an analogous method to Example 10 from 5-[4-(1-benzyl-1H-indazol-5-yl)-quinazolin-7-yl]-furan-2-carbaldehyde and S-(–)-prolineamide; δH [$^2$H$_6$] DMSO 9.83(1H, bs), 8.50(1H, d), 8.47(1H, s), 8.15(1H, s), 8.08(1H, s), 7.90(2H, m), 7.65(2H, m), 7.20(6H, m), 7.05 (1H, m), 6.48 (1H, d), 5.62(2H, s) 3.80 (1H, d), 3.70 (1H, d), 3.70 (2H, s), 3.03 (2H, m), 2.00 (1H, m), 1.70 (3H, m); m/z (M+1+) 544.

Example 85
(4-Benzyloxy-phenyl)-(6-(3-methyl-[1,2]oxazol-4-yl)-quinazolin-4-yl)-amine (4-Benzyloxy-phenyl)-(6-iodoquinazolin-4-yl)-amine hydrochloride (0.35 g) in dioxan (10 ml) under nitrogen was treated with 4-tributylstannyl-3-methylisoxazole (prepapred according to the literature method: Heterocycles, (1996), 43(6), 1301–1304) (0.4 g), silver oxide (0.092 g), triethylamine (0.1 ml) and [1.4-bis(diphenylphosphino)butane] palladium (II) chloride (0.1 g) at 90° C. for 16 hours. The mixture was cooled, adsorbed onto silica and purified by chromatography. Trituration from hexane and filtration gave the title compound (0.20 g); δH [$^2$H$_6$]DMSO 9.78(1H, bs), 9.22(1H, s), 8.57(1H, s), 8.53(1H, s), 7.98(1H, d), 7.83(1H, d), 7.67(2H, d), 7.42(5H, m), 7.09(1H, d), 5.64(2H, s) 2.51 (3H, s); m/z (M+1)+ 409.

Example 86
(4-Benzyloxy-phenyl)-(6-(4-(1,3-dioxolan-2-yl)-3-methyl-3H-imidazol-2-yl)-quinazolin-4-yl)-amine 1-Methyl-5-(1,3-dioxolan-2-yl)-imidazole (0.09 g) in dry THF (5 ml) under N$_2$ was cooled to –78° C. and treated with n-butyl lithium (0.4 ml, 1.6 M). After 30 minutes, tributyl tin chloride (0.17 ml) was added, the mixture allowed to warm to 20° C. and stirred for 1 hour. (4-Benzyloxy-phenyl)-(6-iodoquinazolin-4-yl)-amine (0.191 g), catalytic quantities of 1.4-bis-(diphenylphosphino)-butane palladium (II) chloride and silver (I) oxide (0.052 g) were added and the mixture heated at reflux for 18 hours. The mixture was absorbed onto silica and chromatographed to give the title compound (0.045 g); m/z (M+1)+ 480.

Example 87
2-(4-(4-Benzyloxy-phenylamino)-quinazolin-6-yl)-3-methyl-3H-imidazol-4-carbaldehyde (4-Benzyloxy-phenyl)-(6-(4-(1,3-dioxolan-2-yl)-3-methyl-3H-imidazol-2-yl)-quinazolin-4-yl)-amine (0.06 g) was treated with acetone (5 ml) and 2N HCl at reflux for 2 hours. The mixture was cooled, partitioned between ethyl acetate and 2N sodium carbonate. The organic phase was dried and concentrated in vacuo to give the title compound which was used directly in any subsequent synthetic step; m/z (M+1)+ 436.

Examples 88 to 95

The following compounds, and their hydrochlorides if appropriate, are prepared by analogous techniques using the corresponding starting materials:

(4-Benzyloxy-phenyl)-(6-(imidazol-2-yl)-quinazolin-4-yl)-amine;

(4-Benzyloxy-phenyl)-(6-[5-(4-methyl-piperazinylmethyl)-1-methylimidazol-2-yl]-quinazolin-4-yl)-amine;

(4-Benzyloxy-phenyl)-(6-[5-(N,N-dimethylaminomethyl)-1-methylimidazol-2-yl]-quinazolin-4-yl)-amine;

(4-Benzyloxy-phenyl)-(6-[5-(4-methyl-piperazinylmethyl)-imidazol-2-yl]-quinazolin-4-yl)-amine;

(4-Benzyloxy-phenyl)-(6-[5-(N,N-dimethylaminomethyl)-imidazol-2-yl]-quinazolin-4-yl)-amine;

(4-Benzyloxy-phenyl)-(6-[1-(4-methyl-piperazinylmethyl)-imidazol-2-yl]-quinazolin-4-yl)-amine;

(4-Benzyloxy-phenyl)-(6-[1-(N,N-dimethylaminomethyl)-imidazol-2-yl]-quinazolin-4-yl)-amine;

(4-Benzyloxy-phenyl)-(6-(5-carboxymethylaminomethyl-furan-2-yl)-quinazolin-4-yl)-amine.

Biological Data

Compounds of the present invention were tested for protein tyrosine kinase inhibitory activity in substrate phosphorylation assays and cell proliferation assays.

The substrate phosphorylation assays use baculovirus expressed, recombinant constructs of the intracellular domains of c-erbB-2 and c-erbB-4 that are constitutively active and EGFr isolated from solubilised A431 cell membranes. The method measures the ability of the isolated enzymes to catalyse the transfer of the γ-phosphate from ATP onto tyrosine residues in a biotinylated synthetic peptide (Biotin-GluGluGluGluTyrPheGluLeuVal). The enzyme is incubated for 30 minutes, at room temperature, with 10 mM MnCl$_2$, ATP and peptide at Km concentrations, and test compound (diluted from a 5 mM stock in DMSO, final DMSO concentration is 2%) in 40 mM HEPES buffer, pH 7.4. The reaction is stopped by the addition of EDTA (final concentration 0.15 mM) and a sample is transferred to a streptavidin-coated 96-well plate. The plate is washed and level of phosphotyrosine on the peptide is determined using a Europium-labelled antiphosphotyrosine antibody and quantified with a time-resolved fluorescence technique. The results are shown in Table 1 as the IC$_{50}$ values in nM.

The cell proliferation assay uses an immortalised human breast epithelial cell line (HB4a) which has been transformed by over-expression of c-erbB-2. Growth of these cells in low serum is dependent upon the c-erbB-2 tyrosine kinase activity. The specificity of the effect of the test compounds on tyrosine kinase dependent growth over general toxicity is assessed by comparison to an HB4a cell line which has been transfected with ras. Cells are plated at 3000/well in 96-well plates in 0.1 ml medium and allowed to attach overnight. test compound is added in 0.1 ml medium, with a final concentration of 0.5% DMSO, and the plates incubated for 4 days at 37° C. The cells are then examined microscopically for evidence of morphological detransformation and cell mass is estimated by staining with methylene blue and measuring the absorbance at 620 nm. The results are shown in Table 1 below as the $IC_{50}$ values in nM. Activity against a range of naturally occurring EGFr or c-erbB-2 over-expressing human tumour cell lines (BT474-breast, HN5-head and neck, N87-gastric and Calu3-lung) is assessed with selected compounds by the same methodology. The results are also shown in Table 1 below as the $IC_{50}$ values in nM.

TABLE 1

| | Substrate Phosphorylation | | | Cell Proliferation | | | | | |
|---|---|---|---|---|---|---|---|---|---|
| Example | EGFr | erbB-2 | erbB-4 | HB4a erbB-2 | HB4a ras | BT474 | N87 | Calu3 | HN5 |
| 1 | | 40 | 2500 | | | | | | |
| 2 | | 21 | 500 | 1000 | 8300 | | | 4600 | 26000 |
| 3 | | 29 | 8600 | 23000 | 16000 | | | | |
| 4 | | 35 | 6400 | 50000 | 50000 | | | | |
| 5 | | 20 | 320 | 400 | 19000 | | | 780 | 1400 |
| 6 | 680 | 110 | 1000 | 1600 | 16000 | 1900 | 1800 | 5800 | 5200 |
| 7 | | 36 | 1500 | 1300 | 12000 | | | 4700 | 5500 |
| 8 | | 150 | >10000 | | | | | | |
| 9 | | 24 | 430 | 550 | 5700 | | | | |
| 10 | | 52 | 780 | 1500 | 7100 | | | 2200 | 2100 |
| 11 | 160 | 36 | 660 | 580 | 14000 | 180 | 480 | 930 | 940 |
| 12 | 220 | 120 | 1400 | 840 | 2500 | | | | |
| 13 | 300 | 350 | 2300 | 450 | 2200 | | | | |
| 14 | 200 | 34 | 1200 | 680 | 5000 | | | | |
| 15 | 540 | 50 | 2300 | 2600 | 3200 | | | | |
| 18 | | 45 | 34 | 9 | >50000 | 2 | 180 | 360 | 840 |
| 19 | 8 | 1 | 240 | 50 | 25000 | 110 | 380 | 920 | 670 |
| 20 | 140 | 3 | | 6200 | >50000 | | | | |
| 21 | 28 | 9 | | 2300 | >50000 | | | | |
| 22 | 8 | | | 430 | 27000 | 97 | 600 | 2200 | 910 |
| 23 | 32 | 1 | | 31000 | >50000 | | | | |
| 24 | 15 | 2 | | 17000 | >50000 | | | | |
| 25 | 22 | 15 | | 750 | >50000 | | | | |
| 26 | 18 | 7 | | 650 | >50000 | | | | |
| 27 | 47 | 10 | | 6500 | 50000 | | | | |
| 28 | 50 | 7 | | 5300 | >50000 | | 8200 | | |
| 29 | 23 | 3 | | 2500 | >50000 | 770 | 2400 | 23000 | 4400 |
| 30 | 38 | 6 | | 5400 | 50000 | | | 18000 | |
| 31 | 9 | | | 1100 | >50000 | | | | |
| 38 | 140 | 88 | 520 | | | | | | |
| 40 | | 3 | 970 | >50000 | >50000 | | | | |
| 41 | 2 | 10 | 1000 | 610 | 35000 | 260 | 1400 | 5300 | 970 |
| 42 | | 7 | | 570 | 20000 | | | | |
| 44 | | | 1300 | 1400 | 31000 | | | | |
| 47 | | 490 | 5000 | | | | | | |
| 48 | | 38 | 1100 | 80 | 9500 | | | | |
| 49 | | 33 | | 470 | 3500 | | | | |
| 50 | | 12 | 100 | 860 | 7100 | | | | |
| 51 | | 20 | 5800 | 38000 | 21000 | | | | |
| 53 | 13 | | | 1800 | 36000 | | | | |
| 54 | | 24 | 280 | 140 | 7400 | | | | |
| 55 | | 10 | 1000 | 2000 | 20000 | | | | |
| 56 | | 260 | >10000 | 1700 | >50000 | | | | |
| 57 | | 83 | | 1200 | 2700 | | | | |
| 58 | | 6 | | 8600 | 28000 | | | | |
| 59 | 11 | | | 790 | 11000 | | | | |
| 60 | 1900 | | | 540 | 50000 | | | | |
| 61 | 810 | | | 500 | 3100 | | | | |
| 62 | 13 | 100 | | 500 | 3700 | | | | |
| 85 | | 130 | 9700 | 2100 | 2300 | | | | |

I claim:
1. A method of treating a susceptible cancer in a human or animal subject in need thereof, comprising administering to said subject an effective amount of a compound of formula (I):

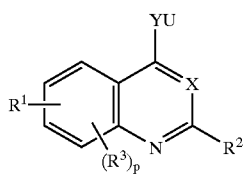

or a salt or solvate thereof;
wherein X is N or CH;
Y is a group W(CH$_2$), (CH$_2$)W, or W, in which W is O, S(O)$_m$ wherein m is 0, 1 or 2, or NR$^a$ wherein R$^a$ is hydrogen or a C$_{1-8}$ alkyl group;
R$^1$ is a 5- or 6-membered heterocyclic ring containing 1 to 4 heteroatoms selected from the group N, O or S(O)$_m$, wherein m is as defined above, with the provisos that the ring does not have two adjacent O or S(O)$_m$ atoms and that where the ring has only N as heteroatom(s) the ring is C-linked to the quinazoline or quinoline ring, R$^1$ being optionally substituted by one or more R$^3$ groups;
each R$^3$ is independently selected from the group consisting of amino, hydrogen, halogen, hydroxy, nitro, carboxy, formyl, cyano, trifluoromethyl, trifluoromethoxy, carbamoyl, ureido, guanidino, C$_{1-8}$ alkyl, C$_{1-8}$ alkoxy, C$_{3-8}$ cycloalkoxyl, C$_{4-8}$ alkylcycloalkoxy, C$_{1-8}$ alkylcarbonyl, C$_{1-8}$ alkoxycarbonyl, N-C$_{1-4}$ alkylcarbamoyl, N,N-di-[C$_{1-4}$ alkyl]carbamoyl, hydroxyamino, C$_{1-4}$ alkoxyamino, C$_{2-4}$ alkanoyloxyamino, C$_{1-4}$ alkylamino, di[C$_{1-4}$ alkyl]amino, di-[C$_{1-4}$ alkyl]amino-C$_{1-4}$ alkylene-(C$_{1-4}$ alkyl)amino, C$_{1-4}$ alkylamino-C$_{1-4}$ alkylene-(C$_{1-4}$ alkyl)amino, hydroxy-C$_{1-4}$ alkylene-(C$_{1-4}$ alkyl)amino, phenyl, phenoxy, 4-pyridon-1-yl, pyrrolidin-1-yl, imidazol-1-yl, piperidino, morpholino, thiomorpholino, thiomorpholino-1-oxide, thiomorpholino-1,1-dioxide, piperazin-1-yl, 4-C$_{1-4}$ alkylpiperazin-1-yl, dioxolanyl, C$_{1-8}$ alkylthio, arylthio, C$_{1-4}$ alkylsulphinyl, C$_{1-4}$ alkylsulphonyl, arylsulphonyl, arylsulphonyl, halogen O-C$_{1-4}$ alkyl, hydroxy-C$_{1-4}$ alkyl, C$_{2-4}$ alkanoyloxy-C$_{1-4}$ alkyl, C$_{1-4}$ alkoxy-C$_{1-4}$ alkyl, carboxy-C$_{1-4}$ alkyl, formyl-C$_{1-4}$ alkyl, C$_{1-4}$ alkoxycarbonyl-C$_{1-4}$-alkyl, carbamoyl-C$_{1-4}$ alkyl, N-C$_{1-4}$ alkylcarbamoyl-C$_{1-4}$alkyl, N,N-di-[C$_{1-4}$ alkyl]carbamoyl-C$_{1-4}$alkyl, amino-C$_{1-4}$ alkyl, C$_{1-4}$ alkylamino-C$_{1-4}$ alkyl, di-[C$_{1-4}$ alkyl]amino-C$_{1-4}$ alkyl, phenyl-C$_{1-4}$ alkyl, 4-pyridon-1-yl-C$_{1-4}$ alkyl, pyrrolidin-1-yl-C$_{1-4}$ alkyl, imidazol-1-yl-C$_{1-4}$ alkyl, piperidino-C$_{1-4}$ alkyl, morpholino-C$_{1-4}$ alkyl, thiomorpholino-C$_{1-4}$ alkyl, thiomorpholino-1-oxide-C$_{1-4}$alkyl, thiomorpholino-1,1-dioxide-C$_{1-4}$alkyl, piperazin-1-yl-C$_{1-4}$alkyl, 4-C$_{1-4}$ alkylpiperazin-1-yl-C$_{1-4}$ alkyl, hydroxy-C$_{2-4}$ alkoxy-C$_{1-4}$ alkyl, C$_{1-4}$ alkoxy-C$_{2-4}$ alkoxy-C$_{1-4}$ alkyl, hydroxy-C$_{2-4}$ alkylamino-C$_{1-4}$ alkyl, C$_{1-4}$ alkoxy-C$_{2-4}$ alkylamino-C$_{1-4}$ alkyl, C$_{1-4}$ alkylthio-C$_{1-4}$ alkyl, C$_{1-4}$ alkylsulphinyl-C$_{1-4}$ alkyl, C$_{1-4}$ alkylsulphonyl-C$_{1-4}$ alkyl, hydroxy-C$_{2-4}$ alkylthio-C$_{1-4}$ alkyl, C$_{1-4}$ alkoxy-C$_{2-4}$ alkylthio-C$_{1-4}$ alkyl, phenoxy-C$_{1-4}$ alkyl, anilino-C$_{1-4}$ alkyl, phenylthio-C$_{1-4}$ alkyl, cyano-C$_{1-4}$ alkyl, halogen O-C$_{2-4}$ alkoxy, hydroxy-C$_{2-4}$ alkoxy, C$_{2-4}$ alkanoyloxy-C$_{2-4}$ alkoxy, C$_{1-4}$ alkoxy-C$_{2-4}$ alkoxy, carboxy-C$_{1-4}$ alkoxy, formyl-C$_{1-4}$ alkoxy, C$_{1-4}$ alkoxycarbonyl-C$_{1-4}$ alkoxy, carbamoyl-C$_{1-4}$ alkoxy, N-C$_{1-4}$ alkylcarbamoyl-C$_{1-4}$ alkoxy, N,N-di-[C$_{1-4}$ alkyl]carbamoyl-C$_{1-4}$ alkoxy, amino-C$_{2-4}$ alkoxy, C$_{1-4}$ alkylamino-C$_{2-4}$ alkoxy, di-[C$_{1-4}$ alkyl]amino-C$_{2-4}$ alkoxy, di-[C$_{1-4}$ alkyl-C$_{2-4}$ alkoxy]amino-C$_{2-4}$ alkoxy, C$_{2-4}$ alkanoyloxy, hydroxy-C$_{2-4}$ alkanoyloxy, C$_{1-4}$alkoxy-C$_{2-4}$ alkanoyloxy, phenyl-C$_{1-4}$ alkoxy, phenoxy-C$_{2-4}$ alkoxy, anilino-C$_{2-4}$ alkoxy, phenylthio-C$_{2-4}$ alkoxy, 4-pyridin-1-yl-C$_{2-4}$ alkoxy, piperidino-C$_{2-4}$ alkoxy, morpholino-C$_{2-4}$ alkoxy, thiomorpholino-C$_{2-4}$ alkoxy, thiomorpholino-1-oxide-C$_{2-4}$ alkoxy, thiomorpholino-1,1-dioxide-C$_{2-4}$ alkoxy, piperazin-1-yl-C$_{2-4}$ alkoxy, 4-C$_{1-4}$ alkylpiperazin-1-yl-C$_{2-4}$ alkoxy, pyrrolidin-1-yl-C$_{2-4}$ alkoxy, imidazol-1-yl-C$_{2-4}$ alkoxy, halogeno-C$_{2-4}$ alkylamino, hydroxy-C$_{2-4}$ alkylamino, C$_{2-4}$ alkanoyloxy-C$_{2-4}$ alkylamino, C$_{1-4}$ alkoxy-C$_{2-4}$ alkylamino, carboxy-C$_{1-4}$ alkylamino, C$_{1-4}$ alkoxycarbonyl-C$_{1-4}$ alkylamino, carbamoyl-C$_{1-4}$ alkylamino, N-C$_{1-4}$ alkylcarbamoyl-C$_{1-4}$ alkylamino, N,N-di-[C$_{1-4}$ alkyl]carbamoyl-C$_{1-4}$ alkylamino, amino-C$_{2-4}$ alkylamino, C$_{1-4}$ alkylamino-C$_{2-4}$ alkylamino, di-[C$_{1-4}$alkyl]amino-C$_{2-4}$ alkylamino, phenyl-C$_{1-4}$ alkylamino, phenoxy-C$_{2-4}$ alkylamino, anilino-C$_{2-4}$ alkylamino, 4-pyridon-1-yl-C$_{2-4}$ alkylamino, pyrrolidin-1-yl-C$_{2-4}$ alkylamino, imidazol-1-yl-C$_{2-4}$ alkylamino, piperidino-C$_{2-4}$ alkylamino, morpholino-C$_{2-4}$ alkylamino, thiomorpholino-C$_{2-4}$ alkylamino, thiomorpholino-1-oxide-C$_{2-4}$ alkylamino, thiomorpholino-1,1-dioxide-C$_{2-4}$ alkylamino, piperazin-1-yl-C$_{2-4}$alkylamino, 4-(C$_{1-4}$alkyl)piperazin-1-yl-C$_{2-4}$alkylamino, phenylthio-C$_{2-4}$ alkylamino, C$_{2-4}$ alkanoylamino, C$_{1-4}$ alkoxycarbonylamino, C$_{1-4}$ alkylsulphonylamino, C$_{1-4}$ alkylsulphinylamino, benzamido, benzenesulphonamido, 3-phenylureido, 2-oxopyrrolidin-1-yl, 2,5-dioxopyrrolidin-1-yl, halogeno-C$_{2-4}$ alkanoylamino, hydroxy-C$_{2-4}$ alkanoylamino, hydroxy-C$_{2-4}$ alkanoyl-(C$_{1-4}$ alkyl)-amino, C$_{1-4}$ alkoxy-C$_{2-4}$ alkanoylamino, carboxy-C$_{2-4}$ alkanoylamino, C$_{1-4}$ alkoxycarbonyl-C$_{2-4}$ alkanoylamino, carbamoyl-C$_{2-4}$ alkanoylamino, N-C$_{1-4}$ alkylcarbamoyl-C$_{2-4}$ alkanoylamino, N,N-di-[C$_{1-4}$ alkyl]carbamoyl-C$_{2-4}$ alkanoylamino, amino-C$_{2-4}$ alkanoylamino, C$_{1-4}$ alkylamino-C$_{2-4}$ alkanoylamino and di-[C$_{1-4}$ alkyl]amino-C$_{2-4}$ alkanoylamino; and wherein said benzamido or benzenesulphonamido substituent or any anilino, phenoxy or phenyl group on a R$^3$ substituent optionally has one or two halogeno, C$_{1-4}$ alkyl or C$_{1-4}$ alkoxy substituents; and wherein any substituent having a heterocyclic ring optionally has one or two halogeno, C$_{1-4}$ alkyl or C$_{1-4}$ alkoxy substituents on said ring; and wherein any substituent having a heterocyclic ring optionally has one or two oxo or thioxo substituents on said ring;
or R$^3$ is selected from the group consisting of M$^1$-M$^2$-M$^3$-M$^4$, M$^1$-M$^5$ and M$^1$-M$^2$-M$^{3'}$-M$^6$
wherein
M$^1$ is a C$_{1-4}$ alkyl group, wherein optionally a CH$_2$ group is replaced by a CO group;
M$^2$ is NR$^{12}$ or CR$^{12}$R$^{13}$, in which R$^{12}$ and R$^{13}$ each independently are H or C$_{1-4}$ alkyl;
M$^3$ is a C$_{1-4}$ alkyl group;
M$^{3'}$ is a C$_{1-4}$ alkyl group or is absent;
M$^4$ is selected from the group consisting of CN, NR$^{12}$S(O)$_m$R$^{13}$, S(O)$_m$NR$^{14}$R$^{15}$, CONR$^{14}$R$^{15}$, S(O)$_m$R$^{13}$ and $CO_2R^{13}$, in which $R^{12}$, $R^{13}$ and m are as defined above and $R^{14}$ and $R^{15}$ each independently are H or $C_{1-4}$ alkyl, or $R^{14}$ and $R^{15}$ together with the nitrogen atom to which they are attached form a 5- or 6-membered ring optionally containing 1 or 2 additional heteroatoms selected from N, O or $S(O)_m$ in which ring any nitrogen atom present is optionally substituted with a $C_{1-4}$ alkyl group, and which ring optionally has one or two oxo or thioxo substituents;

$M^5$ is the group $NR^{14}R^{15}$, wherein $R^{14}$ and $R^{15}$ are as defined above, or $M^5$ is the group

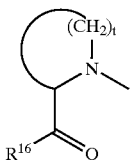

in which t is 2 to 4 and $R^{16}$ is OH, $OC_{1-4}$ alkyl or $NR^{14}R^{15}$; and $M^6$ is selected from the group consisting of a $C_{3-6}$ cycloalkyl group, the group $NR^{14}R^{15}$, wherein $R^{14}$ and $R^{15}$ are as defined above, and a 5- or 6-membered heterocyclic ring system containing 1 to 4 heteroatoms selected from N, O or S;

and p is 0 to 3; or when p is 2 or 3, two adjacent $R^3$ groups together form an optionally substituted methylenedioxy or ethylenedioxy group;

$R^2$ is selected from the group consisting of hydrogen, halogen, trifluoromethyl, $C_{1-4}$ alkyl and $C_{1-4}$ alkoxy;

U is phenyl or a 5 to 10-membered mono or bicyclic ring system in which one or more of the carbon atoms is optionally replaced by a heteroatom independently selected from N, O and $S(O)_m$, wherein m is 0,1 or 2, and wherein U is substituted by at least one independently selected $R^6$ group and U is optionally substituted by at least one independently selected $R^4$ group;

each $R^4$ is independently selected from the group consisting of hydrogen, hydroxy, halogen, $C_{1-4}$ alkyl, $C_{1-4}$ alkoxy, $C_{1-4}$ alkylamino, di-[$C_{1-4}$ alkyl]amino, $C_{1-4}$ alkylthio, $C_{1-4}$ alkylsulphinyl, $C_{1-4}$ alkylsulphonyl, $C_{1-4}$ alkylcarbonyl, $C_{1-4}$ alkylcarbamoyl, di-[$C_{1-4}$ alkyl]carbamoyl, carbamyl, $C_{1-4}$ alkocycarbonyl, cyano, nitro and trifluoromethyl;

each $R^6$ is independently a group $ZR^7$ wherein Z is joined to $R^7$ through a ($CH_2$) p group in which p is 0, 1 or 2 and Z is selected from a group consisting of $V(CH_2)$, $V(CF_2)$, $(CH_2)V$, $(CF_2)V$, $V(CRR')$, $V(CHR)$ and V where R and R' are each $C_{1-4}$ alkyl and in which V is a hydrocarbyl group containing 0, 1 or 2 carbon atoms, carbonyl, dicarbonyl, CH(OH), CH(CN), sulphonamide, amide, O, S C $O)_m$ or $NR^b$ where $R^b$ is hydrogen or $R^b$ is $C_{1-4}$ alkyl; and $R^7$ is an optionally substituted $C_{3-6}$ cycloalkyl; or an optionally substituted 5, 6, 7, 8, 9 or 10-membered carbocyclic or heterocyclic moiety;

or $R^6$ is a group $ZR^7$ in which Z is $NR^b$, and $NR^b$ and $R^7$ together form an optionally substituted 5, 6, 7, 8, 9 or 10-membered carbocyclic or heterocyclic moiety.

2. The method as claimed in claim 1, wherein the susceptible cancer is a susceptible breast cancer.

3. The method as claimed in claim 1, wherein the susceptible cancer is a susceptible non-small cell lung cancer.

4. The method as claimed in claim 1, wherein the susceptible cancer is a susceptible ovarian cancer.

5. The method as claimed in claim 1, wherein the susceptible cancer is a susceptible stomach cancer.

6. The method as claimed in claim 1, wherein the susceptible cancer is a susceptible pancreatic cancer.

7. The method as claimed in claim 1, wherein the susceptible cancer is a susceptible head and neck cancer.

8. The method as claimed in claim 1, wherein the susceptible cancer is a susceptible cancer in which there is expression or over-expression of EGFR.

9. The method as claimed in claim 1, wherein the susceptible cancer is a susceptible cancer in which there is expression or over-expression of erbB-2.

10. The method as claimed in claim 1, wherein the susceptible cancer is a susceptible cancer in which there is expression or over-expression of EGFR and erbB-2.

11. The method as claimed in claim 1, wherein X is N.

12. The method as claimed in claim 1, wherein Y is $NR^b$, $NR^b(CH_2)$, or $(CH_2)NR^b$.

13. The method as claimed in claim 1, wherein $R^1$ is a 5- or 6-membered heterocyclic ring as defined in claim 1 substituted with an $R^3$ group selected from the group consisting of $M^1$-$M^2$-$M^3$-$M^4$, $M^1$-$M^5$ and $M^1$-$M^2$-$M^{3'}$-$M^6$ as defined in claim 1; and p=0.

14. The method as claimed in claim 1, wherein $M^1$ is $CH_2$, CO, $CH_2CH_2$ or $CH_2CO$; $M^2$ is $NR^{12}$ in which $R^{12}$ is as defined in claim 1; $M^3$ is $CH_2$, $CH_2CH_2$ or propyl; $M^{3'}$ is $CH_2$, ethyl, propyl, isopropyl or is absent; $M^4$ is $SOR^{13}$, $SO_2R^{13}$, $NR^{12}SO_2R^{13}$, $SO_2NR^{14}R^{15}$, $CO_2R^{13}$ or $CONR^{14}R^{15}$ in which $R^{12}$ and $R^{13}$ are defined in claim 1 and $R^{14}$ and $R^{15}$ each independently are H or $C_{1-4}$ alkyl; $M^5$ is a group $NR^{14}R^{15}$ in which $R^{14}$ and $R^{15}$ together with the nitrogen atom to which they are attached is a 6-membered ring optionally containing an additional heteroatom selected from N or O, in which ring any nitrogen atom present is optionally substituted with a $_{1-4}$ alkyl group; or $M^5$ is a group

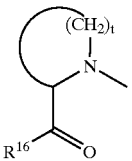

in which t is 2 or 3 and $R^{16}$ is OH, $NH_2$, $N(C_{1-4}$ alkyl$)_2$ or $OC_{1-4}$ alkyl; or $M^5$ is a group $NR^{14}R^{15}$ in which $R^{14}$ and $R^{15}$ each independently are hydrogen or $C_{1-4}$ alkyl; and $M^6$ is a group $NR^{14}R^{15}$ in which $R^{14}$ and $R^{15}$ each independently is $C_{1-4}$ alkyl, or $R^{14}$ and $R^{15}$ together with the nitrogen atom to which they are attached is a 5- or 6-membered ring optionally containing an additional heteroatom selected from N or O, in which ring any nitrogen atom present is optionally substituted with a $C_{1-4}$ alkyl group; or $M^6$ is a 5- or 6-membered heterocyclic ring system containing 1 or 2 heteroatoms selected from N or O.

15. The method as claimed in claim 1, wherein $M^2$-$M^3$-$M^4$ is a methylsulphonylethylamino, methylsulphinylethylamino, methylsulphonylethyl (methylamino), methylsulphinylethyl(methylamino), methylsulphonylpropylamino, methylsulphinylpropylamino, methylsulphonamidoethylamino, aminosulphonylethylamino, methylaminosulphonylethylamino, sarcosinamide, glycine, glycinamide, glycine methyl ester or acetylaminoethylamino group.

16. The method as claimed in claim 1, wherein $R^1$ is selected from the group consisting of comprising furan, dihydrofuran, thiophene, imidazole, tetrazole, triazole, pyridine, pyrrole, pyrimidine, isoxazole and oxadiazole.

17. The method as claimed in claim 1, wherein $R^1$ is selected from the group consisting of furan, imidazole, oxadiazole and triazole.

18. The method as claimed in claim 1, wherein $R^6$ is benzyl, fluorobenzyl, difluorobenzyl, benzyloxy, fluorobenzyloxy, pyridylmethyl, phenyl, benzenesulphonyl, phenoxy or fluorophenoxy.

19. The method as claimed in claim 1, wherein U is an phenyl, indolyl, isoindolyl, indolinyl, isoindolinyl, 1H-indazolyl, 2,3-dihydro-1H-indazolyl, 1H-benzimidazolyl, 2,3-dihydro-1H-benzimidazolyl or 1H-benzotriazolyl group.

20. The method as claimed in claim 1, wherein U is a phenyl or 1H-indazolyl group.

21. The method as claimed in claim 1, wherein the optional substituents for the carbocyclic or heterocyclic moiety include hydroxy, halogen, trifluoromethyl, trifluoromethoxy, nitro, amino, cyano, $C_{1-4}$ alkoxy, $C_{1-4}$ alkylthio, $C_{1-4}$ alkyl carbonyl, carboxylate and $C_{1-4}$ alkoxy carboxyl.

22. The method as claimed in claim 1, wherein X is N; Y is $NR^a$, wherein $R^a$ is hydrogen or $C_{1-4}$ alkyl; $R^1$ is furan, thiophene, pyrrole, pyridine, pyrimidine, pyrazine, imidazole, oxazole, isoxazole, oxadiazole, tetrazole, triazole, dioxolane or a partially or fully hydrogenated derivative of any of these groups, optionally substituted by one or more $R^3$ groups selected from halo, trifluoromethyl, $C_{1-4}$ alkyl, carboxy, $C_{1-4}$-alkoxycarbonyl, formyl, hydroxy-$C_{1-4}$ alkyl, 1,3-dioxolan-2-yl, amino, $C_{1-4}$ alkylamino, di($C_{1-4}$ alkyl)amino, hydroxy-$C_{1-4}$alkanoyl-($C_{1-4}$alkyl)-amino, $C_{1-4}$ alkylamino-$C_{1-4}$ alkyl or di($C_{1-4}$ alkyl)amino-$C_{1-4}$ alkyl; p is 0; $R^2$ is hydrogen; $R^4$ is hydrogen, halo or methyl; U is phenyl, indolyl, benzimidazolyl or indazolyl, more preferably phenyl or indazolyl; and $R^6$ is phenyl, benzyl, α-methylbenzyl, fluorobenzyl, difluorobenzyl, pyridylmethyl, benzenesulphonyl, phenoxy, fluorophenoxy, benzyloxy or fluorobenzyloxy.

23. The method as claimed in claim 1, wherein X is N; Y is $NR^a$, wherein $R^a$ is hydrogen or $C_{1-4}$ alkyl; $R^1$ is selected from the group consisting of a furan, dihydrofuran, thiophene, pyridine, pyrrole, pyrimidine, isoxazole, triazole, tetrazole, imidazole and oxadiazole ring, substituted with an $R^3$ group selected from the group consisting of $C_{1-4}$alkyl, $C_{1-4}$alkylamino-$C_{1-4}$-alkyl, di($C_{1-4}$alkyl)amino-$C_{1-4}$ alkyl, formyl, carboxy, $C_{1-4}$alkoxycarbonyl, dioxolanyl, trifluoromethyl, methylsulphonylethylaminomethyl, methylsulphonylethylamino-carbonyl, methylsulphonylethyl(methylamino)-methyl, methylsulphonamidoethylamino-methyl, aminosulphonylethylamino-methyl, methylaminosulphonylethylamino-methyl, N,N-dimethylaminoprop-2-ylaminomethyl, N-(2-dimethylaminoethyl)-N-ethylaminomethyl, pyridylaminomethyl, tetrahydrofuranomethylaminomethyl, piperazinylmethyl, methylpiperazinylmethyl, piperidinylmethyl, pyridylmethyl, N-(prolinamino)methyl and (N,N-dimethyl-prolinamido)methyl p is 0; $R^2$ is hydrogen; $R^4$ is hydrogen or halo; U is phenyl or indazolyl; and $R^6$ is selected from the group consisting of benzyl, fluorobenzyl, difluorobenzyl, pyridylmethyl, benzenesulphonyl, phenoxy, benzyloxy or fluorobenzyloxy.

* * * * *